US008507267B2

(12) United States Patent
Chiorini et al.

(10) Patent No.: US 8,507,267 B2
(45) Date of Patent: *Aug. 13, 2013

(54) AAV4 VECTOR AND USES THEREOF

(75) Inventors: John A. Chiorini, Kensington, MD (US); Robert M. Kotin, Bethesda, MD (US); Brian Safer, Silver Spring, MD (US); Nancy Safer, legal representative, Silver Spring, MD (US)

(73) Assignee: U.S. Dept. of Health and Human Services, National Institutes of Health, Washington, DC (US)

( * ) Notice: Subject to any disclaimer, the term of this patent is extended or adjusted under 35 U.S.C. 154(b) by 614 days.

This patent is subject to a terminal disclaimer.

(21) Appl. No.: 12/719,671

(22) Filed: Mar. 8, 2010

(65) Prior Publication Data
US 2010/0227407 A1 Sep. 9, 2010

Related U.S. Application Data

(63) Continuation of application No. 10/719,311, filed on Nov. 20, 2003, now Pat. No. 7,718,424, which is a continuation of application No. 09/254,747, filed as application No. PCT/US97/16266 on Sep. 11, 1997, now abandoned.

(60) Provisional application No. 60/025,934, filed on Sep. 11, 1996.

(51) Int. Cl.
C12N 15/35 (2006.01)
C12N 15/864 (2006.01)
C12N 7/02 (2006.01)
C12P 21/02 (2006.01)
C07H 21/04 (2006.01)

(52) U.S. Cl.
USPC ............. 435/320.1; 435/70.1; 435/235.1; 536/23.72

(58) Field of Classification Search
None
See application file for complete search history.

(56) References Cited

U.S. PATENT DOCUMENTS

| | | | |
|---|---|---|---|
| 6,146,874 A | 11/2000 | Zolotukhin et al. | |
| 6,180,613 B1 | 1/2001 | Kaplitt et al. | |
| 6,221,349 B1 | 4/2001 | Couto et al. | |
| 6,309,634 B1 | 10/2001 | Bankiewicz et al. | |
| 6,391,858 B2 | 5/2002 | Podsakoff et al. | |
| 6,485,976 B1 | 11/2002 | Nadler et al. | |
| 6,855,314 B1 | 2/2005 | Chiorini et al. | |
| 6,984,517 B1 | 1/2006 | Chiorini et al. | |
| 2002/0076754 A1 | 6/2002 | Sun et al. | |
| 2003/0228282 A1 | 12/2003 | Gao et al. | |
| 2004/0110266 A1 | 6/2004 | Chiorini et al. | |
| 2004/0115789 A1 | 6/2004 | Meruelo et al. | |
| 2005/0255089 A1 | 11/2005 | Chiorini et al. | |
| 2010/0227407 A1* | 9/2010 | Chiorini et al. ............. | 435/457 |

FOREIGN PATENT DOCUMENTS

| | | |
|---|---|---|
| DE | 44 36 664 A1 | 7/1996 |
| EP | 1 310 571 | 5/2003 |
| WO | WO 93/24641 A | 12/1993 |
| WO | WO 95/11997 A | 5/1995 |
| WO | WO 96/00587 | 1/1996 |
| WO | WO 96/15777 A | 5/1996 |
| WO | WO 96/18727 | 6/1996 |
| WO | WO 97/06272 | 2/1997 |
| WO | WO 98/41240 A | 9/1998 |
| WO | WO 98/45462 A | 10/1998 |
| WO | WO 99/61601 A | 12/1999 |
| WO | WO 00/26254 | 5/2000 |
| WO | WO 00/28061 | 5/2000 |
| WO | WO 01/70276 A | 9/2001 |
| WO | WO 01/83692 | 11/2001 |
| WO | WO 03/093479 | 11/2003 |
| WO | WO 2004/112727 A | 12/2004 |
| WO | WO 2005/017101 | 2/2005 |
| WO | WO 2005/056807 A | 6/2005 |
| WO | WO 2006/029196 | 3/2006 |
| WO | WO 2006/119432 | 11/2006 |

OTHER PUBLICATIONS

Chiorini et al. "Cloning of Adeno-Associated Virus Type 4 (AAV4) and Generation of Recombinant AAV4 Particles" *J. Virol.* 71(9):6823-6833, Sep. 1997.
Davidson BL et al. "Recombinant Adeno-associated Virus Type 2, 4, and 5 Vectors: Transduction of Variant Cell Types and Regions in the Mammalian Central Nervous System" *Proc. Natl Acad Sci.* 97(7):3428-32, Mar. 2000.
Kotin et al., "Organization of adeno-associated virus DNA in latently infected Detroit 6 cells." Virology 170(2):460-7 (1989).
Muramatsu et al. "Nucleotide Sequencing and Generation of an Infectious Clone of Adeno-Associated Virus 3" *Virology* 221:208-217, 1996.
Muster et al. "Physical Mapping of Adeno-Associated Virus Serotype 4 DNA" *J. Virol.* 35(3):653-661, Sep. 1980.
Salo R. and Mayor H. "Structural Polypeptides of Parvoviruses" *Virology* 78:340-345, 1977.
Srivastava et al. "Nucleotide Sequence and Organization of the Adeno-Associated Virus 2 Genome" *J. Virol.* 45(2):555-564, Feb. 1983.
Shin-Ichi et al., "Nucleotide Sequencing and genergation of an infectious clone of adeno-associated virus 3," Virology, 221(1):208-217, 1996.
Alexander et al., "DNA-Damaging Agents Greatly Increase the Transduction of Nondividing Cells by Adeno-Associated Virus Vectors," Dec. 1994, *J. Virol.*, 68(12):8282-8287.
Alisky et al., "Transduction of Murine Cerebellar Neurons with Recombinant FIV and AAV5 Vectors," *Mol. Neurosci.*, Aug. 2000, 11(1221):2669-2673.
Alisky J.M. and Tolbert D.M., "Differential labeling of converging afferent pathways using biotinylated dextran amine and cholera toxin subunit B," 1994, *Journal of Neuroscience Methods*, 52:143-148.

(Continued)

Primary Examiner — Michael Burkhart
(74) Attorney, Agent, or Firm — Sheridan Ross P.C.

(57) ABSTRACT

The present invention provides an adeno-associated virus 4 (AAV4) virus and vectors and particles derived therefrom. In addition, the present invention provides methods of delivering a nucleic acid to a cell using the AAV4 vectors and particles.

35 Claims, 3 Drawing Sheets

(56) References Cited

OTHER PUBLICATIONS

Allen, J.M., Halbert, C.L. and Miller, A.D., "Improved adeno-associated virus vector production with transfection of a single helper adenovirus gene, E4orf6," 2000, *Mol Ther*, 1:88-95.
Arnberg, N., A. H. Kidd, K. Edlund, J. Nilsson, P. Pring-Akerblom, and G. Wadell, "Adenovirus type 37 binds to cell surface sialic acid through a charge-dependent interaction," 2002, *Virology*, 302:33-43.
Atchison, R. W., B. C. Casto, and W. M. Hammon, "Adenovirus-Associated Defective Virus Particles," 1965, *Science*, 149:754-756.
Auricchio et al., "A Single-Step Affinity Column for Purification of Serotype-5 Based Adeno-Associated Viral Vectors," Oct. 2001, *Mol Ther* 4(4):372-374.
Bachmann, P.A., M.D. Hoggan, E. Kurstak, J.L. Melnick, H.G. Pereira, P. Tattersall, and C. Vago, "Parvoviridae: second report," 1979, *Interverology*, 11:248-254.
Bajocchi G, Feldman SH, Crystal RG, Mastrangeli A., "Direct in vivo gene transfer to ependymal cells in the central nervous system using recombinant adenovirus vectors," 1993, *Nat Genet*, 3:229-234.
Bantel-Schaal U, Delius H, Schmidt R, zur Hausen H., "Human adeno-associated virus type 5 is only distantly related to other known primate helper-dependent parvoviruses," 1999, *J Virol.*, 73(2):939-947.
Bantel-Schaal U, zur Hausen H., "Characterization of the DNA of a defective human parvovirus isolated from a genital site," 1984, *Virology*, 134(1):52-63, XP009028974.
Bantel-Schaal, U. and M. Stohr, "Influence of adeno-associated virus on adherence and growth properties of normal cells," 1992, *J. Virol.*, 66:773-779.
Bantel-Schaal, U., Hub, B. and Kartenbeck, J., "Endocytosis of adeno-associated virus type 5 leads to accumulation of virus particles in the Golgi compartment," 2002, *J Virol* 76:2340-2349.
Bartlett JS, Kleinschmidt J., Boucher RC, and Samulski RJ, "Targeted adeno-associated virus vector transduction of nonpermissive cells mediated by a bispecific F(ab'gamma)$_2$ antibody," 1999, *Nat Biotechnol*, 17:181-186.
Bartlett JS, Samulski RJ, McCown TJ., "Selective and rapid uptake of adeno-associated virus type 2 in brain," 1998, *Hum Gene Ther*, 9(8):1181-1186.
Bartlett, J.S., Wilcher, R. and Samulski, R.J., "Infectious entry pathway of adeno-associated virus and adeno-associated virus vectors," 2000, *J Virol*, 74:2777-2785.
Ben-Israel, H. and Kleinberger, T., "Adenovirus and cell cycle control," 2002, *Front Biosci*, 7:d1369-1395.
Bergelson, JM, Cunningham JA, Droguett G., Kurt-Jones EA, Krithivas A., Hong JS, Horwitz MS, Crowell RL, and Finberg RW, "Isolation of a common receptor for Coxsackie B viruses and adenoviruses 2 and 5," 1997, *Science*, 275:1320-1323.
Blacklow, et al., "Serologic Evidence for Human Infection With Adenovirus-Associated Viruses," 1968, *J NCI*, 40(2):319-327.
Blacklow, N.R., Hoggan, M.D. and Rowe, W.P. "Isolation of adenovirus-associated viruses from man," 1967, *Proc Nati Acad Sci U S A*, 58:1410-1415.
Bomsel M, Alfsen A, "Entry of viruses through the epithelial barrier: pathogenic trickery," 2003, *Nat Rev Mol Cell Biol*, 4:57-68.
Bomsel M, David V, "Mucosal gatekeepers: selecting HIV viruses for early infection," 2002, *Nat Med*, 8:114-116.
Bossis, I. and Chiorini, J.A., "Cloning of an Avian Adeno-Associated Virus (AAAV) and Generation of Recombinant AAAV Particles," 2003, *J Virol*, 77(12):6799-6810.
Burcin, M.M., O'Malley, B.W. and S.Y. Tsai, "A regulatory system for target gene expression," 1998, *Frontiers in Bioscience*, 3:c1-7.
Carter, B. J., B. A. Antoni, and D. F. Klessig, "Adenovirus containing a deletion of the early region 2A gene allows growth of adeno-associated virus with decreased efficiency," 1992, *Virology*, 191:473-476.
Carter, B. J., C. A. Laughlin, L. M. de la Maza, and M. Myers, "Adeno-associated virus autointerference," 1979, *Virology*, 92:449-462.
Casto, B. C., R. W. Atchison, and W. M. Hammon, "Studies on the relationship between adeno-associated virus type I (AAV-1) and adenoviruses. I. Replication of AAV-1 in certain cell cultures and its effect on helper adenovirus," 1967a, *Virology*, 32:52-59.
Casto, B. C., J. A. Armstrong, R. W. Atchison, and W. M. Hammon, "Studies on the relationship between adeno-associated virus type 1 (AAV-1) and adenoviruses. II. Inhibition of adenovirus plaques by AAV; its nature and specificity," 1967b, *Virology*, 33:452-458.
Chang, L.S. and Shenk, T., "The adenovirus DNA-binding protein stimulates the rate of transcription directed by adenovirus and adeno-associated virus promoters," 1990, *J Virol*, 64:2103-2109.
Chang, L.S., Y. Shi, and T. Shenk, "Adeno-associated virus P5 promoter contains an adenovirus E1A-inducible element and a binding site for the major late transcription factor," 1989, *J. Virol.*, 63:3479-3488.
Chao H et al., "Several Log Increase in Therapeutic Transgene Delivery by Disticnt Adeno-Associated Viral Serotype Vectors," 2000, *Molecular Therapy*, 2(6):619-623.
Chejanovsky, N. and B.J. Carter, "Mutagenesis of an AUG codon in the adeno-associated virus rep gene: effects on viral DNA replication," 1989b, *Virology*, 173:120-128.
Chejanovsky, N. and B.J. Carter, "Replication of a human parvovirus nonsense mutant in mammalian cells containing an inducible amber suppressor," 1989a, *Virology*, 171:239-247.
Chiorini JA, Afione S, Kotin RM, "Adeno-associated virus (AAV) type 5 Rep protein cleaves a unique terminal resolution site compared with other AAV serotypes," May 1999a, *J Virol*, 73(5):4293-4298.
Chiorini JA, Kim F, Yang L, Kotin RM, "Cloning and characterization of adeno-associated virus type 5," Feb. 1999b, *J Virol.*, 73(2):1309-1319, XP-002125035.
Chiorini, J.A., C.M. Wendtner, E. Urcelay, B. Safer, M. Hallek, and R.M. Kotin, "High-efficiency transfer of the T cell co-stimulatory molecule B7-2 to lymphoid cells using high-titer recombinant adeno-associated virus vectors," 1995, *Human Gene Therapy*, 6:1531-1541.
Chiorini, J.A., L. Yang, B. Safer, and R.M. Kotin, "Determination of adeno-associated virus Rep68 and Rep78 binding sites by random sequence oligonucleotide selection," 1995, *J. Virol.*, 69:7334-7338.
Chiorini, J.A., M.D. Weitzman, R.A. Owens, E. Urcelay, B. Safer, and R.M. Kotin, "Biologically active Rep proteins of adeno-associated virus type 2 produced as fusion proteins in *Escherichia coil*," 1994a, *J. Virol.*, 68:797-804.
Chiorini, J.A., S.M. Wiener, R.M. Kotin, R.A. Owens, SRM Kyöstiö, and B. Safer, "Sequence requirements for stable binding and function of Rep68 on the adeno-associated virus type 2 inverted terminal repeats," 1994b, *J. Virol.*, 68:7448-7457.
Clark et al., "Highly Purified Recombinant Adeno-Associated Virus Vectors are Biologically Active and Free of Detectable Helper and Wild-Type Viruses," 1999, *Hum. Gene Ther.* 10:1031-1039.
Cohen-Salmon et al., "Targeted ablation of connexin26 in the inner ear epithelial gap junction network causes hearing impairment and cell death," 2002, *Curr Biol*, 12:1106-1111.
Coria et al., "Isolation and identification of a bovine adenovirus type 3 with an adenovirus-associated virus," 1978, *American Journal of Veterinary Research*, 39(12):1904-1906, XP009050511.
Crystal RG, "Transfer of genes to humans: early lessons and obstacles to success," 1995, *Science*, 270(5235):404-410.
Database EMBL, Entry GGACTAA, GenBank Accession No. M61166, Mar. 27, 1991, XP002125220.
Davidson BL, Doran SE, Shewach DS, Latta JM, Hartman JW, Roessler BJ., "Expression of *Escherichia coli* beta-galactosidase and rat HPRT in the CNS of *Macaca mulatta* following adenoviral mediated gene transfer," 1994, *Exp Neurol*, 125:258-267.
Deonarain MP, "Ligand-targeted receptor-mediated vectors for gene delivery," *Molecular Conjugate Vectors*, 1998, 8(1):53-69.
Derby, M. L., M. Sena-Esteves, et al., "Gene transfer into the mammalian inner ear using HSV-1 and vaccinia virus vectors," 1999, *Hear Res* 134(1-2):1-8.
Di Pasquale, G., Rzadzinska, A., Schneider, M.E., Bossis, I., Chiorini, J.A., Kachar, B., "A novel bovine virus efficiently transduces inner ear neuroepithelial cells," 2005, *Molecular Therapy*, Academic Press, 11(6):849-855, XP004908862.
Di Pasquale, G., and J. A. Chiorini, "PKA/PrKX activity is a modulator of AAV/adenovirus interaction," 2003, *EMBO J*, 22:1716-1724.
Di Pasquale, G., B. L. Davidson, et al., "Identification of PDGFR as a receptor for AAV-5 transduction," 2003, *Nat Med* 9(10):1306-1312.

Dixit, M., M.S. Webb, W.C. Smart, and S. Ohi, "Construction and expression of a recombinant adeno-associated virus that harbors a human *beta*-globin-encoding cDNA," 1991, *Gene* 104:253-257.

Doll RF, Crandall JE, Dyer CA, Aucoin JM, Smith FI., "Comparison of promoter strengths on gene delivery into mammalian brain cells using AAV vectors," 1996, *Gene Ther*, 3:437-447.

Duan, D., Yue Y., Yan Z., McCray PBJr, and Engelhardt JF., "Polarity influences the efficiency of recombinant adenoassociated virus infection in differentiated airway epithelia," 1998, *Hum Gene Ther*, 9:2761-2776.

During MJ, Symes CW, Lawlor PA, Lin J, Dunning J, Fitzsimons HL, Poulsen D, Leone P, Xu R, Dicker BL, Lipski J, Young D, "An oral vaccine against NMDAR1 with efficacy in experimental stroke and epilepsy," 2000, *Science*, 287:1453-1460.

During MJ, Xu R, Young D, Kaplitt MG, Sherwin RS, Leone P., "Peroral gene therapy of lactose intolerance using an adeno-associated virus vector," 1998, *Nat Med*, 4(10):1131-1135.

During MJ, Leone P, "Adeno-associated virus vectors for gene therapy of neurodegenerative disorders," 1995-96, *Clin Neurosci*, 3(5):292-300, XP-002125034.

Erles, K., Sebokova, P. and Schlehofer, J.R., "Update on the prevalence of serum antibodies (IgG and IgM) to adeno-associated virus (AAV)," 1999, *J Med Virol*, 59:406-411.

Fan D-S, Ogawa M, Fujimoto K-I, Ikeguchi K, Ogasawara Y, Urabe M, Nishizawa M, Nakano I, Yoshida M, Nagatsu I, Ichinose H, Nagatsu T, Kurtzman GJ, Ozawa K, "Behavioral recovery in 6-hydroxydopamine-lesioned rats by cotransduction of striatum with tyrosine hydroxylase and aromatic L-amino acid decarboxylase genes using two separate adeno-associated virus vectors," 1998, *Hum Gene Ther*, 9:2527-2535.

Fisher, KJ, Jooss K., Alston J., Yang Y., Haecker SE, High K., Pathak R., Raper SE, and Wilson JM, "Recombinant adeno-associated virus for muscle directed gene therapy," 1997, *Nat Med*, 3:306-312.

Fisher, R.E., H.D. Mayor, "The evolution of defective and autonomous parvoviruses," 1991, *J Theor Biol* 149:429-439.

Flannery et al., "Efficient Photoreceptor-targeted Gene Expression in vivo by Recombinant Adeno-Associated Virus," 1997, *Proc Natl Acad Sci USA*, 94:6916-6921.

Flotte TR, Solow R, Owens RA, Afione S, Zeitlin PL, Carter BJ, "Gene expression from adeno-associated virus vectors in airway epithelial cells," 1992, *Am J Respir Cell Mol Biol*, 7(3):349-356; XP000609213.

Flotte, T.R., S.A. Afione, C. Conrad, S.A. McGrath, R. Solow, H. Oka, P.L. Zeitlin, W.B. Guggino, and B.J. Carter, "Stable in vivo expression of the cystic fibrosis transmembrane conductance regulator with an adeno-associated virus vector," 1993, *Proc. Natl. Acad. Sci.*, 90:10613-10617.

Flotte, T.R., S.A. Afione, R. Solow, M.L. Drumm, D. Markakis, W.B. Guggino, P.L. Zeitlin, and B.J. Carter, "Expression of the cystic fibrosis transmembrane conductance regulator from a novel adeno-associated virus promoter," 1993, *J Biol Chem*, 268:3781-3790.

Frolenkov GI, Belyantseva IA, Friedman TB, Griffith AJ, "Genetic insights into the morphogenesis of inner ear hair cells," 2004, *Nat Rev Genet*, 5:489-498.

Gao, G., L. H. Vandenberghe, M. R. Alvira, Y. Lu, R. Calcedo, X. Zhou, and J. M. Wilson, "Clades of Adeno-associated viruses are widely disseminated in human tissues," 2004, *J Virol*, 78:6381-6388.

Gao, G.P., Alvira, M.R., Wang, L., Calcedo, R., Johnston, J. and Wilson, J.M., "Novel adeno-associated viruses from rhesus monkeys as vectors for human gene therapy," 2002, *Proc Natl Acad Sci USA*, 99:11854-11859.

Georg-Fries B, Biederlack S, Wolf J, zur Hausen H, "Analysis of proteins, helper dependence, and seroepidemiology of a new human parvovirus," 1984, *Virology*, 134(1):64-71, XP002027460.

Ghodsi A., Stein C., Derksen T., Martins I., Anderson RD, & Davidson BL, "Systemic hyperosmolality improves *beta*-glucuronidase distribution and pathology in murine MPS VII brain following intraventricular gene transfer," 1999, *Exp Neurol*, 160:109-116.

Ghodsi A., Stein, C., Derksen T., Yang, G., Anderson R.D., Davidson B.L., "Extensive *beta*-glucuronidase activity in murine central nervous system after adenovirus-mediated gene transfer to brain," 1998, *Hum Gene Ther*, 9:2331-2340.

Girod A., Ried M., Wobus C., Lahm H., Leike K., Kleinschmidt J., Deleage G., and Hallek M., "Genetic capsid modifications allow efficient re-targeting of adeno-associated virus type 2," 1999, *Nat Med*, 5:1052-1056.

Grimm, D. and M. A. Kay, "From virus evolution to vector revolution: use of naturally occurring serotypes of adeno-associated virus (AAV) as novel vectors for human gene therapy," 2003, *Curr Gene Ther*, 3(4)::281-304.

Grimm D and Kern A, Rittner K Kleinschmidt JA, "Novel Tools for Production and Purification of Recombinant Adenoassociated Virus Vectors," 1998, *Human Gene Therapy*, 9:2745-2760.

Guy J., Qi X., Muzyczka N., and Hauswirth WW, "Reporter expression persists 1 year after adeno-associated virus-mediated gene transfer to the optic nerve," 1999, *Arch Ophthalmol*, 117:929-937.

Halbert CL, Standaert TA, Aitken ML, Alexander IE, Russell DW, and Miller AD, "Transduction by adeno-associated virus vectors in the rabbit airway: efficiency, persistence, and readministration," 1997, *J. Virol.*, 71:5932-5941.

Halbert, C. L., J. M. Allen, and A. D. Miller, "Adeno-associated virus type 6 (AAV6) vectors mediate efficient transduction of airway epithelial cells in mouse lungs compared to that of AAV2 vectors," 2001, *J Virol*, 75:6615-6624.

He, D. Z., J. Zheng, et al., "Development of acetylcholine receptors in cultured outer hair cells," 2001, *Hear Res* 162(1-2):113-125.

Hehir K.M., Armentano D., Cardoza L.M., Choquette T.L., Berthelette P.B., White G.A., Couture L.A., Everton M.B., Keegan J., Martin J.M., Pratt D.A., Smith M.P., Smith A.E., Wadsworth S.C., "Molecular characterization of replication-competent variants of adenovirus vectors and genome modifications to prevent their occurrence," 1996, *J Virol*, 70(12):8459-8467.

Heister, T., Heid, I. Ackermann, M., Fraefel, C., "Herpes simplex virus type 1/adeno-associated virus hybrid vectors mediate site-specific integration at the adeno-associated virus preintegration site, AAVS1, on human chromosome 19," 2002 *J Virol*, 76(14):7163-7173.

Hermonat PL, Santin AD, De Greve J, De Rijcke M, Bishop BM, Han L, Mane M, Kokorina N, "Chromosomal latency and expression at map unit 96 of a wild-type plus adeno-associated virus (AAV)/Neo vector and identification of p81, a new AAV transcriptional promoter," Nov.-Dec. 1999, *J Hum Virol.*, 2(6):359-368.

Hermonat, PL and N. Muzyczka, "Use of adeno-associated virus as a mammalian DNA cloning vector: transduction of neomycin resistance into mammalian tissue culture cells," 1984, *Proc Natl Acad Sci USA*, 81:6466-6470.

Hermonat, P.L., M.A. Labow, R. Wright, K.I. Berns, and N. Muzyczka, "Genetics of adeno-associated virus: isolation and preliminary characterization of adeno-associated virus type 2 mutants," 1984, *J. Virol.*, 51:329-339.

Hoggan, M. D., N. R. Blacklow, and W. P. Rowe, "Studies of small DNA viruses found in various adenovirus preparations: physical, biological, and immunological characteristics," 1966, *Proc Natl Acad Sci USA*, 55:1467-1474.

Hoggan, M.D., "Adenovirus associated viruses," 1970, *Prog Med Virol*, 12:211-239.

Holt, J. R., "Viral-mediated gene transfer to study the molecular physiology of the Mammalian inner ear" 2002, *Audiol Neurootol*, 7(3):157-160.

Holt, J. R., D. C. Johns, et al., "Functional expression of exogenous proteins in mammalian sensory hair cells infected with adenoviral vectors," 1999, *J Neurophysiol*, 81(4):1881-1888.

Hsueh Y-P, Sheng M., "Regulated expression and subcellular localization of syndecan heparan sulfate proteoglycans and the syndecan-binding protein CASK/LIN-2 during rat brain development," 1999, *J Neurosci*, 19(17):7415-7425.

Hsueh Y-P, Yang F-C, Kharazia V, Naisbitt S, Cohen AR, Weinberg RJ, Sheng M, "Direct interaction of CASK/LIN-2 and syndecan heparan sulfate proteoglycan and their overlapping distribution in neuronal synapses," 1998, *J Cell Biol*, 142(1):139-151.

Hull, R. N., J. R. Minner, and J. W. Smith, "New viral agents recovered from tissue cultures of monkey kidney cells. I. Origin and properties of cytopathogenic agents S.V.1, S.V.2, S.V.4, S.V.5, S.V.6, S.V.11, S.V.12 and S.V.15," 1956, *Am J Hyg*, 63:204-215.

Hull, R. N., and J. R. Minner, "New viral agents recovered from tissue cultures of monkey kidney cells. II. Problems of isolation and identification," 1957, *Ann NY Acad Sci*, 67:413-423.

Hull, R. N., J. R. Minner, and C. C. Mascoli, "New viral agents recovered from tissue cultures of monkey kidney cells. III. Recovery of additional agents both from cultures of monkey tissues and directly from tissues and excreta," 1958, *Am J Hyg*, 68:31-44.

Hunter, L.A. and R.J. Samuiski, "Colocalization of adeno-associated virus Rep and capsid proteins in the nuclei of infected cells," 1992, *J. Virol*, 66:317-324.

Im DS, Muzyczka N, "Partial purification of adeno-associated virus Rep78, Rep52, and Rep40 and their biochemical characterization," Feb. 1992, *J Virol.*, 66(2):1119-1128, XP002125031.

Inglis VI, Jones MP, Tse AD, Easton AS, "Neutrophils both reduce and increase permeability in a cell culture model of the blood-brain barrier," 2004, *Brain Res*, 998(2):218-229.

Ito, M. and H.D. Mayor, "Hemagglutinin of type 4 adeno-associated satellite virus," 1968, *J. Immunol*, 100:61-68.

Jaksch, M., K.D. Gerbitz, and C. Kilger, "Screening for mitochondrial DNA (mtDNA) point mutations using nonradioactive single strand conformation polymorphism (SSCP) analysis," 1995 *Clin. Biochem.*, 28:503-509.

Janik, J.E., M.M. Huston, K. Cho, and J.A. Rose, "Efficient syntheses of adeno-associated virus structural proteins requires both adenovirus DNA binding protein and VA I RNA," 1989, *Virology* 168:320-329.

Jero J, Mhatre AN, Tseng CJ, Stem RE, Coling DE, Goldstein JA, Hong K, Zheng WW, Hogue AT, Lalwani AK., "Cochlear gene delivery through an intact round window membrane in mouse," 2001, *Hum Gene Ther*, 12(5):539-548.

Johansson CB, Momma S, Clarke DL, Risling M, Lendahl U, Frisen J, "Identification of a neural stem cell in the adult mammalian central nervous system," 1999, *Cell*, 96(1):25-34.

Kaludov et al., "Adeno-Associated Virus Serotype 4 (AAV4) and AAV5 Both Require Sialic Acid Binding for Hemagglutination and Efficient Transduction but Differ in Sialic Acid Linkage Specificity" 2001, *J. Virol.*, 75(15):6884-6893.

Kaludov et al., "Scalable Purification of Adeno-Associated Virus Type 2, 4 or 5 Using Ion-Exchange Chromatography," 2002, *Human Gene Therapy*, 13:1235-1243.

Kanzaki, S., K. Ogawa, et al., "Transgene expression in neonatal mouse inner ear explants mediated by first and advanced generation adenovirus vectors," 2002, *Hear Res*, 169(1-2):112-120.

Kaplitt, M.G., P. Leone, R.J. Samulski, X. Xiao, D.W. Pfaff, K.L. O'Malley, and J.M. During, "Long-term gene expression and phenotypic correction using adeno-associated virus vectors in the mammalian brain," 1994, *Nature Genetics*, 8:148-154.

Katano et al., "Identification of adeno-associated virus contamination in cell and virus stocks by PCR," Apr. 2004, *Biotechniques*, 36(4):676-680, XP001207105.

Kelsell, D.P., Dunlop, J., Stevens, H.P., Lench, N.J., Liang, J.N., Parry, G., Mueller, R.F., Leigh, I.M., "Connexin 26 mutations in hereditary non-syndromic sensorineural deafness," 1997, *Nature*, 387(6628):80-83.

Kern, A., K. Schmidt, C. Leder, O. J. Muller, C. E. Wobus, K. Bettinger, C. W. Von der Lieth, J. A. King, and J. A. Kleinschmidt, "Identification of a heparin-binding motif on adeno-associated virus type 2 capsids," 2003, *J Virol*, 77:11072-11081.

Klein RL, Meyer EM, Peel AL, Zolotukhin S, Meyers C, Muzyczka N, King MA., "Neuron-specific transduction in the rat septohippocampal or nigrostriatal pathway by recombinant adeno-associated virus vectors," 1998, *Exp Neurol*, 150:183-194.

Kondo M., Finkbeiner WE, and Widdicombe JH., "Simple technique for culture of highly differentiated cells from dog tracheal epithelium," 1991, *Am.J.Physiol*, 261:L106-L117.

Kotin, R.M., M. Siniscalco, R.J. Samulski, X. Zhu, L. Hunter, C.A. Laughlin, S. McLaughlin, N. Muzyczka, M. Rocchi, and K.I. Berns, "Site-specific integration by adeno-associated virus," 1990, *Proc. Natl. Acad. Sci. USA*, 87:2211-2215.

Kovacs P, Pinter M, Csaba G, "Effect of glucosphingolipid synthesis inhibitor (PPMP and PDMP) treatment on *Tetrahymena pyriformis*: data on the evolution of the signaling system," 2000, *Cell Biochem Funct*, 18(4):269-280.

Kyo S, Nakamura M, Kiyono T, Maida Y, Kanaya T, Tanaka M, Yatabe N, Inoue M, "Successful immortalization of endometrial glandular cells with normal structural and functional characteristics," 2003, *Am J Pathol*, 163(6):2259-2269.

Kyostio SR, Owens RA, Weitzman MD, Antoni BA, Chejanovsky N, Carter BJ, "Analysis of adeno-associated virus (AAV) wild-type and mutant Rep proteins for their abilities to negatively regulate AAV $p_5$ and $p_{19}$ mRNA levels," 1994, *J Virol*, 68(5):2947-2957, XP-002125032.

Laughlin, C.A., M.W. Myers, D.L. Risin, B.J. Carter, "Defective-interfering particles of the human parvovirus adeno-associated virus," 1979, *Virology*, 94:162-174.

Laughlin, C.A., N. Jones, and B.J. Carter, "Effect of deletions in adenovirus early region 1 genes upon replication of adeno-associated virus," 1982, *J. Virol*, 41:868-876.

Lee K, Kim YG, Jo EC, "Shuttle PCR-based cloning of the infectious adeno-associated virus type 5 genome," 2003, *J Virol Methods*, 111(2):75-84.

Li J, Samulski RJ, Xiao X, "Role for Highly Regulated *rep* Gene Expression in Adeno-Associated Virus Vector Production," *J Virol*, 1997, 71(7):5236-5243.

Li Duan, M., T. Bordet, et al., "Adenoviral and adeno-associated viral vector mediated gene transfer in the guinea pig cochlea," 2002, *Neuroreport*, 13(10):1295-1299.

Liang Y, Annan RS, Carr SA, Popp S, Mevissen M, Margolis RK, Margolis RU., "Mammalian homologues of the *Drosophila* slit protein are ligands of the heparan sulfate proteoglycan glypican-1 in brain," 1999, *J Biol Chem*, 274(25):17885-17892.

Lo WD, Qu G, Sferra TJ, Clark R, Chen R, Johnson PR., "Adeno-associated virus-mediated gene transfer to the brain: duration and modulation of expression," 1999, *Hum Gene Ther*, 10:201-213.

Luchsinger, E., Strobbe, R., Dekegel, D. and Wellemans, G., "Use of B-IV zonal rotor centrifugation as a simple tool for the separation of adeno-associated X 7 virus (AAVX 7 ) from helper adenoviruses," 1971, *Arch Gesamte Virusforsch*, 33:251-258.

Luchsinger, E., Strobbe, R., Wellemans, G., Dekegel, D. and Sprecher-Goldberger, S., "Haemagglutinating adeno-associated virus (AAV) in association with bovine adenovirus type 1," 1970, *Brief report. Arch Gesamte Virusforsch*, 31:390-392.

Luebke, A. E., J. D. Steiger, et al., "A modified adenovirus can transfect cochlear hair cells in vivo without compromising cochlear function," 2001, *Gene Ther*, 8(10):789-794.

Luebke, A. E., P. K. Foster, et al., "Cochlear function and transgene expression in the guinea pig cochlea, using adenovirus- and adeno-associated virus-directed gene transfer," 2001, *Hum Gene Ther*, 12:773-781.

Maeda Y, Ikeda U, Ogasawara Y, Urabe M, Takizawa T, Saito T, Colosi P, Kurtzman G, Shimada K, Ozawa K, "Gene transfer into vascular cells using adeno-associated virus (AAV) vectors," 1997, *Cardiovasc Res*, 35(3):514-521, XP-002125030.

Mandel RJ, Rendahl KG, Spratt SK, Snyder RO, Cohen LK, Leff SE., "Characterization of intrastriatal recombinant adeno-associated virus-mediated gene transfer of human tyrosine hydroxylase and human GTP-cyclohydrolase I in a rat model of Parkinson's disease," 1998, *J Neurosci*, 18(11):4271-4284.

McCarty, D.M., J. Pereira, I. Zolotukhin, X. Zhou, J.H. Ryan, and N. Muzyczka, "Identification of linear DNA sequences that specifically bind the adeno-associated virus Rep protein," 1994, *J. Virol.*, 68:4988-4997.

McCown TJ, Xiao X, Li J, Breese GR, Samuiski RJ, "Differential and Persistent Expression Patterns of CNS Gene Transfer by an Adeno-Associated Virus (AAV) Vector," 1996, *Brain Res*, 713:99-107.

McPherson, R. A., L. J. Rosenthal, and J. A. Rose, "Human cytomegalovirus completely helps adeno-associated virus replication," 1985, *Virology*, 147:217-222.

Mendelson, E., J.P. Trempe, and B.J. Carter "Identification of the trans-acting Rep proteins of adeno-associated virus by antibodies to a synthetic oligopeptide," 1986, *J. Virol.*, 60:823-832.

Meyers, C., Mane, M., Kokorina, N., Alam, S. and Hermonat, P.L., "Ubiquitous human adeno-associated virus type 2 autonomously replicates in differentiating keratinocytes of a normal skin model," 2000, *Virology*, 272:338-346.

Mitrani E, Ziv T, Thomsen G, Shimoni Y, Melton DA, Bril A, "Activin can induce the formation of axial structures and is expressed in the hypoblast of the chick," 1990, *Cell*, 63(3):495-501.

Mizukami, H., N.S. Young, and K.E. Brown, "Adeno-associated virus type 2 binds to a 150-kilodalton cell membrane glycoprotein," 1996, *Virology*, 217:124-130.

Mori, S., L. Wang, T. Takeuchi, and T. Kanda, "Two novel adeno-associated viruses from cynomolgus monkey: pseudotyping characterization of capsid protein," 2004, *Virology*, 330:375-383.

Mouw, M.B. and Pintel, D.J., "Adeno-associated virus RNAs appear in a temporal order and their splicing is stimulated during coinfection with adenovirus," 2000, *J Virol*, 74:9878-9888.

Muzyczka, N, "Use of adeno-associated virus as a general transduction vector for mammalian cells," 1992, *Curr Top Microbiol Immunol*, 158:97-129.

Myrup, A.C., Mohanty, S.B. and Hetrick, F.M., "Isolation and characterization of adeno-associated viruses from bovine adenovirus types 1 and 2," 1976, *Am J Vet Res*, 37(8):907-910.

Naz, S., Griffit,h A.J., Riazuddin, S., Hampton, L.L., Battey, J.F. Jr, Khan, S.N., Riazuddin, S., Wilcox, E.R., Friedman, T.B., "Mutations of *ESPN* cause autosomal recessive deafness and vestibular dysfunction," 2004, *J Med Genet*, 41(8):591-595.

No D, Yao TP, Evans RM., "Ecdysone-inducible gene expression in mammalian cells and transgenic mice," 1996, *Proc Natl Acad Sci USA*, 93(8):3346-3351.

Ogston, P., K. Raj, and P. Beard, "Productive replication of adeno-associated virus can occur in human papillomavirus type 16 (HPV-16) episome containing keratinocytes and is augmented by the HPV-16 E2 protein," 2000, *J Virol*, 74:3494-3504.

Opie et al., "Identification of amino acid residues in the capsid proteins of adeno-associated virus type 2 that contribute to heparan sulfate proteoglycan binding," 2003, *J Virol*, 77:6995-7006.

O'Riordan et al., "Scaleable Chromatographic Purification Process for Recombinant Adeno-Associated Virus (rAAV)," 2000, *J Gene Med*, 2:444-454.

Parks, W.P., J.L. Melnick, R. Rongey, and H.D. Mayor, "Physical assay and growth cycle studies of a defective adeno-satellite virus," 1967, *J. Virol.*, 1:171-180.

Podsakoff, G., K.K. Jr Wong, and S. Chatterjee, "Efficient gene transfer into nondividing cells by adeno-associated virus-based vectors," 1994, *J. Virol.*, 68:5656-5666.

Polishchuk R, Di Pentima A, Lippincott-Schwartz J, "Delivery of raft-associated, GPI-anchored proteins to the apical surface of polarized MDCK cells by a transcytotic pathway," 2004, *Nat Cell Biol*, 6(4):297-307.

Prasad KM, Zhou C, Trempe JP, "Characterization of the Rep78/adeno-associated virus complex," 1997, *Virology*, 229(1):183-192, XP-002125033.

Qing K, Mah C, Hansen J, Zhou S, Dwarki V, Srivastava A., "Human fibroblast growth factor receptor 1 is a co-receptor for infection by adeno-associated virus 2," 1999, *Nat Med*, 5(1):71-77.

Qiu J, Brown KE., "Integrin *alphaVbeta5* is not involved in adeno-associated virus type 2 (AAV2) infection," 1999, *Virology*, 264(2):436-440.

Rabinowitz et al., "Cross-Packaging of a Single Adeno-Associated Virus (AAV) Type 2 Vector Genome into Multiple AAV Serotypes Enables Transduction with Broad Specificity," 2002, *J Virol*, 76(2):791-801, XP002247245.

Rabinowitz JE, Bowles DE, Faust SM, Ledford JG, Cunningham SE, Samulski RJ., "Cross-dressing the virion: the transcapsidation of adeno-associated virus serotypes functionally defines subgroups," 2004, *J Virol*, 78(9):4421-4432.

Reddy, V. S., P. Natarajan, B. Okerberg, K. Li, K. V. Damodaran, R. T. Morton, C. L. Brooks, 3rd, and J. E. Johnson, "Virus Particle Explorer (VIPER), a website for virus capsid structures and their computational analyses," 2001, *J Virol*, 75:11943-11947.

Rich DP, Couture LA, Cardoza LM, Guiggio LM, Armentano D., Espino PC, Hehir K., Welsh MJ, Smith AE, and Gregory RJ, "Development and analysis of recombinant adenoviruses for gene therapy of cystic fibrosis," 1993, *Hum. Gene Ther.*, 4:461-476.

Richardson, W. D., and H. Westphal, "Requirement for either early region 1a or early region 1b adenovirus gene products in the helper effect for adeno-associated virus," 1984, *J Virol*, 51:404-410.

Rose, J.A., M.D. Hoggan, F. Koczot, and A.J. Shatkin, "Genetic relatedness studies with adenovirus-associated viruses," 1968, *J. Virol.*, 2:999-1005.

Rosenfeld et al., "Adeno-associated viral vector gene transfer into leptomeningeal xenografts," 1997, *J Neuro-Oncology*, 34(2):139-144.

Russell et al., "Adeno-Associated Virus Vectors Preferentially Transduce Cells in S Phase," 1994, *Proc. Natl. Acad. Sci USA*, 91:8915-8919.

Rutledge EA, Halbert CL, and Russell DW, "Infectious Clones and Vectors Derived from Adeno-Associated Virus (AAV) Serotypes other Than AAV Type 2," 1998, *J. Virol.*, 72(1):309-319.

Ryan, J.H., S. Zolotukhin, and N. Muzyczka, "Sequence requirements for binding of Rep68 to the adeno-associated virus terminal repeats," 1996, *J. Virol.*, 70:1542-1553.

Rzadzinska, A. K., M. E. Schneider, et al., "An actin molecular treadmill and myosins maintain stereocilia functional architecture and self-renewal," 2004, *J Cell Biol*, 164(6):887-897.

Saffer, L. D., R. Gu, et al., "An RT-PCR analysis of mRNA for growth factor receptors in damaged and control sensory epithelia of rat utricles," 1996, *Hear Res*, 94(1-2):14-23.

Samulski RJ, Chang LS, Shenk T, "Helper-free stocks of recombinant adeno-associated viruses: normal integration does not require viral gene expression," 1989, *J Virol.*, 63(9):3822-3828, XP000283071.

Samulski, R. J., and T. Shenk, "Adenovirus E1B 55-$M_r$ polypeptide facilitates timely cytoplasmic accumulation of adeno-associated virus mRNAs," 1988, *J Virol*, 62:206-210.

Samulski, R.J., K.I. Berns, M. Tan, and N. Muzyczka, "Cloning of adeno-associated virus into pBR322: rescue of intact virus from the recombinant plasmid in human cells," 1982, *Proc Natl Acad Sci USA*, 79:2077-2081.

Sanes JR, JLR Rubenstein, and JF Nicolas, "Use of a recombinant retrovirus to study post-implantation cell lineage inmouse embryos," 1986, *EMBO J*, 5:3133-3142.

Sanlioglu, S., Benson, P.K., Yang, J., Atkinson, E.M., Reynolds, T. and Engelhardt, J.F., "Endocytosis and nuclear trafficking of adeno-associated virus type 2 are controlled by rac1 and phosphatidylinositol-3 kinase activation," 2000, *J Virol*, 74:9184-9196.

Schinkel AH, "P-Glycoprotein, a gatekeeper in the blood-brain barrier," 1999, *Adv Drug Deliv Rev*, 36:179-194.

Schlehofer JR, Heilbronn R, Georg-Fries B, zur Hausen H, "Inhibition of initiator-induced SV40 gene amplification in SV40-transformed Chinese hamster cells by infection with a defective parvovirus," 1983, *Int J Cancer*, 32(5):591-595, XP009010321.

Schlehofer, J. R., M. Ehrbar, and H. zur Hausen, "Vaccinia virus, herpes simplex virus, and carcinogens induce DNA amplification in a human cell line and support replication of a helpervirus dependent parvovirus," 1986, *Virology*, 152:110-117.

Schmidt M, Grot E, Cervenka P, Wainer S, Buck C, Chiorini JA, "Identification and characterization of novel adeno-associated virus isolates in ATCC virus stocks," 2006, *J Virol*, 80(10):5082-5085.

Schmidt et al., "Cloning and characterization of a bovine adeno-associated virus," 2004, *Journal of Virology*, 78(12):6509-6516, XP00233552.

Schneider, M. E., I. A. Belyantseva, et al., "Rapid renewal of auditory hair bundles," 2002, *Nature*, 418(6900):837-838.

Schwede, T., J. Kopp, N. Guex, and M. C. Peitsch, "SWISS-MODEL: An automated protein homology-modeling server," 2003, *Nucleic Acids Res*, 31:3381-3385.

Seiler MP, Miller AD, Zabner J, Halbert CL, "Adeno-associated virus types 5 and 6 use distinct receptors for cell entry," 2006, *Hum Gene Ther*, 17:10-19.

Seiler, M. P., C. L. Halbert, J. A. Chiorini, A. D. Miller, and J. Zabner, "AAV5 and AAV6 Mediate Gene Transfer to Human Airway Epthelia Via Different Receptors," 2002, *Mol Ther*, 5:S40.

Senapathy, P., J.D. Tratschin, and B.J. Carter, "Replication of adeno-associated virus DNA. Complementation of naturally occurring rep-mutants by a wild-type genome or an ori- mutant and correction of terminal palindrome deletions," 1984, *J Mol Biol* 179:1-20.

Shou, J., J. L. Zheng, et al., "Robust generation of new hair cells in the mature mammalian inner ear by adenoviral expression of Hath1," 2003, *Mol Cell Neurosci*, 23(2):169-179.

Smith, R. H., S.A. Afione et al., "Transposase-mediated construction of an integrated adeno-associated virus type 5 helper plasmid," 2002, *Biotechniques*, 33(1):204-206,208,210-211.

Snyder RO, Miao CH, Patijn GA, Spratt SK, Danos O., Nagy D., Gown AM, Winther B., Meuse L., Cohen LK, Thompson AR, and Kay MA, "Persistent and therapeutic concentrations of human factor IX in mice after hepatic gene transfer of recombinant AAV vectors," 1997, *Nat. Genet.*, 16:270-276.

Sobkowicz, H. M., J. M. Loftus, et al., "Tissue culture of the organ of Corti," 1993, *Acta Otolaryngol Suppl*, 502:3-36.

Staecker H, Li D, O'Malley BW Jr, Van De Water TR., "Gene expression in the mammalian cochlea: a study of multiple vector systems," 2001, *Acta Otolaryngol*, 121(2):157-163.

Stracker, T. H., G. D. Cassell, P. Ward, Y. M. Loo, B. van Breukelen, S. D. Carrington-Lawrence, R. K. Hamatake, P. C. van der Vliet, S. K. Weller, T. Melendy, and M. D. Weitzman, "The Rep protein of adeno-associated virus type 2 interacts with single-stranded DNA-binding proteins that enhance viral replication," 2004, *J Virol*, 78:441-453.

Summerford C, Bartlett JS, Samulski RJ., "*AlphaVbeta*5 integrin: a co-receptor for adeno-associated virus type 2 infection," 1999, *Nat Med*, 5(1):78-82.

Summerford, C. and R. J. Samulski, "Membrane-associated heparan sulfate proteoglycan is a receptor for adeno-associated virus type 2 virions," 1998, *J Virol*, 72(2):1438-1445.

Superti, F., M. L. Marziano, A. Tinari, and G. Donelli, "Effect of polyions on the infectivity of SA-11 rotavirus in LCC-MK2 cells," 1993, *Comp Immunol Microbiol Infect Dis*, 16:55-62.

Suzuki, H., Y. Katori, et al., "Carbohydrate distribution in the living utricular macula of the guinea pig detected by lectins," 1995, *Hear Res*, 87(1-2):32-40.

Teramoto, S., Bartlett JS, McCarty DXX, Samulski RJ, and Boucher RC, "Factors influencing adeno-associated virus-mediated gene transfer to human cystic fibrosis airway epithelial cells: comparison with adenovirus vectors," 1998, *J Virol*, 72:8904-8912.

Thomas CE, Storm TA, Huang Z, Kay MA, "Rapid uncoating of vector genomes is the key to efficient liver transduction with pseudotyped adeno-associated virus vectors," 2004, *J Virol*, 78(6):3110-3122.

Tratschin, J. D., M. H. West, T. Sandbank, and B. J. Carter, "A human parvovirus, adeno-associated virus, as a eucaryotic vector: transient expression and encapsidation of the procaryotic gene for chloramphenicol acetyltransferase," 1984, *Mol Cell Biol*, 4:2072-2081.

Tratschin, J.D., I.L. Miller, and B.J. Carter, "Genetic analysis of adeno-associated virus: properties of deletion mutants constructed in vitro and evidence for an adeno-associated virus replication function," 1984, *J. Virol.*, 51:611-619.

Trempe, J.P. and B.J. Carter, "Regulation of adeno-associated virus gene expression in 293 cells: control of mRNA abundance and translation," 1988, *J. Virol.*, 62:68-74.

Trempe, J.P., E. Mendelson, and B.J. Carter, "Characterization of adeno-associated virus rep proteins in human cells by antibodies raised against rep expressed in *Escherichia coli*," 1987, *Virology*, 161:18-28.

Tuma PL and Hubbard AL, "Transcytosis: crossing cellular barriers," 2003, *Physiol Rev*, 83(3):871-932.

Voutetakis A, Kok MR, Zheng C, Bossis I, Wang J, Cotrim AP, Marracino N, Goldsmith CM, Chiorini JA, Loh YP, Nieman LK, Baum BJ, "Reengineered salivary glands are stable endogenous bioreactors for systemic gene therapeutics," 2004, *Proc Natl Acad Sci USA*, 101(9):3053-3058.

Walsh, C.E., J.M. Liu, X. Xiao, N.S. Young, A.W. Nienhuis, and R.J. Samulski, "Regulated high level expression of a human gamma-globin gene introduced into erythroid cells by an adeno-associated virus vector," 1992, *Proc Natl Acad Sci USA*, 89:7257-7261.

Walters, R.W., Yi, S.M., Keshavjee, S., Brown, K.E., Welsh, M.J., Chiorini, J.A. and Zabner, J., "Binding of adeno-associated virus type 5 to 2,3-linked sialic acid is required for gene transfer," 2001, *J Biol Chem*, 276:20610-20616.

Walters, RW, Duan D., Engelhardt JF, and Welsh MJ., "Incorporation of adeno-associated virus in a calcium phosphate coprecipitate improves gene transfer to airway epithelia in vitro and in vivo," 2000, *J. Virol.*, 74:535-540.

Walters, RW, Grunst T., Bergelson JM, Finberg RW, Welsh MJ, and Zabner J., "Basolateral localization of fiber receptors limits adenovirus infection from the apical surface of airway epithelia," 1999, *J. Biol. Chem.*, 274:10219-10226.

Walz, C., A. Deprez, T. Dupressoir, M. Durst, M. Rabreau, and J. R. Schlehofer, "Interaction of human papillomavirus type 16 and adeno associated virus type 2 co-infecting human cervical epithelium," 1997, *J Gen Virol*, 78(Pt 6):1441-1452.

Wang G., Davidson BL, Melchert P., Slepushkin VA, van Es HH, Bodner M., Jolly DJ, and McCray PBJr., "Influence of cell polarity on retrovirus-mediated gene transfer to differentiated human airway epithelia," 1998, *Journal of Virology*, 72:9818-9826.

Wang, X. S., and A. Srivastava, "Rescue and autonomous replication of adeno-associated virus type 2 genomes containing Rep-binding site mutations in the viral p5 promoter," 1998, *J Virol*, 72:4811-4818.

Ward, P., F. B. Dean, M. E. O'Donnell, and K. I. Berns, "Role of the adenovirus DNA-binding protein in in vitro adeno-associated virus DNA replication," 1998, *J Virol*, 72:420-427.

Weindler, F. W., and R. Heilbronn, "A subset of herpes simplex virus replication genes provides helper functions for productive adeno-associated virus replication," 1991, *J Virol*, 65:2476-2483.

Winocour, E., M.F. Callaham, and E. Huberman, "Perturbation of the cell cycle by adeno-associated virus," 1988, *Virology*, 167:393-399.

Xiao, W., N. Chirmule, S. C. Berta, B. McCullough, G. Gao, and J. M. Wilson, "Gene therapy vectors based on adeno-associated virus type 1," 1999, *J Virol*, 73:3994-4003.

Xiao et al., "Efficient Long-Term Gene Transfer into Muscle Tissue of Immunocompetent Mice by Adeno-Associated Virus Vector," 1996, *J. Virol.*, 70(11):8098-8108.

Xiao Xm Li J, Samulski RJ, "Production of High-Titer Recombinant Adeno-Associated Virus Vectors in the Absence of Helper Adenovirus," 1997, *J Virol*, 72(3):2224-2232.

Xie Q. and Chapman MS, "Canine parvovirus capsid structure, analyzed at 2.9 Å resolution," 1996, *J Mol Biol*, 264:497-520.

Yalkinoglu, A.O., Heilbronn, R., Burkle, A., Schlehofer, J.R. and zur Hausen, H., "DNA amplification of adeno-associated virus as a response to cellular genotoxic stress," 1988, *Cancer Res*, 48:3123-3129.

Yakobson, B., Hrynko, T.A., Peak, M.J. and Winocour, E., "Replication of adeno-associated virus in cells irradiated with UV light at 254 nm," 1989, *J Virol*, 63:1023-1030.

Yamano, S., Huang, L.Y., Ding, C., Chiorini, J.A., Goldsmith, C.M., Wellner, R.B., Golding, B., Kotin, R.M., Scott, D.E. and Baum, B.J., "Recombinant adeno-associated virus serotype 2 vectors mediate stable interleukin 10 secretion from salivary glands into the bloodstream," 2002, *Hum Gene Ther*, 13:287-298.

Yamaya, M., Finkbeiner WE, Chun SY, and Widdicombe JH, "Differentiated structure and function of cultures from human tracheal epithelium," 1992, *Am.J.Physiol*, 262:L713-L724.

Zabner J, Seiler M, Walters R, Kotin RM, Fulgeras W, Davidson BL, Chiorini JA, "Adeno-associated virus type 5 (AAV5) but not AAV2 binds to the apical surfaces of airway epithelia and facilitates gene transfer," 2000, *J Virol.*, 74(8):3852-3858, XP002197205.

Zabner, J., Zeiher BG, Friedman E, and Welsh MJ, "Adenovirus-mediated gene transfer to ciliated airway epithelia requires prolonged incubation time," 1996, *J.Virol.*, 70:6994-7003.

Zhang JR, Mostov KE, Lamm ME, Nanno M, Shimida S, Ohwaki M, Tuomanen E, "The polymeric immunoglobulin receptor translocates pneumococci across human nasopharyngeal epithelial cells," 2000, *Cell*, 102(6):827-837.

Zhu ZB, Makhija SK, Lu B, Wang M, Rivera AA, Preuss M, Zhou F, Siegal GP, Alvarez RD, Curiel DT, "Transport across a polarized monolayer of Caco-2 cells by transferrin receptor-mediated adenovirus transcytosis," 2004, *Virol*, 325:116-128.

Zolotukhin et al., "Recombinant Adeno-Associated Virus Purification using Novel Methods Improves Infectious Titer and Yield," 1999, *Gene Ther*, 6:973-985.

Rudinger, J., "Characteristics of the amino acids as components of a peptide hormone sequence", in Peptide Hormones, University Park Press: Baltimore, MD, pp. 1-7, 1976.

Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-495.

Berns, K.I., (1996) Parvoviridae: The viruses and their replication. In *Fields Virology*, 3rd ed., pp. 2173-2197. Edited by B.N. Fields, D.M. Knipe & P.M. Howley. Philadelphia: Lipincott-Raven.

GenBank Accession No. AY186198, Jun. 5, 2003.

\* cited by examiner

```
                    ↓
GGCCGAGTGAGTGAGGCGAGCGCGCATAGAGGGAGTGGCCAA          GGGTAGTAGATCCAAACGGG
|||||||||||||||||||||  |||||||||||||||||||          ||||||||||||||||||||
CCGGCTCACTCACTCGCGCTCG CGCGTATCTCCCTCACCGGTT        GAGGTAGTAGATCCAAACGGG
```

FIG. 2

SEQUENCE LISTING

<160> NUMBER OF SEQ ID NOS: 22

<210> SEQ ID NO 1
<211> LENGTH: 4768
<212> TYPE: DNA
<213> ORGANISM: adeno-associated virus 4

```
<220> FEATURE:
<221> NAME/KEY: misc_feature
<223> OTHER INFORMATION: AAV4 genome
<220> FEATURE:
<221> NAME/KEY: misc_feature
<222> LOCATION: (3009)..(3009)
<223> OTHER INFORMATION: n = unknown

<400> SEQUENCE: 1
ttggccactc cctctatgcg cgctcgctca ctcactcggc cctggagacc aaaggtctcc      60
agactgccgg cctctggccg gcagggccga gtgagtgagc gagcgcgcat agagggagtg     120
gccaactcca tcatctaggt ttgcccactg acgtcaatgt gacgtcctag ggttagggag     180
gtccctgtat tagcagtcac gtgagtgtcg tatttcgcgg agcgtagcgg agcgcatacc     240
aagctgccac gtcacagcca cgtggtccgt ttgcgacagt ttgcgacacc atgtggtcag     300
gagggtatat aaccgcgagt gagccagcga ggagctccat tttgcccgcg aattttgaac     360
gagcagcagc catgccgggg ttctacgaga tcgtgctgaa ggtgcccagc gacctggacg     420
agcacctgcc cggcatttct gactcttttg tgagctgggt ggccgagaag gaatgggagc     480
tgccgccgga ttctgacatg gacttgaatc tgattgagca ggcacccctg accgtggccg     540
aaaagctgca acgcgagttc ctggtcgagt ggcgccgcgt gagtaaggcc ccggaggccc     600
tcttctttgt ccagttcgag aaggggggaca gctacttcca cctgcacatc ctggtggaga     660
ccgtgggcgt caaatccatg gtggtgggcc gctacgtgag ccagattaaa gagaagctgg     720
tgacccgcat ctaccgcggg gtcgagccga gcttccgaa ctggttcgcg gtgaccaaga     780
cgcgtaatgg cgccggaggc gggaacaagg tggtggacga ctgctacatc cccaactacc     840
tgctccccaa gacccagccc gagctccagt gggcgtggac taacatggac cagtatataa     900
gcgcctgttt gaatctcgcg gagcgtaaac ggctggtggc gcagcatctg acgcacgtgt     960
cgcagacgca ggagcagaac aaggaaaaac agaaccccaa ttctgacgcg ccggtcatca    1020
ggtcaaaaac ctccgccagg tacatggagc tggtcgggtg gctggtggac cgcgggatca    1080
cgtcagaaaa gcaatggatc caggaggacc aggcgtccta catctccttc aacgccgcct    1140
ccaactcgcg gtcacaaatc aaggccgcgc tggacaatgc ctccaaaatc atgagcctga    1200
caaagacggc tccggactac ctggtgggcc agaacccgcc ggaggacatt tccagcaacc    1260
gcatctaccg aatcctcgag atgaacgggt acgatccgca gtacgcggcc tccgtcttcc    1320
tgggctgggc gcaaaagaag ttcgggaaga ggaacaccat ctggctcttt gggccggcca    1380
cgacgggtaa aaccaacatc gcggaagcca tcgcccacgc cgtgcccttc tacgctgcg     1440 tgaactggac caatgagaac tttccgttca acgattgcgt cgacaagatg gtgatctggt    1500
gggaggaggg caagatgacg gccaaggtcg tagagagcgc caaggccatc ctgggcggaa    1560
gcaaggtgcg cgtggaccaa aagtgcaagt catcggccca gatcgaccca actcccgtga    1620
tcgtcacctc caacaccaac atgtgcgcgg tcatcgacgg aaactcgacc accttcgagc    1680
accaacaacc actccaggac cggatgttca gttcgagct caccaagcgc ctggagcacg    1740
actttggcaa ggtcaccaag caggaagtca aagacttttt ccgtgggcg tcagatcacg    1800 tgaccgaggt gactcacgag ttttacgtca gaaagggtgg agctagaaag aggcccgccc    1860
ccaatgacgc agatataagt gagcccaagc gggcctgtcc gtcagttgcg cagccatcga    1920
cgtcagacgc ggaagctccg gtggactacg cggacaggta ccaaaacaaa tgttctcgtc    1980
acgtgggtat gaatctgatg ctttttcct gccggcaatg cgagagaatg aatcagaatg    2040
tggacatttg cttcacgcac gggtcatgg actgtgccga gtgcttcccc gtgtcagaat    2100
```

```
ctcaacccgt gtctgtcgtc agaaagcgga cgtatcagaa actgtgtccg attcatcaca    2160
tcatggggag ggcgcccgag gtggcctgct cggcctgcga actggccaat gtggacttgg    2220
atgactgtga catggaacaa taaatgactc aaaccagata tgactgacgg ttaccttcca    2280
gattggctag aggacaacct ctctgaaggc gttcgagagt ggtgggcgct gcaacctgga    2340
gcccctaaac ccaaggcaaa tcaacaacat caggacaacg ctcggggtct tgtgcttccg    2400
ggttacaaat acctcggacc cggcaacgga ctcgacaagg ggaacccgt  caacgcagcg    2460
gacgcggcag ccctcgagca cgacaaggcc tacgaccagc agctcaaggc cggtgacaac    2520
ccctacctca gtacaaccca cgccgacgcg gagttccagc agcggcttca gggcgacaca    2580
ccgtttgggg gcaacctcgg cagagcagtc ttccaggcca aaagagggt  tcttgaacct    2640
cttggtctgg ttgagcaagc gggtgagacg gctcctggaa agaagagacc gttgattgaa    2700
tccccccagc agcccgactc ctccacgggt atcggcaaaa aaggcaagca gccggctaaa    2760
aagaagctcg ttttcgaaga cgaaactgga gcaggcgacg gacccccctga gggatcaact    2820
tccggagcca tgtctgatga cagtgagatg cgtgcagcag ctggcggagc tgcagtcgag    2880
ggsggacaag gtgccgatgg agtgggtaat gcctcgggtg attggcattg cgattccacc    2940
tggtctgagg gccacgtcac gaccaccagc accagaacct gggtcttgcc cacctacaac    3000
aaccacctnt acaagcgact cggagagagc ctgcagtcca cacctacaa  cggattctcc    3060
acccctggg  gatactttga cttcaaccgc ttccactgcc acttctcacc acgtgactgg    3120
cagcgactca tcaacaacaa ctggggcatg cgacccaaag ccatgcgggt caaaatcttc    3180
aacatccagg tcaaggaggt cacgacgtcg aacggcgaga caacggtggc taataaccttt   3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
tgcctggagt actttccttc gcagatgctg cggactggca caactttga  aattacgtac    3480
agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga actggctgcc cgggccttca atcaagcagc agggcttctc aaagactgcc    3720
aatcaaaact acaagatccc tgccaccggg tcagacagtc tcatcaaata cgagacgcac    3780
agcactctgg acgaagatg  gagtgccctg acccccggac ctccaatggc cacggctgga    3840
cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg gtgaccagag caacagcaac    4020
ctgccgaccg tggacagact gacagccttg ggagccgtgc ctggaatggt ctggcaaaac    4080
agagacattt actaccaggg tcccatttgg gccaagattc ctcataccga tggacacttt    4140
caccccctcac cgctgattgg tgggtttggg ctgaaacacc cgcctcctca aattttatc    4200
aagaacaccc cggtacctgc gaatcctgca acgaccttca gctctactcc ggtaaactcc    4260
ttcattactc agtacagcac tggccaggtg tcggtcagaa ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctaggc  tatcggtacc    4440
cgctacctca cccaccacct gtaataaccct gttaatcaat aaaccggttt attcgtttca    4500
```

-continued

```
gttgaactttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac catgatgatg gagttggcca ctccctctat gcgcgctcgc tcactcactc    4680
ggccctggag accaaaggtc tccagactgc cggcctctgg ccggcagggc cgagtgagtg    4740
agcgagcgcg catagaggga gtggccaa                                      4768
```

<210> SEQ ID NO 2
<211> LENGTH: 623
<212> TYPE: PRT
<213> ORGANISM: adeno-associated virus 4
<220> FEATURE:
<221> NAME/KEY: MISC_FEATURE
<223> OTHER INFORMATION: AAV4 Rep protein (full length)

<400> SEQUENCE: 2

```
Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Gln Asn
        275                 280                 285

Pro Pro Glu Asp Ile Ser Ser Asn Arg Ile Tyr Arg Ile Leu Glu Met
    290                 295                 300

Asn Gly Tyr Asp Pro Gln Tyr Ala Ala Ser Val Phe Leu Gly Trp Ala
305                 310                 315                 320
```

```
Gln Lys Lys Phe Gly Lys Arg Asn Thr Ile Trp Leu Phe Gly Pro Ala
            325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Lys Arg Leu Glu His Asp Phe Gly Lys Val Thr Lys Gln
            450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
            485                 490                 495

Pro Asn Asp Ala Asp Ile Ser Glu Pro Lys Arg Ala Cys Pro Ser Val
            500                 505                 510

Ala Gln Pro Ser Thr Ser Asp Ala Glu Ala Pro Val Asp Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
            565                 570                 575

Ser Gln Pro Val Ser Val Val Arg Lys Arg Thr Tyr Gln Lys Leu Cys
            580                 585                 590

Pro Ile His His Ile Met Gly Arg Ala Pro Glu Val Ala Cys Ser Ala
            595                 600                 605

Cys Glu Leu Ala Asn Val Asp Leu Asp Asp Cys Asp Met Glu Gln
    610                 615                 620

<210> SEQ ID NO 3
<211> LENGTH: 1872
<212> TYPE: DNA
<213> ORGANISM: adeno-associated virus 4
<220> FEATURE:
<221> NAME/KEY: misc_feature
<223> OTHER INFORMATION: AAV4 Rep gene (full length)
<220> FEATURE:
<221> NAME/KEY: exon
<222> LOCATION: (1)..(1872)

<400> SEQUENCE: 3 atg ccg ggg ttc tac gag atc gtg ctg aag gtg ccc agc gac ctg gac    48
Met Pro Gly Phe Tyr Glu Ile Val Leu Lys Val Pro Ser Asp Leu Asp
1               5                   10                  15 gag cac ctg ccc ggc att tct gac tct ttt gtg agc tgg gtg gcc gag    96
Glu His Leu Pro Gly Ile Ser Asp Ser Phe Val Ser Trp Val Ala Glu
            20                  25                  30
```

-continued

| | |
|---|---|
| aag gaa tgg gag ctg ccg ccg gat tct gac atg gac ttg aat ctg att<br>Lys Glu Trp Glu Leu Pro Pro Asp Ser Asp Met Asp Leu Asn Leu Ile<br>35                           40                        45 | 144 |
| gag cag gca ccc ctg acc gtg gcc gaa aag ctg caa cgc gag ttc ctg<br>Glu Gln Ala Pro Leu Thr Val Ala Glu Lys Leu Gln Arg Glu Phe Leu<br>50                           55                       60 | 192 |
| gtc gag tgg cgc cgc gtg agt aag gcc ccg gag gcc ctc ttc ttt gtc<br>Val Glu Trp Arg Arg Val Ser Lys Ala Pro Glu Ala Leu Phe Phe Val<br>65                         70                       75                       80 | 240 |
| cag ttc gag aag ggg gac agc tac ttc cac ctg cac atc ctg gtg gag<br>Gln Phe Glu Lys Gly Asp Ser Tyr Phe His Leu His Ile Leu Val Glu<br>                       85                       90                       95 | 288 |
| acc gtg ggc gtc aaa tcc atg gtg gtg ggc cgc tac gtg agc cag att<br>Thr Val Gly Val Lys Ser Met Val Val Gly Arg Tyr Val Ser Gln Ile<br>                     100                    105                    110 | 336 |
| aaa gag aag ctg gtg acc cgc atc tac cgc ggg gtc gag ccg cag ctt<br>Lys Glu Lys Leu Val Thr Arg Ile Tyr Arg Gly Val Glu Pro Gln Leu<br>115                       120                    125 | 384 |
| ccg aac tgg ttc gcg gtg acc aag acg cgt aat ggc gcc gga ggc ggg<br>Pro Asn Trp Phe Ala Val Thr Lys Thr Arg Asn Gly Ala Gly Gly Gly<br>130                       135                    140 | 432 |
| aac aag gtg gtg gac gac tgc tac atc ccc aac tac ctg ctc ccc aag<br>Asn Lys Val Val Asp Asp Cys Tyr Ile Pro Asn Tyr Leu Leu Pro Lys<br>145                     150                    155                  160 | 480 |
| acc cag ccc gag ctc cag tgg gcg tgg act aac atg gac cag tat ata<br>Thr Gln Pro Glu Leu Gln Trp Ala Trp Thr Asn Met Asp Gln Tyr Ile<br>                     165                    170                    175 | 528 |
| agc gcc tgt ttg aat ctc gcg gag cgt aaa cgg ctg gtg gcg cag cat<br>Ser Ala Cys Leu Asn Leu Ala Glu Arg Lys Arg Leu Val Ala Gln His<br>                     180                    185                    190 | 576 |
| ctg acg cac gtg tcg cag acg cag gag cag aac aag gaa aac cag aac<br>Leu Thr His Val Ser Gln Thr Gln Glu Gln Asn Lys Glu Asn Gln Asn<br>                     195                    200                    205 | 624 |
| ccc aat tct gac gcg ccg gtc atc agg tca aaa acc tcc gcc agg tac<br>Pro Asn Ser Asp Ala Pro Val Ile Arg Ser Lys Thr Ser Ala Arg Tyr<br>210                       215                    220 | 672 |
| atg gag ctg gtc ggg tgg ctg gtg gac cgc ggg atc acg tca gaa aag<br>Met Glu Leu Val Gly Trp Leu Val Asp Arg Gly Ile Thr Ser Glu Lys<br>225                     230                    235                  240 | 720 |
| caa tgg atc cag gag gac cag gcg tcc tac atc tcc ttc aac gcc gcc<br>Gln Trp Ile Gln Glu Asp Gln Ala Ser Tyr Ile Ser Phe Asn Ala Ala<br>                     245                    250                    255 | 768 |
| tcc aac tcg cgg tca caa atc aag gcc gcg ctg gac aat gcc tcc aaa<br>Ser Asn Ser Arg Ser Gln Ile Lys Ala Ala Leu Asp Asn Ala Ser Lys<br>                     260                    265                    270 | 816 |
| atc atg agc ctg aca aag acg gct ccg gac tac ctg gtg ggc cag aac<br>Ile Met Ser Leu Thr Lys Thr Ala Pro Asp Tyr Leu Val Gly Gln Asn<br>275                       280                    285 | 864 |
| ccg ccg gag gac att tcc agc aac cgc atc tac cga atc ctc gag atg<br>Pro Pro Glu Asp Ile Ser Ser Asn Arg Ile Tyr Arg Ile Leu Glu Met<br>290                       295                    300 | 912 |
| aac ggg tac gat ccg cag tac gcg gcc tcc gtc ttc ctg ggc tgg gcg<br>Asn Gly Tyr Asp Pro Gln Tyr Ala Ala Ser Val Phe Leu Gly Trp Ala<br>305                     310                    315                  320 | 960 |
| caa aag aag ttc ggg aag agg aac acc atc tgg ctc ttt ggg ccg gcc<br>Gln Lys Lys Phe Gly Lys Arg Asn Thr Ile Trp Leu Phe Gly Pro Ala<br>                     325                    330                    335 | 1008 |
| acg acg ggt aaa acc aac atc gcg gaa gcc atc gcc cac gcc gtg ccc<br>Thr Thr Gly Lys Thr Asn Ile Ala Glu Ala Ile Ala His Ala Val Pro<br>340                       345                    350 | 1056 |

| | | | | | | | | | | | | | | | | |
|---|---|---|---|---|---|---|---|---|---|---|---|---|---|---|---|---|
| ttc | tac | ggc | tgc | gtg | aac | tgg | acc | aat | gag | aac | ttt | ccg | ttc | aac | gat | 1104 |
| Phe | Tyr | Gly | Cys | Val | Asn | Trp | Thr | Asn | Glu | Asn | Phe | Pro | Phe | Asn | Asp | |
| | | 355 | | | | 360 | | | | 365 | | | | | | |
| tgc | gtc | gac | aag | atg | gtg | atc | tgg | tgg | gag | gag | ggc | aag | atg | acg | gcc | 1152 |
| Cys | Val | Asp | Lys | Met | Val | Ile | Trp | Trp | Glu | Glu | Gly | Lys | Met | Thr | Ala | |
| | 370 | | | | 375 | | | | 380 | | | | | | | |
| aag | gtc | gta | gag | agc | gcc | aag | gcc | atc | ctg | ggc | gga | agc | aag | gtg | cgc | 1200 |
| Lys | Val | Glu | Ser | Ala | Lys | Ala | Ile | Leu | Gly | Gly | Ser | Lys | Val | Arg | | |
| 385 | | | | 390 | | | | | 395 | | | | | 400 | | |
| gtg | gac | caa | aag | tgc | aag | tca | tcg | gcc | cag | atc | gac | cca | act | ccc | gtg | 1248 |
| Val | Asp | Gln | Lys | Cys | Lys | Ser | Ser | Ala | Gln | Ile | Asp | Pro | Thr | Pro | Val | |
| | | | 405 | | | | | 410 | | | | | 415 | | | |
| atc | gtc | acc | tcc | aac | acc | aac | atg | tgc | gcg | gtc | atc | gac | gga | aac | tcg | 1296 |
| Ile | Val | Thr | Ser | Asn | Thr | Asn | Met | Cys | Ala | Val | Ile | Asp | Gly | Asn | Ser | |
| | | 420 | | | | | 425 | | | | | 430 | | | | |
| acc | acc | ttc | gag | cac | caa | caa | cca | ctc | cag | gac | cgg | atg | ttc | aag | ttc | 1344 |
| Thr | Thr | Phe | Glu | His | Gln | Gln | Pro | Leu | Gln | Asp | Arg | Met | Phe | Lys | Phe | |
| | 435 | | | | | 440 | | | | | 445 | | | | | |
| gag | ctc | acc | aag | cgc | ctg | gag | cac | gac | ttt | ggc | aag | gtc | acc | aag | cag | 1392 |
| Glu | Leu | Thr | Lys | Arg | Leu | Glu | His | Asp | Phe | Gly | Lys | Val | Thr | Lys | Gln | |
| 450 | | | | | 455 | | | | | 460 | | | | | | |
| gaa | gtc | aaa | gac | ttt | ttc | cgg | tgg | gcg | tca | gat | cac | gtg | acc | gag | gtg | 1440 |
| Glu | Val | Lys | Asp | Phe | Phe | Arg | Trp | Ala | Ser | Asp | His | Val | Thr | Glu | Val | |
| 465 | | | | 470 | | | | | 475 | | | | | 480 | | |
| act | cac | gag | ttt | tac | gtc | aga | aag | ggt | gga | gct | aga | aag | agg | ccc | gcc | 1488 |
| Thr | His | Glu | Phe | Tyr | Val | Arg | Lys | Gly | Gly | Ala | Arg | Lys | Arg | Pro | Ala | |
| | | | 485 | | | | | 490 | | | | | 495 | | | |
| ccc | aat | gac | gca | gat | ata | agt | gag | ccc | aag | cgg | gcc | tgt | ccg | tca | gtt | 1536 |
| Pro | Asn | Asp | Ala | Asp | Ile | Ser | Glu | Pro | Lys | Arg | Ala | Cys | Pro | Ser | Val | |
| | | | 500 | | | | | 505 | | | | | 510 | | | |
| gcg | cag | cca | tcg | acg | tca | gac | gcg | gaa | gct | ccg | gtg | gac | tac | gcg | gac | 1584 |
| Ala | Gln | Pro | Ser | Thr | Ser | Asp | Ala | Glu | Ala | Pro | Val | Asp | Tyr | Ala | Asp | |
| | | 515 | | | | | 520 | | | | | 525 | | | | |
| agg | tac | caa | aac | aaa | tgt | tct | cgt | cac | gtg | ggt | atg | aat | ctg | atg | ctt | 1632 |
| Arg | Tyr | Gln | Asn | Lys | Cys | Ser | Arg | His | Val | Gly | Met | Asn | Leu | Met | Leu | |
| 530 | | | | | 535 | | | | | 540 | | | | | | |
| ttt | ccc | tgc | cgg | caa | tgc | gag | aga | atg | aat | cag | aat | gtg | gac | att | tgc | 1680 |
| Phe | Pro | Cys | Arg | Gln | Cys | Glu | Arg | Met | Asn | Gln | Asn | Val | Asp | Ile | Cys | |
| 545 | | | | 550 | | | | | 555 | | | | | 560 | | |
| ttc | acg | cac | ggg | gtc | atg | gac | tgt | gcc | gag | tgc | ttc | ccc | gtg | tca | gaa | 1728 |
| Phe | Thr | His | Gly | Val | Met | Asp | Cys | Ala | Glu | Cys | Phe | Pro | Val | Ser | Glu | |
| | | | | 565 | | | | | 570 | | | | | 575 | | |
| tct | caa | ccc | gtg | tct | gtc | gtc | aga | aag | cgg | acg | tat | cag | aaa | ctg | tgt | 1776 |
| Ser | Gln | Pro | Val | Ser | Val | Val | Arg | Lys | Arg | Thr | Tyr | Gln | Lys | Leu | Cys | |
| | | | 580 | | | | | 585 | | | | | 590 | | | |
| ccg | att | cat | cac | atc | atg | ggg | agg | gcg | ccc | gag | gtg | gcc | tgc | tcg | gcc | 1824 |
| Pro | Ile | His | His | Ile | Met | Gly | Arg | Ala | Pro | Glu | Val | Ala | Cys | Ser | Ala | |
| | | 595 | | | | | 600 | | | | | 605 | | | | |
| tgc | gaa | ctg | gcc | aat | gtg | gac | ttg | gat | gac | tgt | gac | atg | gaa | caa | taa | 1872 |
| Cys | Glu | Leu | Ala | Asn | Val | Asp | Leu | Asp | Asp | Cys | Asp | Met | Glu | Gln | | |
| | 610 | | | | 615 | | | | | 620 | | | | | | |

<210> SEQ ID NO 4
<211> LENGTH: 734
<212> TYPE: PRT
<213> ORGANISM: adeno-associated virus 4
<220> FEATURE:
<221> NAME/KEY: MISC_FEATURE
<223> OTHER INFORMATION: AAV4 capsid protein vp1

<400> SEQUENCE: 4

Met Thr Asp Gly Tyr Leu Pro Asp Trp Leu Glu Asp Asn Leu Ser Glu

```
         1               5              10              15
Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
                35                  40                  45

Tyr Lys Tyr Leu Gly Pro Gly Asn Gly Leu Asp Lys Gly Glu Pro Val
                50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
                100                 105                 110

Leu Gly Arg Ala Val Phe Gln Ala Lys Lys Arg Val Leu Glu Pro Leu
                115                 120                 125

Gly Leu Val Glu Gln Ala Gly Glu Thr Ala Pro Gly Lys Lys Arg Pro
                130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
                180                 185                 190

Asp Asp Ser Glu Met Arg Ala Ala Ala Gly Gly Ala Ala Val Glu Gly
                195                 200                 205

Gly Gln Gly Ala Asp Gly Val Gly Asn Ala Ser Gly Asp Trp His Cys
                210                 215                 220

Asp Ser Thr Trp Ser Glu Gly His Val Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
                275                 280                 285

Arg Leu Ile Asn Asn Asn Trp Gly Met Arg Pro Lys Ala Met Arg Val
                290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
                340                 345                 350

Leu Pro Pro Phe Pro Asn Asp Val Phe Met Val Pro Gln Tyr Gly Tyr
                355                 360                 365

Cys Gly Leu Val Thr Gly Asn Thr Ser Gln Gln Gln Thr Asp Arg Asn
                370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
                420                 425                 430
```

Asp Gln Tyr Leu Trp Gly Leu Gln Ser Thr Thr Gly Thr Thr Leu
    435                 440                 445

Asn Ala Gly Thr Ala Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
                580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 5
<211> LENGTH: 2208
<212> TYPE: DNA
<213> ORGANISM: adeno-associated virus 4
<220> FEATURE:
<221> NAME/KEY: misc_feature
<223> OTHER INFORMATION: AAV4 capsid protein vp1 gene
<220> FEATURE:
<221> NAME/KEY: misc_feature
<222> LOCATION: (750)..(750)
<223> OTHER INFORMATION: n = unknown

<400> SEQUENCE: 5
atgactgacg gttaccttcc agattggcta gaggacaacc tctctgaagg cgttcgagag    60
tggtgggcgc tgcaacctgg agcccctaaa cccaaggcaa atcaacaaca tcaggacaac   120
gctcggggtc ttgtgcttcc gggttacaaa tacctcggac ccggcaacgg actcgacaag   180
ggggaacccg tcaacgcagc ggacgcggca gccctcgagc acgacaaggc ctacgaccag   240

```
cagctcaagg ccggtgacaa ccccctacctc aagtacaacc acgccgacgc ggagttccag    300
cagcggcttc agggcgacac atcgtttggg ggcaacctcg gcagagcagt cttccaggcc    360
aaaaagaggg ttcttgaacc tcttggtctg gttgagcaag cgggtgagac ggctcctgga    420
aagaagagac cgttgattga atcccccag cagcccgact cctccacggg tatcggcaaa     480
aaaggcaagc agccggctaa aagaagctc gttttcgaag acgaaactgg agcaggcgac     540
ggaccccctg agggatcaac ttccggagcc atgtctgatg acagtgagat gcgtgcagca    600
gctggcggag ctgcagtcga gggsggacaa ggtgccgatg gagtgggtaa tgcctcgggt    660
gattggcatt gcgattccac ctggtctgag ggccacgtca cgaccaccag caccagaacc    720
tgggtcttgc ccacctacaa caaccacctn tacaagcgac tcggagagag cctgcagtcc    780
aacacctaca acggattctc cacccctgg ggatactttg acttcaaccg cttccactgc    840
cacttctcac cacgtgactg gcagcgactc atcaacaaca actggggcat gcgacccaaa    900
gccatgcggg tcaaaatctt caacatccag gtcaaggagg tcacgacgtc gaacggcgag    960
acaacggtgg ctaataacct taccagcacg gttcagatct ttgcggactc gtcgtacgaa   1020
ctgccgtacg tgatggatgc gggtcaagag ggcagcctgc ctccttttcc caacgacgtc   1080
tttatggtgc cccagtacgg ctactgtgga ctggtgaccg gcaacacttc gcagcaacag   1140
actgacagaa atgccttcta ctgcctggag tactttcctt cgcagatgct gcggactggc   1200
aacaactttg aaattacgta cagttttgag aaggtgcctt tccactcgat gtacgcgcac   1260
agccagagcc tggaccggct gatgaaccct ctcatcgacc agtacctgtg gggactgcaa   1320
tcgaccacca ccggaaccac cctgaatgcc gggactgcca ccaccaactt taccaagctg   1380
cggcctacca actttttccaa ctttaaaaag aactggctgc ccgggccttc aatcaagcag   1440
cagggcttct caaagactgc caatcaaaac tacaagatcc ctgccaccgg gtcagacagt   1500
ctcatcaaat acgagacgca cagcactctg acggaagat ggagtgccct gacccccgga   1560
cctccaatgg ccacggctgg acctgcggac agcaagttca gcaacagcca gctcatctttt  1620 gcggggccta acagaacgg caacacggcc accgtacccg ggactctgat cttcacctct   1680
gaggaggagc tggcagccac caacgccacc gatacggaca tgtggggcaa cctacctggc   1740
ggtgaccaga gcaacagcaa cctgccgacc gtggacagac tgacagcctt gggagccgtg   1800
cctggaatgg tctggcaaaa cagagacatt tactaccagg gtcccatttg gccaagatt    1860 cctcataccg atggacactt tcaccccctca ccgctgattg gtgggtttgg gctgaaacac   1920
ccgcctcctc aaatttttat caagaacacc ccggtacctg cgaatcctgc aacgaccttc   1980
agctctactc cggtaaactc cttcattact cagtacagca ctggccaggt gtcggtgcag   2040
attgactggg agatccagaa ggagcggtcc aaacgctgga accccgaggt ccagtttacc   2100
tccaactacg gacagcaaaa ctctctgttg tgggctcccg atgcggctgg gaaatacact   2160
gagcctaggg ctatcggtac ccgctacctc acccaccacc tgtaataa                2208
```

<210> SEQ ID NO 6
<211> LENGTH: 125
<212> TYPE: DNA
<213> ORGANISM: adeno-associated virus 4
<220> FEATURE:
<221> NAME/KEY: misc_feature
<223> OTHER INFORMATION: AAV4 ITR "flip" orientation

<400> SEQUENCE: 6

```
ttggccactc cctctatgcg cgctcgctca ctcactcggc cctggagacc aaaggtctcc     60
agactgccgg cctctggccg gcagggccga gtgagtgagc gagcgcgcat agaggagtg    120
```

```
gccaa                                                              125

<210> SEQ ID NO 7
<211> LENGTH: 245
<212> TYPE: DNA
<213> ORGANISM: adeno-associated virus 4
<220> FEATURE:
<221> NAME/KEY: misc_feature
<223> OTHER INFORMATION: AAV4 p5 promoter

<400> SEQUENCE: 7
ctccatcatc taggtttgcc cactgacgtc aatgtgacgt cctagggtta gggaggtccc      60
tgtattagca gtcacgtgag tgtcgtattt cgcggagcgt agcggagcgc ataccaagct     120
gccacgtcac agccacgtgg tccgtttgcg acagtttgcg acaccatgtg gtcaggaggg     180
tatataaccg cgagtgagcc agcgaggagc tccattttgc ccgcgaattt tgaacgagca     240
gcagc                                                              245

<210> SEQ ID NO 8
<211> LENGTH: 313
<212> TYPE: PRT
<213> ORGANISM: adeno-associated virus 4
<220> FEATURE:
<221> NAME/KEY: MISC_FEATURE
<223> OTHER INFORMATION: AAV4 Rep protein 40
<220> FEATURE:
<221> NAME/KEY: MISC_FEATURE
<222> LOCATION: (313)..(313)
<223> OTHER INFORMATION: Xaa = unknown

<400> SEQUENCE: 8
```

Met Glu Leu Val Gly Trp Leu Val Asp Arg Gly Ile Thr Ser Glu Lys
1               5                  10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Gln Asn
    50                  55                  60

Pro Pro Glu Asp Ile Ser Ser Asn Arg Ile Tyr Arg Ile Leu Glu Met
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

```
Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
            245                 250                 255

Thr His Glu Phe Tyr Val Arg Lys Gly Gly Ala Arg Lys Arg Pro Ala
        260                 265                 270

Pro Asn Asp Ala Asp Ile Ser Glu Pro Lys Arg Ala Cys Pro Ser Val
    275                 280                 285

Ala Gln Pro Ser Thr Ser Asp Ala Glu Ala Pro Val Asp Tyr Ala Asp
    290                 295                 300

Arg Leu Ala Arg Gly Gln Pro Leu Xaa
305                 310

<210> SEQ ID NO 9
<211> LENGTH: 399
<212> TYPE: PRT
<213> ORGANISM: adeno-associated virus 4
<220> FEATURE:
<221> NAME/KEY: MISC_FEATURE
<223> OTHER INFORMATION: AAV4 Rep protein 52

<400> SEQUENCE: 9

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Gln Asn
    50                  55                  60

Pro Pro Glu Asp Ile Ser Ser Asn Arg Ile Tyr Arg Ile Leu Glu Met
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
            245                 250                 255

Thr His Glu Phe Tyr Val Arg Lys Gly Gly Ala Arg Lys Arg Pro Ala
        260                 265                 270
```

```
Pro Asn Asp Ala Asp Ile Ser Glu Pro Lys Arg Ala Cys Pro Ser Val
            275                 280                 285

Ala Gln Pro Ser Thr Ser Asp Ala Glu Ala Pro Val Asp Tyr Ala Asp
        290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Val Asp Ile Cys
                325                 330                 335

Phe Thr His Gly Val Met Asp Cys Ala Glu Cys Phe Pro Val Ser Glu
                340                 345                 350

Ser Gln Pro Val Ser Val Val Arg Lys Arg Thr Tyr Gln Lys Leu Cys
        355                 360                 365

Pro Ile His His Ile Met Gly Arg Ala Pro Glu Val Ala Cys Ser Ala
        370                 375                 380

Cys Glu Leu Ala Asn Val Asp Leu Asp Asp Cys Asp Met Glu Gln
385                 390                 395

<210> SEQ ID NO 10
<211> LENGTH: 537
<212> TYPE: PRT
<213> ORGANISM: adeno-associated virus 4
<220> FEATURE:
<221> NAME/KEY: MISC_FEATURE
<223> OTHER INFORMATION: AAV4 Rep protein 68
<220> FEATURE:
<221> NAME/KEY: MISC_FEATURE
<222> LOCATION: (537)..(537)
<223> OTHER INFORMATION: Xaa = unknown

<400> SEQUENCE: 10

Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
```

```
                210                 215                 220
Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
            260                 265                 270

Ile Met Ser Leu Thr Lys Thr Ala Pro Asp Tyr Leu Val Gly Gln Asn
        275                 280                 285

Pro Pro Glu Asp Ile Ser Ser Asn Arg Ile Tyr Arg Ile Leu Glu Met
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Lys Arg Leu Glu His Asp Phe Gly Lys Val Thr Lys Gln
450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
                485                 490                 495

Pro Asn Asp Ala Asp Ile Ser Glu Pro Lys Arg Ala Cys Pro Ser Val
            500                 505                 510

Ala Gln Pro Ser Thr Ser Asp Ala Glu Ala Pro Val Asp Tyr Ala Asp
        515                 520                 525

Arg Leu Ala Arg Gly Gln Pro Leu Xaa
    530                 535

<210> SEQ ID NO 11
<211> LENGTH: 623
<212> TYPE: PRT
<213> ORGANISM: adeno-associated virus 4
<220> FEATURE:
<221> NAME/KEY: MISC_FEATURE
<223> OTHER INFORMATION: AAV4 Rep protein 78

<400> SEQUENCE: 11

Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
```

```
                  35                  40                  45
Glu Gln Ala Pro Leu Thr Val Ala Glu Lys Leu Gln Arg Glu Phe Leu
 50                  55                  60
Val Glu Trp Arg Arg Val Ser Lys Ala Pro Glu Ala Leu Phe Phe Val
 65                  70                  75                  80
Gln Phe Glu Lys Gly Asp Ser Tyr Phe His Leu His Ile Leu Val Glu
                     85                  90                  95
Thr Val Gly Val Lys Ser Met Val Val Gly Arg Tyr Val Ser Gln Ile
                    100                 105                 110
Lys Glu Lys Leu Val Thr Arg Ile Tyr Arg Gly Val Glu Pro Gln Leu
                115                 120                 125
Pro Asn Trp Phe Ala Val Thr Lys Thr Arg Asn Gly Ala Gly Gly Gly
                130                 135                 140
Asn Lys Val Val Asp Asp Cys Tyr Ile Pro Asn Tyr Leu Leu Pro Lys
145                 150                 155                 160
Thr Gln Pro Glu Leu Gln Trp Ala Trp Thr Asn Met Asp Gln Tyr Ile
                    165                 170                 175
Ser Ala Cys Leu Asn Leu Ala Glu Arg Lys Arg Leu Val Ala Gln His
                180                 185                 190
Leu Thr His Val Ser Gln Thr Gln Glu Gln Asn Lys Glu Asn Gln Asn
                195                 200                 205
Pro Asn Ser Asp Ala Pro Val Ile Arg Ser Lys Thr Ser Ala Arg Tyr
210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                    245                 250                 255
Ser Asn Ser Arg Ser Gln Ile Lys Ala Ala Leu Asp Asn Ala Ser Lys
                260                 265                 270
Ile Met Ser Leu Thr Lys Thr Ala Pro Asp Tyr Leu Val Gly Gln Asn
                275                 280                 285
Pro Pro Glu Asp Ile Ser Ser Asn Arg Ile Tyr Arg Ile Leu Glu Met
290                 295                 300
Asn Gly Tyr Asp Pro Gln Tyr Ala Ala Ser Val Phe Leu Gly Trp Ala
305                 310                 315                 320
Gln Lys Lys Phe Gly Lys Arg Asn Thr Ile Trp Leu Phe Gly Pro Ala
                    325                 330                 335
Thr Thr Gly Lys Thr Asn Ile Ala Glu Ala Ile Ala His Ala Val Pro
                340                 345                 350
Phe Tyr Gly Cys Val Asn Trp Thr Asn Glu Asn Phe Pro Phe Asn Asp
                355                 360                 365
Cys Val Asp Lys Met Val Ile Trp Trp Glu Glu Gly Lys Met Thr Ala
370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                    405                 410                 415
Ile Val Thr Ser Asn Thr Asn Met Cys Ala Val Ile Asp Gly Asn Ser
                420                 425                 430
Thr Thr Phe Glu His Gln Gln Pro Leu Gln Asp Arg Met Phe Lys Phe
                435                 440                 445
Glu Leu Thr Lys Arg Leu Glu His Asp Phe Gly Lys Val Thr Lys Gln
                450                 455                 460
```

```
Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
            485                 490                 495

Pro Asn Asp Ala Asp Ile Ser Glu Pro Lys Arg Ala Cys Pro Ser Val
        500                 505                 510

Ala Gln Pro Ser Thr Ser Asp Ala Glu Ala Pro Val Asp Tyr Ala Asp
    515                 520                 525

Arg Tyr Gln Asn Lys Cys Ser Arg His Val Gly Met Asn Leu Met Leu
530                 535                 540

Phe Pro Cys Arg Gln Cys Glu Arg Met Asn Gln Asn Val Asp Ile Cys
545                 550                 555                 560

Phe Thr His Gly Val Met Asp Cys Ala Glu Cys Phe Pro Val Ser Glu
                565                 570                 575

Ser Gln Pro Val Ser Val Val Arg Lys Arg Thr Tyr Gln Lys Leu Cys
            580                 585                 590

Pro Ile His His Ile Met Gly Arg Ala Pro Glu Val Ala Cys Ser Ala
        595                 600                 605

Cys Glu Leu Ala Asn Val Asp Leu Asp Asp Cys Asp Met Glu Gln
    610                 615                 620

<210> SEQ ID NO 12
<211> LENGTH: 939
<212> TYPE: DNA
<213> ORGANISM: adeno-associated virus 4
<220> FEATURE:
<221> NAME/KEY: misc_feature
<223> OTHER INFORMATION: AAV4 Rep 40 gene

<400> SEQUENCE: 12
atggagctgg tcgggtggct ggtggaccgc gggatcacgt cagaaaagca atggatccag      60
gaggaccagg cgtcctacat ctccttcaac gccgcctcca actcgcggtc acaaatcaag     120
gccgcgctgg acaatgcctc caaaatcatg agcctgacaa agacggctcc ggactacctg     180
gtgggccaga acccgccgga ggacatttcc agcaaccgca tctaccgaat cctcgagatg     240
aacgggtacg atccgcagta cgcggcctcc gtcttcctgg gctgggcgca aaagaagttc     300
gggaagagga acaccatctg gctctttggg ccggccacga cgggtaaaac caacatcgcg     360
gaagccatcg cccacgccgt gccccttctac ggctgcgtga actggaccaa tgagaacttt     420
ccgttcaacg attgcgtcga caagatggtg atctggtggg aggagggcaa gatgacggcc     480
aaggtcgtag agagcgccaa ggccatcctg ggcggaagca aggtgcgcgt ggaccaaaag     540
tgcaagtcat cggcccagat cgacccaact cccgtgatcg tcacctccaa caccaacatg     600
tgcgcggtca tcgacggaaa ctcgaccacc ttcgagcacc aacaaccact ccaggaccgg     660
atgttcaagt tcgagctcac caagcgcctg gagcacgact ttggcaaggt caccaagcag     720
gaagtcaaag actttttccg gtgggcgtca gatcacgtga ccgaggtgac tcacgagttt     780
tacgtcagaa agggtggagc tagaaagagg cccgccccca tgacgcagat ataagtgag     840 cccaagcggg cctgtccgtc agttgcgcag ccatcgacgt cagacgcgga agctccggtg     900
gactacgcgg acagattggc tagaggacaa cctctctga                           939

<210> SEQ ID NO 13
<211> LENGTH: 1197
<212> TYPE: DNA
<213> ORGANISM: adeno-associated virus 4
<220> FEATURE:
<221> NAME/KEY: misc_feature
```

<223> OTHER INFORMATION: AAV4 Rep 52 gene

<400> SEQUENCE: 13

```
atggagctgg tcgggtggct ggtggaccgc gggatcacgt cagaaaagca atggatccag      60
gaggaccagg cgtcctacat ctccttcaac gccgcctcca actcgcggtc acaaatcaag     120
gccgcgctgg acaatgcctc caaaatcatg agcctgacaa agacggctcc ggactacctg     180
gtgggccaga acccgccgga ggacattttc cagcaaccgca tctaccgaat cctcgagatg     240
aacgggtacg atccgcagta cgcggcctcc gtcttcctgg gctgggcgca aaagaagttc     300
gggaagagga acaccatctg gctctttggg ccggccacga cgggtaaaac caacatcgcg     360
gaagccatcg cccacgccgt gcccttctac ggctgcgtga actggaccaa tgagaacttt     420
ccgttcaacg attgcgtcga caagatggtg atctggtggg aggagggcaa gatgacggcc     480
aaggtcgtag agagcgccaa ggccatcctg ggcggaagca aggtgcgcgt ggaccaaaag     540
tgcaagtcat cggcccagat cgacccaact cccgtgatcg tcacctccaa caccaacatg     600
tgcgcggtca tcgacggaaa ctcgaccacc ttcgagcacc aacaaccact ccaggaccgg     660
atgttcaagt tcgagctcac caagcgcctg gagcacgact ttggcaaggt caccaagcag     720
gaagtcaaag actttttccg gtgggcgtca gatcacgtga ccgaggtgac tcacgagttt     780
tacgtcagaa agggtggagc tagaaagagg cccgccccca tgacgcaga tataagtgag     840
cccaagcggg cctgtccgtc agttgcgcag ccatcgacgt cagacgcgga agctccggtg     900
gactacgcgg acaggtacca aaacaaatgt tctcgtcacg tgggtatgaa tctgatgctt     960
tttccctgcc ggcaatgcga gagaatgaat cagaatgtgg acatttgctt cacgcacggg    1020
gtcatggact gtgccgagtg cttccccgtg tcagaatctc aacccgtgtc tgtcgtcaga    1080
aagcggacgt atcagaaact gtgtccgatt catcacatca tggggagggc gcccgaggtg    1140
gcctgctcgg cctgcgaact ggccaatgtg gacttggatg actgtgacat ggaacaa      1197
```

<210> SEQ ID NO 14
<211> LENGTH: 1611
<212> TYPE: DNA
<213> ORGANISM: adeno-associated virus 4
<220> FEATURE:
<221> NAME/KEY: misc_feature
<223> OTHER INFORMATION: AAV4 Rep 68 gene

<400> SEQUENCE: 14

```
atgccggggt tctacgagat cgtgctgaag gtgcccagcg acctggacga gcacctgccc      60
ggcatttctg actcttttgt gagctgggtg gccgagaagg aatgggagct gccgccggat     120
tctgacatgg acttgaatct gattgagcag gcaccctga ccgtggccga aaagctgcaa      180
cgcgagttcc tggtcgagtg gcgccgcgtg agtaaggccc ggaggcccct cttctttgtc     240
cagttcgaga aggggacag ctacttccac ctgcacatcc tggtggagac cgtgggcgtc      300
aaatccatgg tggtgggccg ctacgtgagc cagattaaag agaagctggt gacccgcatc     360
taccgcgggg tcgagccgca gcttccgaac tggttcgcgg tgaccaagac gcgtaatggc     420
gccggaggcg ggaacaaggt ggtggacgac tgctacatcc ccaactacct gctccccaag     480
acccagcccg agctccagtg ggcgtggact aacatggacc agtatataag cgcctgtttg     540
aatctcgcgc agcgtaaacg gctggtgcg cagcatctga cgcacgtgtc gcagacgcag     600
gagcagaaca aggaaaacca gaaccccaat tctgacgcgc cggtcatcag gtcaaaaacc     660
tccgccaggt acatggagct ggtcgggtgg ctggtggacc gcgggatcac gtcagaaaag     720
caatggatcc aggaggacca ggcgtcctac atctccttca acgccgcctc caactcgcgg     780
```

```
tcacaaatca aggccgcgct ggacaatgcc tccaaaatca tgagcctgac aaagacggct      840
ccggactacc tggtgggcca gaacccgccg gaggacattt ccagcaaccg catctaccga      900
atcctcgaga tgaacgggta cgatccgcag tacgcggcct ccgtcttcct gggctgggcg      960
caaaagaagt tcgggaagag gaacaccatc tggctctttg gccggccac gacgggtaaa      1020 accaacatcg cggaagccat cgcccacgcc gtgcccttct acggctgcgt gaactggacc      1080
aatgagaact ttccgttcaa cgattgcgtc gacaagatgg tgatctggtg ggaggagggc      1140
aagatgacgg ccaaggtcgt agagagcgcc aaggccatcc tgggcggaag caaggtgcgc      1200
gtggaccaaa agtgcaagtc atcggcccag atcgacccaa ctcccgtgat cgtcacctcc      1260
aacaccaaca tgtgcgcggt catcgacgga aactcgacca ccttcgagca ccaacaacca      1320
ctccaggacc ggatgttcaa gttcgagctc accaagcgcc tggagcacga ctttggcaag      1380
gtcaccaagc aggaagtcaa agacttttc cggtgggcgt cagatcacgt gaccgaggtg      1440
actcacgagt tttacgtcag aaagggtgga gctagaaaga ggcccgcccc caatgacgca      1500
gatataagtg agcccaagcg ggcctgtccg tcagttgcgc agccatcgac gtcagacgcg      1560
gaagctccgg tggactacgc ggacagattg gctagaggac aacctctctg a      1611

<210> SEQ ID NO 15
<211> LENGTH: 1872
<212> TYPE: DNA
<213> ORGANISM: adeno-associated virus 4
<220> FEATURE:
<221> NAME/KEY: misc_feature
<223> OTHER INFORMATION: AAV4 Rep 78 gene

<400> SEQUENCE: 15
atgccggggt tctacgagat cgtgctgaag gtgcccagcg acctggacga gcacctgccc       60
ggcatttctg actctttgt gagctgggtg gccgagaagg aatgggagct gccgccggat      120
tctgacatgg acttgaatct gattgagcag gcacccctga ccgtgccga aaagctgcaa      180 cgcgagttcc tggtcgagtg gcgccgcgtg agtaaggccc cggaggccct cttctttgtc      240
cagttcgaga aggggacag ctacttccac ctgcacatcc tggtggagac cgtgggcgtc      300
aaatccatgg tggtgggccg ctacgtgagc cagattaaag agaagctggt gacccgcatc      360
taccgcgggg tcgagccgca gcttccgaac tggttcgcgg tgaccaagac gcgtaatggc      420
gccggaggcg ggaacaaggt ggtggacgac tgctacatcc ccaactacct gctccccaag      480
acccagcccg agctccagtg ggcgtggact aacatggacc agtatataag cgcctgtttg      540
aatctcgcgg agcgtaaacg gctggtggcg cagcatctga cgcacgtgtc gcagacgcag      600
gagcagaaca aggaaaacca gaaccccaat tctgacgcgc cggtcatcag gtcaaaaacc      660
tccgccaggt acatggagct ggtcgggtgg ctggtggacc gcgggatcac gtcagaaaag      720
caatggatcc aggaggacca ggcgtcctac atctccttca acgccgcctc caactcgcgg      780
tcacaaatca aggccgcgct ggacaatgcc tccaaaatca tgagcctgac aaagacggct      840
ccggactacc tggtgggcca gaacccgccg gaggacattt ccagcaaccg catctaccga      900
atcctcgaga tgaacgggta cgatccgcag tacgcggcct ccgtcttcct gggctgggcg      960
caaaagaagt tcgggaagag gaacaccatc tggctctttg gccggccac gacgggtaaa      1020 accaacatcg cggaagccat cgcccacgcc gtgcccttct acggctgcgt gaactggacc      1080
aatgagaact ttccgttcaa cgattgcgtc gacaagatgg tgatctggtg ggaggagggc      1140
aagatgacgg ccaaggtcgt agagagcgcc aaggccatcc tgggcggaag caaggtgcgc      1200
```

```
gtggaccaaa agtgcaagtc atcggcccag atcgacccaa ctcccgtgat cgtcacctcc   1260
aacaccaaca tgtgcgcggt catcgacgga aactcgacca ccttcgagca ccaacaacca   1320
ctccaggacc ggatgttcaa gttcgagctc accaagcgcc tggagcacga ctttggcaag   1380
gtcaccaagc aggaagtcaa agactttttc cggtgggcgt cagatcacgt gaccgaggtg   1440
actcacgagt tttacgtcag aaagggtgga gctagaaaga ggcccgcccc caatgacgca   1500
gatataagtg agcccaagcg ggcctgtccg tcagttgcgc agccatcgac gtcagacgcg   1560
gaagctccgg tggactacgc ggacaggtac caaaacaaat gttctcgtca cgtgggtatg   1620
aatctgatgc ttttccctg ccggcaatgc gagagaatga atcagaatgt ggacatttgc   1680
ttcacgcacg gggtcatgga ctgtgccgag tgcttccccg tgtcagaatc tcaacccgtg   1740
tctgtcgtca gaaagcggac gtatcagaaa ctgtgtccga ttcatcacat catggggagg   1800
gcgcccgagg tggcctgctc ggcctgcgaa ctggccaatg tggacttgga tgactgtgac   1860
atggaacaat aa                                                        1872
```

<210> SEQ ID NO 16
<211> LENGTH: 598
<212> TYPE: PRT
<213> ORGANISM: adeno-associated virus 4
<220> FEATURE:
<221> NAME/KEY: MISC_FEATURE
<223> OTHER INFORMATION: AAV4 capsid protein vp2

<400> SEQUENCE: 16

```
Thr Ala Pro Gly Lys Lys Arg Pro Leu Ile Glu Ser Pro Gln Gln Pro
1               5                   10                  15

Asp Ser Ser Thr Gly Ile Gly Lys Lys Gly Lys Gln Pro Ala Lys Lys
                20                  25                  30

Lys Leu Val Phe Glu Asp Glu Thr Gly Ala Gly Asp Gly Pro Pro Glu
            35                  40                  45

Gly Ser Thr Ser Gly Ala Met Ser Asp Asp Ser Glu Met Arg Ala Ala
        50                  55                  60

Ala Gly Gly Ala Ala Val Glu Gly Gly Gln Gly Ala Asp Gly Val Gly
65                  70                  75                  80

Asn Ala Ser Gly Asp Trp His Cys Asp Ser Thr Trp Ser Glu Gly His
                85                  90                  95

Val Thr Thr Thr Ser Thr Arg Thr Trp Val Leu Pro Thr Tyr Asn Asn
                100                 105                 110

His Leu Tyr Lys Arg Leu Gly Glu Ser Leu Gln Ser Asn Thr Tyr Asn
            115                 120                 125

Gly Phe Ser Thr Pro Trp Gly Tyr Phe Asp Phe Asn Arg Phe His Cys
        130                 135                 140

His Phe Ser Pro Arg Asp Trp Gln Arg Leu Ile Asn Asn Asn Trp Gly
145                 150                 155                 160

Met Arg Pro Lys Ala Met Arg Val Lys Ile Phe Asn Ile Gln Val Lys
                165                 170                 175

Glu Val Thr Thr Ser Asn Gly Glu Thr Thr Val Ala Asn Asn Leu Thr
            180                 185                 190

Ser Thr Val Gln Ile Phe Ala Asp Ser Ser Tyr Glu Leu Pro Tyr Val
        195                 200                 205

Met Asp Ala Gly Gln Glu Gly Ser Leu Pro Pro Phe Pro Asn Asp Val
    210                 215                 220

Phe Met Val Pro Gln Tyr Gly Tyr Cys Gly Leu Val Thr Gly Asn Thr
225                 230                 235                 240
```

Ser Gln Gln Gln Thr Asp Arg Asn Ala Phe Tyr Cys Leu Glu Tyr Phe
    245                 250                 255

Pro Ser Gln Met Leu Arg Thr Gly Asn Asn Phe Glu Ile Thr Tyr Ser
        260                 265                 270

Phe Glu Lys Val Pro Phe His Ser Met Tyr Ala His Ser Gln Ser Leu
    275                 280                 285

Asp Arg Leu Met Asn Pro Leu Ile Asp Gln Tyr Leu Trp Gly Leu Gln
290                 295                 300

Ser Thr Thr Thr Gly Thr Thr Leu Asn Ala Gly Thr Ala Thr Thr Asn
305                 310                 315                 320

Phe Thr Lys Leu Arg Pro Thr Asn Phe Ser Asn Phe Lys Lys Asn Trp
                325                 330                 335

Leu Pro Gly Pro Ser Ile Lys Gln Gln Gly Phe Ser Lys Thr Ala Asn
            340                 345                 350

Gln Asn Tyr Lys Ile Pro Ala Thr Gly Ser Asp Ser Leu Ile Lys Tyr
        355                 360                 365

Glu Thr His Ser Thr Leu Asp Gly Arg Trp Ser Ala Leu Thr Pro Gly
    370                 375                 380

Pro Pro Met Ala Thr Ala Gly Pro Ala Asp Ser Lys Phe Ser Asn Ser
385                 390                 395                 400

Gln Leu Ile Phe Ala Gly Pro Lys Gln Asn Gly Asn Thr Ala Thr Val
                405                 410                 415

Pro Gly Thr Leu Ile Phe Thr Ser Glu Glu Glu Leu Ala Ala Thr Asn
            420                 425                 430

Ala Thr Asp Thr Asp Met Trp Gly Asn Leu Pro Gly Gly Asp Gln Ser
        435                 440                 445

Asn Ser Asn Leu Pro Thr Val Asp Arg Leu Thr Ala Leu Gly Ala Val
    450                 455                 460

Pro Gly Met Val Trp Gln Asn Arg Asp Ile Tyr Tyr Gln Gly Pro Ile
465                 470                 475                 480

Trp Ala Lys Ile Pro His Thr Asp Gly His Phe His Pro Ser Pro Leu
                485                 490                 495

Ile Gly Gly Phe Gly Leu Lys His Pro Pro Pro Gln Ile Phe Ile Lys
            500                 505                 510

Asn Thr Pro Val Pro Ala Asn Pro Ala Thr Thr Phe Ser Ser Thr Pro
        515                 520                 525

Val Asn Ser Phe Ile Thr Gln Tyr Ser Thr Gly Gln Val Ser Val Gln
    530                 535                 540

Ile Asp Trp Glu Ile Gln Lys Glu Arg Ser Lys Arg Trp Asn Pro Glu
545                 550                 555                 560

Val Gln Phe Thr Ser Asn Tyr Gly Gln Gln Asn Ser Leu Leu Trp Ala
                565                 570                 575

Pro Asp Ala Ala Gly Lys Tyr Thr Glu Pro Arg Ala Ile Gly Thr Arg
            580                 585                 590

Tyr Leu Thr His His Leu
        595

<210> SEQ ID NO 17
<211> LENGTH: 1800
<212> TYPE: DNA
<213> ORGANISM: adeno-associated virus 4
<220> FEATURE:
<221> NAME/KEY: misc_feature
<223> OTHER INFORMATION: AAV4 capsid protein vp2 gene
<220> FEATURE:
<221> NAME/KEY: misc_feature
<222> LOCATION: (342)..(342)

<223> OTHER INFORMATION: n = unknown

<400> SEQUENCE: 17

```
acggctcctg gaaagaagag accgttgatt gaatccccccc agcagcccga ctcctccacg    60
ggtatcggca aaaaggcaa gcagccggct aaaaagaagc tcgttttcga agacgaaact    120
ggagcaggcg acggaccccc tgagggatca acttccggag ccatgtctga tgacagtgag    180
atgcgtgcag cagctggcgg agctgcagtc gagggsggac aaggtgccga tggagtgggt    240
aatgcctcgg gtgattggca ttgcgattcc acctggtctg agggccacgt cacgaccacc    300
agcaccagaa cctgggtctt gcccacctac aacaaccacc tntacaagcg actcggagag    360
agcctgcagt ccaacaccta caacggattc tccaccccct ggggatactt tgacttcaac    420
cgcttccact gccacttctc accacgtgac tggcagcgac tcatcaacaa caactggggc    480
atgcgaccca aagccatgcg ggtcaaaatc ttcaacatcc aggtcaagga ggtcacgacg    540
tcgaacggcg agacaacggt ggctaataac cttaccagca cggttcagat ctttgcggac    600
tcgtcgtacg aactgccgta cgtgatggat gcgggtcaag agggcagcct gcctcctttt    660
cccaacgacg tctttatggt gccccagtac ggctactgtg gactggtgac cggcaacact    720
tcgcagcaac agactgacag aaatgccttc tactgcctgg agtactttcc ttcgcagatg    780
ctgcggactg caacaacttt gaaattacg tacagttttg agaaggtgcc tttccactcg    840
atgtacgcgc acagccagag cctggaccgg ctgatgaacc ctctcatcga ccagtacctg    900
tggggactgc aatcgaccac caccggaacc accctgaatg ccgggactgc accaccaac    960
tttaccaagc tgcggcctac caacttttcc aactttaaaa agaactggct gcccgggcct   1020
tcaatcaagc agcagggctt ctcaaagact gccaatcaaa actacaagat ccctgccacc   1080
gggtcagaca gtctcatcaa atacgagacg cacagcactc tggacggaag atggagtgcc   1140
ctgacccccg gacctccaat ggccacggct ggacctgcgg acagcaagtt cagcaacagc   1200
cagctcatct ttgcggggcc taaacagaac ggcaacacgg ccaccgtacc cgggactctg   1260
atcttcacct ctgaggagga gctggcagcc accaacgcca ccgatacgga catgtggggc   1320
aacctacctg gcggtgacca gagcaacagc aacctgccga ccgtggacag actgacagcc   1380
ttgggagccg tgcctggaat ggtctggcaa aacagagaca tttactacca gggtcccatt   1440
tgggccaaga ttcctcatac cgatggacac tttcacccct accgctgat ggtgggttt   1500
gggctgaaac acccgcctcc tcaaattttt atcaagaaca ccccggtacc tgcgaatcct   1560
gcaacgacct tcagctctac tccggtaaac tccttcatta ctcagtacag cactggccag   1620
gtgtcggtgc agattgactg ggagatccag aaggagcggt ccaaacgctg gaaccccgag   1680
gtccagttta cctccaacta cggacagcaa actctctgt tgtgggctcc cgatgcggct   1740
gggaaataca ctgagcctag gctatcggt acccgctacc tcacccacca cctgtaataa   1800
```

<210> SEQ ID NO 18
<211> LENGTH: 544
<212> TYPE: PRT
<213> ORGANISM: adeno-associated virus 4
<220> FEATURE:
<221> NAME/KEY: MISC_FEATURE
<223> OTHER INFORMATION: AAV4 capsid protein vp3

<400> SEQUENCE: 18

```
Met Ser Asp Asp Ser Glu Met Arg Ala Ala Gly Gly Ala Ala Val
 1               5                  10                  15

Glu Gly Gly Gln Gly Ala Asp Gly Val Gly Asn Ala Ser Gly Asp Trp
             20                  25                  30
```

His Cys Asp Ser Thr Trp Ser Glu Gly His Val Thr Thr Ser Thr
            35                  40                  45

Arg Thr Trp Val Leu Pro Thr Tyr Asn Asn His Leu Tyr Lys Arg Leu
 50                  55                  60

Gly Glu Ser Leu Gln Ser Asn Thr Tyr Asn Gly Phe Ser Thr Pro Trp
 65                  70                  75                  80

Gly Tyr Phe Asp Phe Asn Arg Phe His Cys His Phe Ser Pro Arg Asp
                 85                  90                  95

Trp Gln Arg Leu Ile Asn Asn Asn Trp Gly Met Arg Pro Lys Ala Met
                100                 105                 110

Arg Val Lys Ile Phe Asn Ile Gln Val Lys Glu Val Thr Thr Ser Asn
                115                 120                 125

Gly Glu Thr Thr Val Ala Asn Asn Leu Thr Ser Thr Val Gln Ile Phe
                130                 135                 140

Ala Asp Ser Ser Tyr Glu Leu Pro Tyr Val Met Asp Ala Gly Gln Glu
145                 150                 155                 160

Gly Ser Leu Pro Pro Phe Pro Asn Asp Val Phe Met Val Pro Gln Tyr
                165                 170                 175

Gly Tyr Cys Gly Leu Val Thr Gly Asn Thr Ser Gln Gln Gln Thr Asp
                180                 185                 190

Arg Asn Ala Phe Tyr Cys Leu Glu Tyr Phe Pro Ser Gln Met Leu Arg
                195                 200                 205

Thr Gly Asn Asn Phe Glu Ile Thr Tyr Ser Phe Glu Lys Val Pro Phe
                210                 215                 220

His Ser Met Tyr Ala His Ser Gln Ser Leu Asp Arg Leu Met Asn Pro
225                 230                 235                 240

Leu Ile Asp Gln Tyr Leu Trp Gly Leu Gln Ser Thr Thr Thr Gly Thr
                245                 250                 255

Thr Leu Asn Ala Gly Thr Ala Thr Thr Asn Phe Thr Lys Leu Arg Pro
                260                 265                 270

Thr Asn Phe Ser Asn Phe Lys Lys Asn Trp Leu Pro Gly Pro Ser Ile
                275                 280                 285

Lys Gln Gln Gly Phe Ser Lys Thr Ala Asn Gln Asn Tyr Lys Ile Pro
                290                 295                 300

Ala Thr Gly Ser Asp Ser Leu Ile Lys Tyr Glu Thr His Ser Thr Leu
305                 310                 315                 320

Asp Gly Arg Trp Ser Ala Leu Thr Pro Gly Pro Pro Met Ala Thr Ala
                325                 330                 335

Gly Pro Ala Asp Ser Lys Phe Ser Asn Ser Gln Leu Ile Phe Ala Gly
                340                 345                 350

Pro Lys Gln Asn Gly Asn Thr Ala Thr Val Pro Gly Thr Leu Ile Phe
                355                 360                 365

Thr Ser Glu Glu Glu Leu Ala Ala Thr Asn Ala Thr Asp Thr Asp Met
370                 375                 380

Trp Gly Asn Leu Pro Gly Gly Asp Gln Ser Asn Ser Asn Leu Pro Thr
385                 390                 395                 400

Val Asp Arg Leu Thr Ala Leu Gly Ala Val Pro Gly Met Val Trp Gln
                405                 410                 415

Asn Arg Asp Ile Tyr Tyr Gln Gly Pro Ile Trp Ala Lys Ile Pro His
                420                 425                 430

Thr Asp Gly His Phe His Pro Ser Pro Leu Ile Gly Gly Phe Gly Leu
                435                 440                 445

Lys His Pro Pro Pro Gln Ile Phe Ile Lys Asn Thr Pro Val Pro Ala

```
                  450                   455                  460
Asn Pro Ala Thr Thr Phe Ser Ser Thr Pro Val Asn Ser Phe Ile Thr
465                 470                  475                  480

Gln Tyr Ser Thr Gly Gln Val Ser Val Gln Ile Asp Trp Glu Ile Gln
                    485                  490                  495

Lys Glu Arg Ser Lys Arg Trp Asn Pro Glu Val Gln Phe Thr Ser Asn
                500                  505                  510

Tyr Gly Gln Gln Asn Ser Leu Leu Trp Ala Pro Asp Ala Ala Gly Lys
                515                  520                  525

Tyr Thr Glu Pro Arg Ala Ile Gly Thr Arg Tyr Leu Thr His His Leu
                530                  535                  540

<210> SEQ ID NO 19
<211> LENGTH: 1617
<212> TYPE: DNA
<213> ORGANISM: adeno-associated virus 4
<220> FEATURE:
<221> NAME/KEY: misc_feature
<223> OTHER INFORMATION: AAV4 capsid protein vp3 gene
<220> FEATURE:
<221> NAME/KEY: misc_feature
<222> LOCATION: (162)..(162)
<223> OTHER INFORMATION: n = unknown

<400> SEQUENCE: 19
atgcgtgcag cagctggcgg agctgcagtc gagggsggac aaggtgccga tggagtgggt    60
aatgcctcgg gtgattggca ttgcgattcc acctggtctg agggccacgt cacgaccacc   120
agcaccagaa cctgggtctt gcccacctac aacaaccacc tntacaagcg actcggagag   180
agcctgcagt ccaacaccta caacggattc tccacccccct ggggatactt tgacttcaac   240
cgcttccact gccacttctc accacgtgac tggcagcgac tcatcaacaa caactggggc   300
atgcgaccca agccatgcg ggtcaaaatc ttcaacatcc aggtcaagga ggtcacgacg   360
tcgaacggcg agacaacggt ggctaataac cttaccagca cggttcagat ctttgcggac   420
tcgtcgtacg aactgccgta cgtgatggat gcgggtcaag agggcagcct gcctcctttt   480
cccaacgacg tctttatggt gccccagtac ggctactgtg actggtgac cggcaacact   540 tcgcagcaac agactgacag aaatgccttc tactgcctgg agtactttcc ttcgcagatg   600
ctgcggactg caacaacctt tgaaattacg tacagttttg agaaggtgcc tttccactcg   660
atgtacgcgc acagccagag cctggaccgg ctgatgaacc ctctcatcga ccagtacctg   720
tggggactgc aatcgaccac caccggaacc accctgaatg ccgggactgc accaccaac   780 tttaccaagc tgcggcctac caacttttcc aactttaaaa agaactggct gcccgggcct   840
tcaatcaagc agcagggctt ctcaaagact gccaatcaaa actacaagat ccctgccacc   900
gggtcagaca gtctcatcaa atacgagacg cacagcactc tggacggaag atggagtgcc   960
ctgacccccg acctccaat ggccacggct ggacctgcgg acagcaagtt cagcaacagc  1020
cagctcatct ttgcggggcc taaacagaac ggcaacacgg ccaccgtacc cgggactctg  1080
atcttcacct ctgaggagga gctggcagcc accaacgcca ccgatacgga catgtggggc  1140
aacctacctg gcggtgacca gagcaacagc aacctgccga ccgtggacag actgacagcc  1200
ttgggagccg tgcctggaat ggtctggcaa acagagacga tttactacca gggtcccatt  1260
tgggccaaga ttcctcatac cgatggacac tttcacccct accgctgat ggtgggttt  1320 gggctgaaac acccgcctcc tcaaattttt atcaagaaca ccccggtacc tgcgaatcct  1380
gcaacgacct tcagctctac tccggtaaac tccttcatta ctcagtacag cactggccag  1440
```

-continued

```
gtgtcggtgc agattgactg ggagatccag aaggagcggt ccaaacgctg gaacccgag    1500 gtccagttta cctccaacta cggacagcaa aactctctgt tgtgggctcc cgatgcggct    1560
gggaaataca ctgagcctag ggctatcggt acccgctacc tcacccacca cctgtaa      1617

<210> SEQ ID NO 20
<211> LENGTH: 129
<212> TYPE: DNA
<213> ORGANISM: adeno-associated virus 4
<220> FEATURE:
<221> NAME/KEY: misc_feature
<223> OTHER INFORMATION: AAV4 ITR "flop" orientation

<400> SEQUENCE: 20
ttggccactc cctctatgcg cgctcgctca ctcactcggc cctgcggcca gaggccggca     60
gtctggagac ctttggtgtc cagggcaggg ccgagtgagt gagcgagcgc gcatagaggg    120
agtggccaa                                                           129

<210> SEQ ID NO 21
<211> LENGTH: 35
<212> TYPE: DNA
<213> ORGANISM: Artificial Sequence
<220> FEATURE:
<223> OTHER INFORMATION: Primer

<400> SEQUENCE: 21
tctagtctag acttggccac tccctctctg cgcgc                                35

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
aggccttaag agcagtcgtc caccaccttg ttcc                                 34
```

AAV4 VECTOR AND USES THEREOF

CROSS REFERENCE TO RELATED APPLICATIONS

This application is a continuation of U.S. patent application Ser. No. 10/719,311 filed Nov. 20, 2003, which is a continuation of now abandoned U.S. patent application Ser. No. 09/254,747 filed Nov. 26, 1999, which is a national stage application under 35 U.S.C. 371 of PCT Patent Application No. PCT/US97/16266 having an international filing date of Sep. 11, 1997, which claims the benefit of Provisional Patent Application No. 60/025,934 filed Sep. 11, 1996, the entire disclosure of each of which are hereby incorporated herein by reference.

REFERENCE TO SEQUENCE LISTING

This application contains a Sequence Listing submitted as an electronic text file named "SEQUENCE_LISTING_priority_case.txt", having a size in bytes of 71 kb, and created on Nov. 12, 2009. The information contained in this electronic file is hereby incorporated by reference in its entirety pursuant to 37 CFR §1.52(e)(5).

BACKGROUND OF THE INVENTION

1. Field of the Invention

The present invention provides adeno-associated virus 4 (AAV4) and vectors derived therefrom. Thus, the present invention relates to AAV4 vectors for and methods of delivering nucleic acids to cells of subjects.

2. Background Art

Adeno associated virus (AAV) is a small nonpathogenic virus of the parvoviridae family (for review see 28). AAV is distinct from the other members of this family by its dependence upon a helper virus for replication. In the absence of a helper virus, AAV may integrate in a locus specific manner into the q arm of chromosome 19 (21). The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosahedral capsid is approximately 20 nm in diameter.

To date 7 serologically distinct AAVs have been identified and 5 have been isolated from humans or primates and are referred to as AAV types 1-5 (1). The most extensively studied of these isolates is AAV type 2 (AAV2). The genome of AAV2 is 4680 nucleotides in length and contains two open reading frames (ORFs). The left ORF encodes the non-structural Rep proteins, Rep40, Rep 52, Rep68 and Rep 78, which are involved in regulation of replication and transcription in addition to the production of single-stranded progeny genomes (5-8, 11, 12, 15, 17, 19, 21-23, 25, 34, 37-40). Furthermore, two of the Rep proteins have been associated with the preferential integration of AAV genomes into a region of the q arm of human chromosome 19. Rep68/78 have also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation (7, 8, 26). This binding serves to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The AAV2 virion is a non-enveloped, icosahedral particle approximately 25 nm in diameter, consisting of three related proteins referred to as VP1, 2 and 3. The right ORF encodes the capsid proteins, VP1, VP2, and VP3. These proteins are found in a ratio of 1:1:10 respectively and are all derived from the right-hand ORF. The capsid proteins differ from each other by the use of alternative splicing and an unusual start codon. Deletion analysis has shown that removal or alteration of VP1 which is translated from an alternatively spliced message results in a reduced yield of infections particles (15, 16, 38). Mutations within the VP3 coding region result in the failure to produce any single-stranded progeny DNA or infectious particles (15, 16, 38).

The following features of AAV have made it an attractive vector for gene transfer (16). AAV vectors have been shown in vitro to stably integrate into the cellular genome; possess a broad host range; transduce both dividing and non dividing cells in vitro and in vivo (13, 20, 30, 32) and maintain high levels of expression of the transduced genes (41). Viral particles are heat stable, resistant to solvents, detergents, changes in pH, temperature, and can be concentrated on CsCl gradients (1,2). Integration of AAV provirus is not associated with any long term negative effects on cell growth or differentiation (3,42). The ITRs have been shown to be the only cis elements required for replication, packaging and integration (35) and may contain some promoter activities (14).

Initial data indicate that AAV4 is a unique member of this family. DNA hybridization data indicated a similar level of homology for AAV1-4 (31). However, in contrast to the other AAVs only one ORF corresponding to the capsid proteins was identified in AAV4 and no ORF was detected for the Rep proteins (27).

AAV2 was originally thought to infect a wide variety of cell types provided the appropriate helper virus was present. Recent work has shown that some cell lines are transduced very poorly by AAV2 (30). While the receptor has not been completely characterized, binding studies have indicated that it is poorly expressed on erythroid cells (26). Recombinant AAV2 transduction of CD34$^+$, bone marrow pluripotent cells, requires a multiplicity of infection (MOI) of $10^4$ particles per cell (A. W. Nienhuis unpublished results). This suggests that transduction is occurring by a non-specific mechanism or that the density of receptors displayed on the cell surface is low compared to other cell types.

The present invention provides a vector comprising the AAV4 virus as well as AAV4 viral particles. While AAV4 is similar to AAV2, the two viruses are found herein to be physically and genetically distinct. These differences endow AAV4 with some unique advantages which better suit it as a vector for gene therapy. For example, the wt AAV4 genome is larger than AAV2, allowing for efficient encapsidation of a larger recombinant genome. Furthermore, wt AAV4 particles have a greater buoyant density than AAV2 particles and therefore are more easily separated from contaminating helper virus and empty AAV particles than AAV2-based particles.

Additionally, in contrast to AAV1, 2, and 3, AAV4, is able to hemagglutinate human, guinea pig, and sheep erythrocytes (18).

Furthermore, as shown herein, AAV4 capsid protein, again surprisingly, is distinct from AAV2 capsid protein and exhibits different tissue tropism. AAV2 and AAV4 have been shown to be serologically distinct and thus, in a gene therapy application, AAV4 would allow for transduction of a patient who already possesses neutralizing antibodies to AAV2 either as a result of natural immunological defense or from prior exposure to AAV2 vectors. Thus, the present invention, by providing these new recombinant vectors and particles based on AAV4 provides a new and highly useful series of vectors.

SUMMARY OF THE INVENTION

The present invention provides a nucleic acid vector comprising a pair of adeno-associated virus 4 (AAV4) inverted terminal repeats and a promoter between the inverted terminal repeats.

The present invention further provides an AAV4 particle containing a vector comprising a pair of AAV2 inverted terminal repeats.

Additionally, the instant invention provides an isolated nucleic acid comprising the nucleotide sequence set forth in SEQ ID NO:1 [AAV4 genome]. Furthermore, the present invention provides an isolated nucleic acid consisting essentially of the nucleotide sequence set forth in SEQ ID NO:1 [AAV4 genome].

The present invention provides an isolated nucleic acid encoding an adeno-associated virus 4 Rep protein. Additionally provided is an isolated AAV4 Rep protein having the amino acid sequence set forth in SEQ ID NO:2, or a unique fragment thereof. Additionally provided is an isolated AAV4 Rep protein having the amino acid sequence set forth in SEQ ID NO:8, or a unique fragment thereof. Additionally provided is an isolated AAV4 Rep protein having the amino acid sequence set forth in SEQ ID NO:9, or a unique fragment thereof. Additionally provided is an isolated AAV4 Rep protein having the amino acid sequence set forth in SEQ ID NO:10, or a unique fragment thereof. Additionally provided is an isolated AAV4 Rep protein having the amino acid sequence set forth in SEQ ID NO:11, or a unique fragment thereof.

The present invention further provides an isolated AAV4 capsid protein having the amino acid sequence set forth in SEQ ID NO:4. Additionally provided is an isolated AAV4 capsid protein having the amino acid sequence set forth in SEQ ID NO:16. Also provided is an isolated AAV4 capsid protein having the amino acid sequence set forth in SEQ ID NO:18.

The present invention additionally provides an isolated nucleic acid encoding adeno-associated virus 4 capsid protein.

The present invention further provides an AAV4 particle comprising a capsid protein consisting essentially of the amino acid sequence set forth in SEQ ID NO:4.

Additionally provided by the present invention is an isolated nucleic acid comprising an AAV4 p5 promoter.

The instant invention provides a method of screening a cell for infectivity by AAV4 comprising contacting the cell with AAV4 and detecting the presence of AAV4 in the cells.

The present invention further provides a method of delivering a nucleic acid to a cell comprising administering to the cell an AAV4 particle containing a vector comprising the nucleic acid inserted between a pair of AAV inverted terminal repeats, thereby delivering the nucleic acid to the cell.

The present invention also provides a method of delivering a nucleic acid to a subject comprising administering to a cell from the subject an AAV4 particle comprising the nucleic acid inserted between a pair of AAV inverted terminal repeats, and returning the cell to the subject, thereby delivering the nucleic acid to the subject.

The present invention further provides a method of delivering a nucleic acid to a subject comprising administering to a cell from the subject an AAV4 particle comprising the nucleic acid inserted between a pair of AAV inverted terminal repeats, and returning the cell to the subject, thereby delivering the nucleic acid to the subject.

The present invention also provides a method of delivering a nucleic acid to a cell in a subject comprising administering to the subject an AAV4 particle comprising the nucleic acid inserted between a pair of AAV inverted terminal repeats, thereby delivering the nucleic acid to a cell in the subject.

The instant invention further provides a method of delivering a nucleic acid to a cell in a subject having antibodies to AAV2 comprising administering to the subject an AAV4 particle comprising the nucleic acid, thereby delivering the nucleic acid to a cell in the subject.

BRIEF DESCRIPTION OF THE DRAWINGS

FIG. 2 shows AAV4 ITR. The sequence of the ITR (SEQ ID NO: 20) is shown in the hairpin conformation. The putative Rep binding site is boxed. The cleavage site in the trs is indicated by an arrow. Bases which differ from the ITR of AAV2 are outlined.

DETAILED DESCRIPTION OF THE INVENTION

Figure 1:
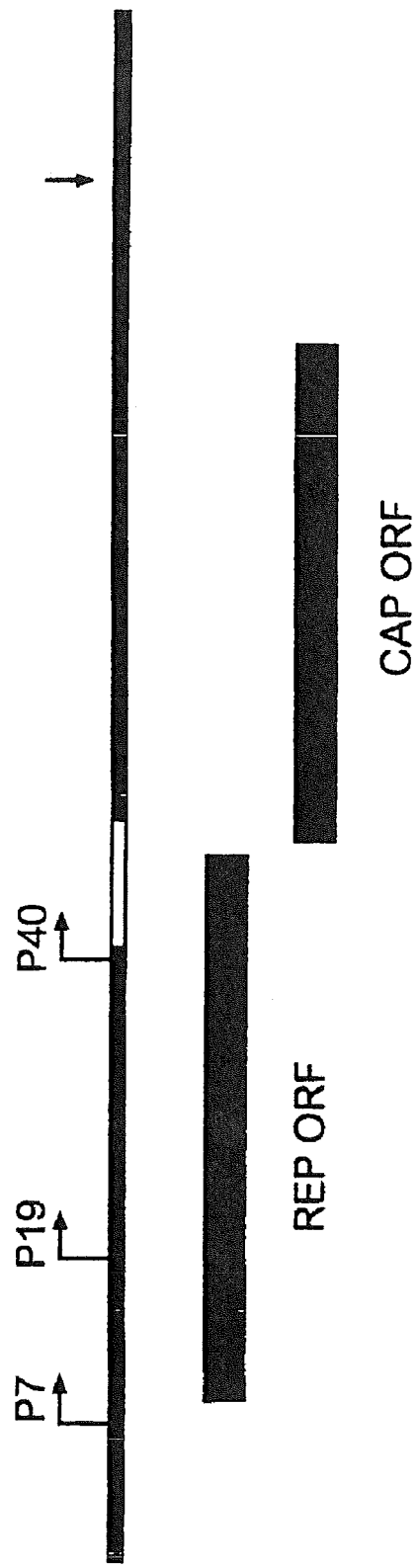
FIG. 1 shows a schematic outline of AAV 4. Promoters are indicated by horizontal arrows with their corresponding map positions indicated above. The polyadenylation site is indicated by a vertical arrow and the two open reading frames are indicated by black boxes. The splice region is indicated by a shaded box.

As used in the specification and in the claims, "a" can mean one or more, depending upon the context in which it is used.

The present invention provides the nucleotide sequence of the adeno-associated virus 4 (AAV4) genome and vectors and particles derived therefrom. Specifically, the present invention provides a nucleic acid vector comprising a pair of AAV4 inverted terminal repeats (ITRs) and a promoter between the inverted terminal repeats. The AAV4 ITRs are exemplified by the nucleotide sequence set forth in SEQ ID NO:6 and SEQ ID NO:20; however, these sequences can have minor modifications and still be contemplated to constitute AAV4 ITRs. The nucleic acid listed in SEQ ID NO:6 depicts the ITR in the "flip" orientation of the ITR. The nucleic acid listed in SEQ ID NO:20 depicts the ITR in the "flop" orientation of the ITR. Minor modifications in an ITR of either orientation are those that will not interfere with the hairpin structure formed by the AAV4 ITR as described herein and known in the art. Furthermore, to be considered within the term "AAV4 ITRs" the nucleotide sequence must retain the Rep binding site described herein and exemplified in SEQ ID NO:6 and SEQ ID NO:20, i.e., it must retain one or both features described herein that distinguish the AAV4 ITR from the AAV2 ITR: (1) four (rather than three as in AAV2) "GAGC" repeats and (2) in the AAV4 ITR Rep binding site the fourth nucleotide in the first two "GAGC" repeats is a T rather than a C.

The promoter can be any desired promoter, selected by known considerations, such as the level of expression of a nucleic acid functionally linked to the promoter and the cell type in which the vector is to be used. Promoters can be an exogenous or an endogenous promoter. Promoters can include, for example, known strong promoters such as SV40 or the inducible metallothionein promoter, or an AAV promoter, such as an AAV p5 promoter. Additional examples of promoters include promoters derived from actin genes, immunoglobulin genes, cytomegalovirus (CMV), adenovirus, bovine papilloma virus, adenoviral promoters, such as the adenoviral major late promoter, an inducible heat shock promoter, respiratory syncytial virus, Rous sarcomas virus (RSV), etc. Specifically, the promoter can be AAV2 p5 promoter or AAV4 p5 promoter. More specifically, the AAV4 p5 promoter can be about nucleotides 130 to 291 of SEQ ID NO: 1. Additionally, the p5 promoter may be enhanced by nucleotides 1-130. Furthermore, smaller fragments of p5 promoter that retain promoter activity can readily be determined by standard procedures including, for example, constructing a series of deletions in the p5 promoter, linking the deletion to a reporter gene, and determining whether the reporter gene is expressed, i.e., transcribed and/or translated.

It should be recognized that the nucleotide and amino acid sequences set forth herein may contain minor sequencing errors. Such errors in the nucleotide sequences can be corrected, for example, by using the hybridization procedure described above with various probes derived from the described sequences such that the coding sequence can be reisolated and resequenced. The corresponding amino acid sequence can then be corrected accordingly.

The AAV4 vector can further comprise an exogenous nucleic acid functionally linked to the promoter. By "heterologous nucleic acid" is meant that any heterologous or exogenous nucleic acid can be inserted into the vector for transfer into a cell, tissue or organism. The nucleic acid can encode a polypeptide or protein or an antisense RNA, for example. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid can encode beneficial proteins that replace missing or defective proteins required by the subject into which the vector in transferred or can encode a cytotoxic polypeptide that can be directed, e.g., to cancer cells or other cells whose death would be beneficial to the subject. The heterologous nucleic acid can also encode antisense RNAs that can bind to, and thereby inactivate, mRNAs made by the subject that encode harmful proteins. In one embodiment, antisense polynucleotides can be produced from a heterologous expression cassette in an AAV4 viral construct where the expression cassette contains a sequence that promotes cell-type specific expression (Wirak et al., *EMBO* 10:289 (1991)). For general methods relating to antisense polynucleotides, see *Antisense RNA and DNA*, D. A. Melton, Ed., Cold Spring Harbor Laboratory, Cold Spring Harbor, N.Y. (1988).

Examples of heterologous nucleic acids which can be administered to a cell or subject as part of the present AAV4 vector can include, but are not limited to the following: nucleic acids encoding therapeutic agents, such as tumor necrosis factors (TNF), such as TNF-α; interferons, such as interferon-α, interferon-β, and interferon-γ; interleukins, such as IL-1, IL-1γ, and ILs-2 through -14; GM-CSF; adenosine deaminase; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; Fc receptors for antigen binding domains of antibodies, such as immunoglobulins; and antisense sequences which inhibit viral replication, such as antisense sequences which inhibit replication of hepatitis B or hepatitis non-A, non-B virus. The nucleic acid is chosen considering several factors, including the cell to be transfected. Where the target cell is a blood cell, for example, particularly useful nucleic acids to use are those which allow the blood cells to exert a therapeutic effect, such as a gene encoding a clotting factor for use in treatment of hemophilia. Furthermore, the nucleic acid can encode more than one gene product, limited only, if the nucleic acid is to be packaged in a capsid, by the size of nucleic acid that can be packaged.

Furthermore, suitable nucleic acids can include those that, when transferred into a primary cell, such as a blood cell, cause the transferred cell to target a site in the body where that cell's presence would be beneficial. For example, blood cells such as TIL cells can be modified, such as by transfer into the cell of a Fab portion of a monoclonal antibody, to recognize a selected antigen. Another example would be to introduce a nucleic acid that would target a therapeutic blood cell to tumor cells. Nucleic acids useful in treating cancer cells include those encoding chemotactic factors which cause an inflammatory response at a specific site, thereby having a therapeutic effect.

Cells, particularly blood cells, having such nucleic acids transferred into them can be useful in a variety of diseases, syndromes and conditions. For example, suitable nucleic acids include nucleic acids encoding soluble CD4, used in the treatment of AIDS and α-antitrypsin, used in the treatment of emphysema caused by α-antitrypsin deficiency. Other diseases, syndromes and conditions in which such cells can be useful include, for example, adenosine deaminase deficiency, sickle cell deficiency, brain disorders such as Alzheimer's disease, thalassemia, hemophilia, diabetes, phenylketonuria, growth disorders and heart diseases, such as those caused by alterations in cholesterol metabolism, and defects of the immune system.

As another example, hepatocytes can be transfected with the present vectors having useful nucleic acids to treat liver disease. For example, a nucleic acid encoding OTC can be used to transfect hepatocytes (ex vivo and returned to the liver or in vivo) to treat congenital hyperammonemia, caused by an inherited deficiency in OTC. Another example is to use a nucleic acid encoding LDL to target hepatocytes ex vivo or in vivo to treat inherited LDL receptor deficiency. Such transfected hepatocytes can also be used to treat acquired infectious diseases, such as diseases resulting from a viral infection. For example, transduced hepatocyte precursors can be used to treat viral hepatitis, such as hepatitis B and non-A, non-B hepatitis, for example by transducing the hepatocyte precursor with a nucleic acid encoding an antisense RNA that inhibits viral replication. Another example includes transferring a vector of the present invention having a nucleic acid encoding a protein, such as α-interferon, which can confer resistance to the hepatitis virus.

For a procedure using transfected hepatocytes or hepatocyte precursors, hepatocyte precursors having a vector of the present invention transferred in can be grown in tissue culture, removed form the tissue culture vessel, and introduced to the body, such as by a surgical method. In this example, the tissue would be placed directly into the liver, or into the body cavity in proximity to the liver, as in a transplant or graft. Alternatively, the cells can simply be directly injected into the liver, into the portal circulatory system, or into the spleen, from which the cells can be transported to the liver via the circulatory system. Furthermore, the cells can be attached to a support, such as microcarrier beads, which can then be introduced, such as by injection, into the peritoneal cavity. Once the cells are in the liver, by whatever means, the cells can then express the nucleic acid and/or differentiate into mature hepatocytes which can express the nucleic acid.

The present invention also contemplates any unique fragment of these AAV4 nucleic acids, including the AAV4 nucleic acids set forth in SEQ ID NOs: 1, 3, 5, 6, 7, 12-15, 17 and 19. To be unique, the fragment must be of sufficient size to distinguish it from other known sequences, most readily determined by comparing any nucleic acid fragment to the nucleotide sequences of nucleic acids in computer databases, such as GenBank. Such comparative searches are standard in the art. Typically, a unique fragment useful as a primer or probe will be at least about 8 or 10 to about 20 or 25 nucleotides in length, depending upon the specific nucleotide content of the sequence. Additionally, fragments can be, for example, at least about 30, 40, 50, 75, 100, 200 or 500 nucleotides in length. The nucleic acid can be single or double stranded, depending upon the purpose for which it is intended.

The present invention further provides an AAV4 Capsid polypeptide or a unique fragment thereof. AAV4 capsid polypeptide is encoded by ORF 2 of AAV4. Specifically, the present invention provides an AAV4 Capsid protein comprising the amino acid sequence encoded by nucleotides 2260-4467 of the nucleotide sequence set forth in SEQ ID NO:1, or a unique fragment of such protein. The present invention also provides an AAV4 Capsid protein consisting essentially of the amino acid sequence encoded by nucleotides 2260-4467 of the nucleotide sequence set forth in SEQ ID NO:1, or a unique fragment of such protein. The present invention further provides the individual AAV4 coat proteins, VP1, VP2 and VP3. Thus, the present invention provides an isolated polypeptide having the amino acid sequence set forth in SEQ ID NO:4 (VP1). The present invention additionally provides an isolated polypeptide having the amino acid sequence set forth in SEQ ID NO:16 (VP2). The present invention also provides an isolated polypeptide having the amino acid sequence set forth in SEQ ID NO:18 (VP3). By "unique fragment thereof" is meant any smaller polypeptide fragment encoded by any AAV4 capsid gene that is of sufficient length to be unique to the AAV4 Capsid protein. Substitutions and modifications of the amino acid sequence can be made as described above and, further, can include protein processing modifications, such as glycosylation, to the polypeptide. However, an AAV4 Capsid polypeptide including all three coat proteins will have at least about 63% overall homology to the polypeptide encoded by nucleotides 2260-4467 of the sequence set forth in SEQ ID NO: 1. The protein can have about 65%, about 70%, about 75%, about 80%, about 85%, about 90%, about 95% or even 100% homology to the amino acid sequence encoded by the nucleotides 2260-4467 of the sequence set forth in SEQ ID NO:1. An AAV4 VP2 polypeptide can have at least about 58%, about 60%, about 70%, about 80%, about 90% about 95% or about 100% homology to the amino acid sequence set forth in SEQ ID NO:16. An AAV4 VP3 polypeptide can have at least about 60%, about 70%, about 80%, about 90% about 95% or about 100% homology to the amino acid sequence set forth in SEQ ID NO:18.

The herein described AAV4 nucleic acid vector can be encapsidated in an AAV particle. In particular, it can be encapsidated in an AAV1 particle, an AAV2 particle, an AAV3 particle, an AAV4 particle, or an AAV5 particle by standard methods using the appropriate capsid proteins in the encapsidation process, as long as the nucleic acid vector fits within the size limitation of the particle utilized. The encapsidation process itself is standard in the art.

An AAV4 particle is a viral particle comprising an AAV4 capsid protein. An AAV4 capsid polypeptide encoding the entire VP1, VP2, and VP3 polypeptide can overall have at least about 63% homology to the polypeptide having the amino acid sequence encoded by nucleotides 2260-4467 set forth in SEQ ID NO:1 (AAV4 capsid protein). The capsid protein can have about 70% homology, about 75% homology, 80% homology, 85% homology, 90% homology, 95% homology, 98% homology, 99% homology, or even 100% homology to the protein having the amino acid sequence encoded by nucleotides 2260-4467 set forth in SEQ ID NO:1. The particle can be a particle comprising both AAV4 and AAV2 capsid protein, i.e., a chimeric protein. Variations in the amino acid sequence of the AAV4 capsid protein are contemplated herein, as long as the resulting viral particle comprising the AAV4 capsid remains antigenically or immunologically distinct from AAV2, as can be routinely determined by standard methods. Specifically, for example, ELISA and Western blots can be used to determine whether a viral particle is antigenically or immunologically distinct from AAV2. Furthermore, the AAV4 viral particle preferably retains tissue tropism distinction from AAV2, such as that exemplified in the examples herein, though an AAV4 chimeric particle comprising at least one AAV4 coat protein may have a different tissue tropism from that of an AAV4 particle consisting only of AAV4 coat proteins.

An AAV4 particle is a viral particle comprising an AAV4 capsid protein. An AAV4 capsid polypeptide encoding the entire VP1, VP2, and VP3 polypeptide can overall have at least about 63% homology to the polypeptide having the amino acid sequence encoded by nucleotides 2260-4467 set forth in SEQ ID NO:1 (AAV4 capsid protein). The capsid protein can have about 70% homology, about 75% homology, 80% homology, 85% homology, 90% homology, 95% homology, 98% homology, 99% homology, or even 100% homology to the protein having the amino acid sequence encoded by nucleotides 2260-4467 set forth in SEQ ID NO:1. The particle can be a particle comprising both AAV4 and AAV2 capsid protein, i.e., a chimeric protein. Variations in the amino acid sequence of the AAV4 capsid protein are contemplated herein, as long as the resulting viral particle comprising the AAV4 capsid remains antigenically or immunologically distinct from AAV2, as can be routinely determined by standard methods. Specifically, for example, ELISA and Western blots can be used to determine whether a viral particle is antigenically or immunologically distinct from AAV2. Furthermore, the AAV4 viral particle preferably retains tissue tropism distinction from AAV2, such as that exemplified in the examples herein, though an AAV4 chimeric particle comprising at least one AAV4 coat protein may have a different tissue tropism from that of an AAV4 particle consisting only of AAV4 coat proteins.

The invention further provides an AAV4 particle containing, i.e., encapsidating, a vector comprising a pair of AAV2 inverted terminal repeats. The nucleotide sequence of AAV2 ITRs is known in the art. Furthermore, the particle can be a particle comprising both AAV4 and AAV2 capsid protein, i.e., a chimeric protein. The vector encapsidated in the particle can further comprise an exogenous nucleic acid inserted between the inverted terminal repeats.

The present invention further provides an isolated nucleic acid comprising the nucleotide sequence set forth in SEQ ID NO:1 (AAV4 genome). This nucleic acid, or portions thereof, can be inserted into other vectors, such as plasmids, yeast artificial chromosomes, or other viral vectors, if desired, by standard cloning methods. The present invention also provides an isolated nucleic acid consisting essentially of the nucleotide sequence set forth in SEQ ID NO:1. The nucleotides of SEQ ID NO:1 can have minor modifications and still be contemplated by the present invention. For example, modifications that do not alter the amino acid encoded by any given codon (such as by modification of the third, "wobble," position in a codon) can readily be made, and such alterations are known in the art. Furthermore, modifications that cause a resulting neutral amino acid substitution of a similar amino acid can be made in a coding region of the genome. Additionally, modifications as described herein for the AAV4 components, such as the ITRs, the p5 promoter, etc. are contemplated in this invention.

The present invention additionally provides an isolated nucleic acid that selectively hybridizes with an isolated nucleic acid consisting essentially of the nucleotide sequence set forth in SEQ ID NO:1 (AAV4 genome). The present invention further provides an isolated nucleic acid that selectively hybridizes with an isolated nucleic acid comprising the nucleotide sequence set forth in SEQ ID NO:1 (AAV4 genome). By "selectively hybridizes" as used in the claims is meant a nucleic acid that specifically hybridizes to the particular target nucleic acid under sufficient stringency conditions to selectively hybridize to the target nucleic acid without significant background hybridization to a nucleic acid encoding an unrelated protein, and particularly, without detectably hybridizing to AAV2. Thus, a nucleic acid that selectively hybridizes with a nucleic acid of the present invention will not selectively hybridize under stringent conditions with a nucleic acid encoding a different protein, and vice versa. Therefore, nucleic acids for use, for example, as primers and probes to detect or amplify the target nucleic acids are contemplated herein. Nucleic acid fragments that selectively hybridize to any given nucleic acid can be used, e.g., as primers and or probes for further hybridization or for amplification methods (e.g., polymerase chain reaction (PCR), ligase chain reaction (LCR)). Additionally, for example, a primer or probe can be designed that selectively hybridizes with both AAV4 and a gene of interest carried within the AAV4 vector (i.e., a chimeric nucleic acid).

Stringency of hybridization is controlled by both temperature and salt concentration of either or both of the hybridization and washing steps. Typically, the stringency of hybridization to achieve selective hybridization involves hybridization in high ionic strength solution (6×SSC or 6×SSPE) at a temperature that is about 12-25° C. below the $T_m$ (the melting temperature at which half of the molecules dissociate from its partner) followed by washing at a combination of temperature and salt concentration chosen so that the washing temperature is about 5° C. to 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The washing temperatures can be used as described above to achieve selective stringency, as is known in the art. (Sambrook et al., *Molecular Cloning: A Laboratory Manual*, 2nd Ed., Cold Spring Harbor Laboratory, Cold Spring Harbor, N.Y., 1989; Kunkel et al. *Methods Enzymol.* 1987:154: 367, 1987). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as homology desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

A nucleic acid that selectively hybridizes to any portion of the AAV4 genome is contemplated herein. Therefore, a nucleic acid that selectively hybridizes to AAV4 can be of longer length than the AAV4 genome, it can be about the same length as the AAV4 genome or it can be shorter than the AAV4 genome. The length of the nucleic acid is limited on the shorter end of the size range only by its specificity for hybridization to AAV4, i.e., once it is too short, typically less than about 5 to 7 nucleotides in length, it will no longer bind specifically to AAV4, but rather will hybridize to numerous background nucleic acids. Additionally contemplated by this invention is a nucleic acid that has a portion that specifically hybridizes to AAV4 and a portion that specifically hybridizes to a gene of interest inserted within AAV4.

The present invention further provides an isolated nucleic acid encoding an adeno-associated virus 4 Rep protein. The AAV4 Rep proteins are encoded by open reading frame (ORF) 1 of the AAV4 genome. The AAV4 Rep genes are exemplified by the nucleic acid set forth in SEQ ID NO:3 (AAV4 ORF1), and include a nucleic acid consisting essentially of the nucleotide sequence set forth in SEQ ID NO:3 and a nucleic acid comprising the nucleotide sequence set forth in SEQ ID NO:3. The present invention also includes a nucleic acid encoding the amino acid sequence set forth in SEQ ID NO: 2 (polypeptide encoded by AAV4 ORF1). However, the present invention includes that the Rep genes nucleic acid can include any one, two, three, or four of the four Rep proteins, in any order, in such a nucleic acid. Furthermore, minor modifications are contemplated in the nucleic acid, such as silent mutations in the coding sequences, mutations that make neutral or conservative changes in the encoded amino acid sequence, and mutations in regulatory regions that do not disrupt the expression of the gene. Examples of other minor modifications are known in the art. Further modifications can be made in the nucleic acid, such as to disrupt or alter expression of one or more of the Rep proteins in order to, for example, determine the effect of such a disruption; such as to mutate one or more of the Rep proteins to determine the resulting effect, etc. However, in general, a modified nucleic acid encoding all four Rep proteins will have at least about 90%, about 93%, about 95%, about 98% or 100% homology to the sequence set forth in SEQ ID NO:3, and the Rep polypeptide encoded therein will have overall about 93%, about 95%, about 98%, about 99% or 100% homology with the amino acid sequence set forth in SEQ ID NO:2.

The present invention also provides an isolated nucleic acid that selectively hybridizes with a nucleic acid consisting essentially of the nucleotide sequence set forth in SEQ ID NO:3 and an isolated nucleic acid that selectively hybridizes with a nucleic acid comprising the nucleotide sequence set forth in SEQ ID NO:3. "Selectively hybridizing" is defined elsewhere herein.

The present invention also provides each individual AAV4 Rep protein and the nucleic acid encoding each. Thus the present invention provides the nucleic acid encoding a Rep 40 protein, and in particular an isolated nucleic acid comprising the nucleotide sequence set forth in SEQ ID NO:12, an isolated nucleic acid consisting essentially of the nucleotide sequence set forth in SEQ ID NO:12, and a nucleic acid encoding the adeno-associated virus 4 Rep protein having the amino acid sequence set forth in SEQ ID NO:8. The present invention also provides the nucleic acid encoding a Rep 52 protein, and in particular an isolated nucleic acid comprising the nucleotide sequence set forth in SEQ ID NO:13, an isolated nucleic acid consisting essentially of the nucleotide sequence set forth in SEQ ID NO:13, and a nucleic acid encoding the adeno-associated virus 4 Rep protein having the amino acid sequence set forth in SEQ ID NO:9. The present invention further provides the nucleic acid encoding a Rep 68 protein, and in particular an isolated nucleic acid comprising the nucleotide sequence set forth in SEQ ID NO:14, an isolated nucleic acid consisting essentially of the nucleotide sequence set forth in SEQ ID NO:14, and a nucleic acid encoding the adeno-associated virus 4 Rep protein having the amino acid sequence set forth in SEQ ID NO:10. And, further, the present invention provides the nucleic acid encoding a Rep 78 protein, and in particular an isolated nucleic acid comprising the nucleotide sequence set forth in SEQ ID NO:15, an isolated nucleic acid consisting essentially of the nucleotide sequence set forth in SEQ ID NO:15, and a nucleic acid encoding the adeno-associated virus 4 Rep protein having the amino acid sequence set forth in SEQ ID NO:11. As described elsewhere herein, these nucleic acids can have minor modifications, including silent nucleotide substitutions, mutations causing neutral amino acid substitutions in the encoded proteins, and mutations in control regions that do not or minimally affect the encoded amino acid sequence.

The present invention further provides a nucleic acid encoding the entire AAV4 Capsid polypeptide. Specifically, the present invention provides a nucleic acid having the nucleotide sequence set for the nucleotides 2260-4467 of SEQ ID NO:1. Furthermore, the present invention provides a nucleic acid encoding each of the three AAV4 coat proteins, VP1, VP2, and VP3. Thus, the present invention provides a nucleic acid encoding AAV4 VP1, a nucleic acid encoding AAV4 VP2, and a nucleic acid encoding AAV4 VP3. Thus, the present invention provides a nucleic acid encoding the amino acid sequence set forth in SEQ ID NO:4 (VP1); a nucleic acid encoding the amino acid sequence set forth in SEQ ID NO:16 (VP2), and a nucleic acid encoding the amino acid sequence set forth in SEQ ID NO:18 (VP3). The present invention also specifically provides a nucleic acid comprising SEQ ID NO:5 (VP1 gene); a nucleic acid comprising SEQ ID NO:17 (VP2 gene); and a nucleic acid comprising SEQ ID NO:19 (VP3 gene). The present invention also specifically provides a nucleic acid consisting essentially of SEQ ID NO:5 (VP1 gene), a nucleic acid consisting essentially of SEQ ID NO:17 (VP2 gene), and a nucleic acid consisting essentially of SEQ ID NO:19 (VP3 gene). Furthermore, a nucleic acid encoding an AAV4 capsid protein VP1 is set forth as nucleotides 2260-4467 of SEQ ID NO:1; a nucleic acid encoding an AAV4 capsid protein VP2 is set forth as nucleotides 2668-4467 of SEQ ID NO:1; and a nucleic acid encoding an AAV4 capsid protein VP3 is set forth as nucleotides 2848-4467 of SEQ ID NO:1. Minor modifications in the nucleotide sequences encoding the capsid, or coat, proteins are contemplated, as described above for other AAV4 nucleic acids.

The present invention also provides a cell containing one or more of the herein described nucleic acids, such as the AAV4 genome, AAV4 ORF1 and ORF2, each AAV4 Rep protein gene, and each AAV4 capsid protein gene. Such a cell can be any desired cell and can be selected based upon the use intended. For example, cells can include human HeLa cells, cos cells, other human and mammalian cells and cell lines. Primary cultures as well as established cultures and cell lines can be used. Nucleic acids of the present invention can be delivered into cells by any selected means, in particular depending upon the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art. Additionally, if in a viral particle, the cells can simply be transfected with the particle by standard means known in the art for AAV transfection.

The term "polypeptide" as used herein refers to a polymer of amino acids and includes full-length proteins and fragments thereof. Thus, "protein," polypeptide," and "peptide" are often used interchangeably herein. Substitutions can be selected by known parameters to be neutral (see, e.g., Robinson W E Jr, and Mitchell W M., AIDS 4:S151-S162 (1990)). As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations.

A polypeptide of the present invention can be readily obtained by any of several means. For example, polypeptide of interest can be synthesized mechanically by standard methods. Additionally, the coding regions of the genes can be expressed and the resulting polypeptide isolated by standard methods. Furthermore, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y., 1988), and the protein can be isolated from a cell expressing the nucleic acid encoding the polypeptide by selective hybridization with the antibody. This protein can be purified to the extent desired by standard methods of protein purification (see, e.g., Sambrook et al., *Molecular Cloning: A Laboratory Manual,* 2nd Ed., Cold Spring Harbor Laboratory, Cold Spring Harbor, N.Y., 1989).

Typically, to be unique, a polypeptide fragment of the present invention will be at least about 5 amino acids in length; however, unique fragments can be 6, 7, 8, 9, 10, 20, 30, 40, 50, 60, 70, 80, 90, 100 or more amino acids in length. A unique polypeptide will typically comprise such a unique fragment; however, a unique polypeptide can also be determined by its overall homology. A unique polypeptide can be 6, 7, 8, 9, 10, 20, 30, 40, 50, 60, 70, 80, 90, 100 or more amino acids in length. Uniqueness of a polypeptide fragment can readily be determined by standard methods such as searches of computer databases of known peptide or nucleic acid sequences or by hybridization studies to the nucleic acid encoding the protein or to the protein itself, as known in the art.

The present invention provides an isolated AAV4 Rep protein. AAV4 Rep polypeptide is encoded by ORF1 of AAV4. Specifically, the present invention provides an AAV4 Rep polypeptide comprising the amino acid sequence set forth in SEQ ID NO:2, or a unique fragment thereof. The present invention also provides an AAV4 Rep polypeptide consisting essentially of the amino acid sequence set forth in SEQ ID NO:2, or a unique fragment thereof. Additionally, nucleotides 291-2306 of the AAV4 genome, which genome is set forth in SEQ ID NO:1, encode the AAV4 Rep polypeptide. The present invention also provides each AAV4 Rep protein. Thus the present invention provides AAV4 Rep 40, or a unique fragment thereof. The present invention particularly provides Rep 40 having the amino acid sequence set forth in SEQ ID NO:8. The present invention provides AAV4 Rep 52, or a unique fragment thereof. The present invention particularly provides Rep 52 having the amino acid sequence set forth in SEQ ID NO:9. The present invention provides AAV4 Rep 68, or a unique fragment thereof. The present invention particularly provides Rep 68 having the amino acid sequence set forth in SEQ ID NO:10. The present invention provides AAV4 Rep 78, or a unique fragment thereof. The present invention particularly provides Rep 78 having the amino acid sequence set forth in SEQ ID NO:11. By "unique fragment thereof" is meant any smaller polypeptide fragment encoded by AAV rep gene that is of sufficient length to be unique to the Rep polypeptide. Substitutions and modifications of the amino acid sequence can be made as described above and, further, can include protein processing modifications, such as glycosylation, to the polypeptide. However, a polypeptide including all four Rep proteins will encode a polypeptide having at least about 91% overall homology to the sequence set forth in SEQ ID NO:2, and it can have about 93%, about 95%, about 98%, about 99% or 100% homology with the amino acid sequence set forth in SEQ ID NO:2.

The present invention further provides an AAV4 Capsid polypeptide or a unique fragment thereof. AAV4 capsid polypeptide is encoded by ORF 2 of AAV4. Specifically, the present invention provides an AAV4 Capsid protein comprising the amino acid sequence encoded by nucleotides 2260-4467 of the nucleotide sequence set forth in SEQ ID NO:1, or a unique fragment of such protein. The present invention also provides an AAV4 Capsid protein consisting essentially of the amino acid sequence encoded by nucleotides 2260-4467 of the nucleotide sequence set forth in SEQ ID NO:1, or a unique fragment of such protein. The present invention further provides the individual AAV4 coat proteins, VP1, VP2 and VP3.

Thus, the present invention provides an isolated polypeptide having the amino acid sequence set forth in SEQ ID NO:4 (VP1). The present invention additionally provides an isolated polypeptide having the amino acid sequence set forth in SEQ ID NO:16 (VP2). The present invention also provides an isolated polypeptide having the amino acid sequence set forth in SEQ ID NO:18 (VP3). By "unique fragment thereof" is meant any smaller polypeptide fragment encoded by any AAV4 capsid gene that is of sufficient length to be unique to the AAV4 Capsid protein. Substitutions and modifications of the amino acid sequence can be made as described above and, further, can include protein processing modifications, such as glycosylation, to the polypeptide. However, an AAV4 Capsid polypeptide including all three coat proteins will have at least about 63% overall homology to the polypeptide encoded by nucleotides 2260-4467 of the sequence set forth in SEQ ID NO: 1. The protein can have about 65%, about 70%, about 75%, about 80%, about 85%, about 90%, about 95% or even 100% homology to the amino acid sequence encoded by the nucleotides 2260-4467 of the sequence set forth in SEQ ID NO:4. An AAV4 VP2 polypeptide can have at least about 58%, about 60%, about 70%, about 80%, about 90% about 95% or about 100% homology to the amino acid sequence set forth in SEQ ID NO:16. An AAV4 VP3 polypeptide can have at least about 60%, about 70%, about 80%, about 90% about 95% or about 100% homology to the amino acid sequence set forth in SEQ ID NO:18.

The present invention further provides an isolated antibody that specifically binds AAV4 Rep protein. Also provided is an isolated antibody that specifically binds the AAV4 Rep protein having the amino acid sequence set forth in SEQ ID NO:2, or that specifically binds a unique fragment thereof. Clearly, any given antibody can recognize and bind one of a number of possible epitopes present in the polypeptide; thus only a unique portion of a polypeptide (having the epitope) may need to be present in an assay to determine if the antibody specifically binds the polypeptide.

The present invention additionally provides an isolated antibody that specifically binds any adeno-associated virus 4 Capsid protein or the polypeptide comprising all three AAV4 coat proteins. Also provided is an isolated antibody that specifically binds the AAV4 Capsid protein having the amino acid sequence set forth in SEQ ID NO:4, or that specifically binds a unique fragment thereof. The present invention further provides an isolated antibody that specifically binds the AAV4 Capsid protein having the amino acid sequence set forth in SEQ ID NO:16, or that specifically binds a unique fragment thereof. The invention additionally provides an isolated antibody that specifically binds the AAV4 Capsid protein having the amino acid sequence set forth in SEQ ID NO:18, or that specifically binds a unique fragment thereof. Again, any given antibody can recognize and bind one of a number of possible epitopes present in the polypeptide; thus only a unique portion of a polypeptide (having the epitope) may need to be present in an assay to determine if the antibody specifically binds the polypeptide.

The antibody can be a component of a composition that comprises an antibody that specifically binds the AAV4 protein. The composition can further comprise, e.g., serum, serum-free medium, or a pharmaceutically acceptable carrier such as physiological saline, etc.

By "an antibody that specifically binds" an AAV4 polypeptide or protein is meant an antibody that selectively binds to an epitope on any portion of the AAV4 peptide such that the antibody selectively binds to the AAV4 polypeptide, i.e., such that the antibody binds specifically to the corresponding AAV4 polypeptide without significant background. Specific binding by an antibody further means that the antibody can be used to selectively remove the target polypeptide from a sample comprising the polypeptide or and can readily be determined by radioimmunoassay (RIA), bioassay, or enzyme-linked immunosorbant (ELISA) technology. An ELISA method effective for the detection of the specific antibody-antigen binding can, for example, be as follows: (1) bind the antibody to a substrate; (2) contact the bound antibody with a sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change.

An antibody can include antibody fragments such as Fab fragments which retain the binding activity. Antibodies can be made as described in, e.g., Harlow and Lane, *Antibodies: A Laboratory Manual*, Cold Spring Harbor Laboratory, Cold Spring Harbor, N.Y. (1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. Individual hybridomas are then propagated as individual clones serving as a source for a particular monoclonal antibody.

The present invention additionally provides a method of screening a cell for infectivity by AAV4 comprising contacting the cell with AAV4 and detecting the presence of AAV4 in the cells. AAV4 particles can be detected using any standard physical or biochemical methods. For example, physical methods that can be used for this detection include 1) polymerase chain reaction (PCR) for viral DNA or RNA, 2) direct hybridization with labeled probes, 3) antibody directed against the viral structural or non-structural proteins. Catalytic methods of viral detection include, but are not limited to, detection of site and strand specific DNA nicking activity of Rep proteins or replication of an AAV origin-containing substrate. Additional detection methods are outlined in Fields, *Virology*, Raven Press, New York, N.Y. 1996.

For screening a cell for infectivity by AAV4 wherein the presence of AAV4 in the cells is determined by nucleic acid hybridization methods, a nucleic acid probe for such detection can comprise, for example, a unique fragment of any of the AAV4 nucleic acids provided herein. The uniqueness of any nucleic acid probe can readily be determined as described herein for unique nucleic acids. The nucleic acid can be, for example, the nucleic acid whose nucleotide sequence is set forth in SEQ ID NO: 1, 3, 5, 6, 7, 12, 13, 14, 15, 17 or 19, or a unique fragment thereof.

The present invention includes a method of determining the suitability of an AAV4 vector for administration to a subject comprising administering to an antibody-containing sample from the subject an antigenic fragment of an isolated AAV4 capsid protein, and detecting an antibody-antigen reaction in the sample, the presence of a reaction indicating the AAV4 vector to be unsuitable for use in the subject. The AAV4 capsid protein from which an antigenic fragment is selected can have the amino acid sequence set forth in SEQ ID NO:4. An immunogenic fragment of an isolated AAV4 capsid protein can also be used in these methods. The AAV4 capsid protein from which an antigenic fragment is selected can have the amino acid sequence set forth in SEQ ID NO:17. The AAV4 capsid protein from which an antigenic fragment is selected can have the amino acid sequence set forth in SEQ ID NO:19.

Alternatively, or additionally, an antigenic fragment of an isolated AAV4 Rep protein can be utilized in this determination method. An immunogenic fragment of an isolated AAV4 Rep protein can also be used in these methods. Thus the present invention further provides a method of determining the suitability of an AAV4 vector for administration to a subject comprising administering to an antibody-containing sample from the subject an antigenic fragment of an AAV4 Rep protein and detecting an antibody-antigen reaction in the sample, the presence of a reaction indicating the AAV4 vector to be unsuitable for use in the subject. The AAV4 Rep protein from which an antigenic fragment is selected can have the amino acid sequence set forth in SEQ ID NO:2. The AAV4 Rep protein from which an antigenic fragment is selected can have the amino acid sequence set forth in SEQ ID NO:8. The AAV4 Rep protein from which an antigenic fragment is selected can have the amino acid sequence set forth in SEQ ID NO:9. The AAV4 Rep protein from which an antigenic fragment is selected can have the amino acid sequence set forth in SEQ ID NO:10. The AAV4 Rep protein from which an antigenic fragment is selected can have the amino acid sequence set forth in SEQ ID NO:11.

An antigenic or immunoreactive fragment is typically an amino acid sequence of at least about 5 consecutive amino acids, and it can be derived from the AAV4 polypeptide amino acid sequence. An antigenic fragment is any fragment unique to the AAV4 protein, as described herein, against which an AAV4-specific antibody can be raised, by standard methods. Thus, the resulting antibody-antigen reaction should be specific for AAV4.

The AAV4 polypeptide fragments can be analyzed to determine their antigenicity, immunogenicity and/or specificity. Briefly, various concentrations of a putative immunogenically specific fragment are prepared and administered to a subject and the immunological response (e.g., the production of antibodies or cell mediated immunity) of an animal to each concentration is determined. The amounts of antigen administered depend on the subject, e.g. a human, rabbit or a guinea pig, the condition of the subject, the size of the subject, etc. Thereafter an animal so inoculated with the antigen can be exposed to the AAV4 viral particle or AAV4 protein to test the immunoreactivity or the antigenicity of the specific immunogenic fragment. The specificity of a putative antigenic or immunogenic fragment can be ascertained by testing sera, other fluids or lymphocytes from the inoculated animal for cross reactivity with other closely related viruses, such as AAV1, AAV2, AAV3 and AAV5.

As will be recognized by those skilled in the art, numerous types of immunoassays are available for use in the present invention to detect binding between an antibody and an AAV4 polypeptide of this invention. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988). For example, enzyme immunoassays such as immunofluorescence assays (IFA), enzyme linked immunosorbent assays (ELISA) and immunoblotting can be readily adapted to accomplish the detection of the antibody. An ELISA method effective for the detection of the antibody bound to the antigen can, for example, be as follows: (1) bind the antigen to a substrate; (2) contact the bound antigen with a fluid or tissue sample containing the antibody; (3) contact the above with a secondary antibody specific for the antigen and bound to a detectable moiety (e.g., horseradish peroxidase enzyme or alkaline phosphatase enzyme); (4) contact the above with the substrate for the enzyme; (5) contact the above with a color reagent; (6) observe color change.

The antibody-containing sample of this method can comprise any biological sample which would contain the antibody or a cell containing the antibody, such as blood, plasma, serum, bone marrow, saliva and urine.

By the "suitability of an AAV4 vector for administration to a subject" is meant a determination of whether the AAV4 vector will elicit a neutralizing immune response upon administration to a particular subject. A vector that does not elicit a significant immune response is a potentially suitable vector, whereas a vector that elicits a significant, neutralizing immune response is thus indicated to be unsuitable for use in that subject. Significance of any detectable immune response is a standard parameter understood by the skilled artisan in the field. For example, one can incubate the subject's serum with the virus, then determine whether that virus retains its ability to transduce cells in culture. If such virus cannot transduce cells in culture, the vector likely has elicited a significant immune response.

The present method further provides a method of delivering a nucleic acid to a cell comprising administering to the cell an AAV4 particle containing a vector comprising the nucleic acid inserted between a pair of AAV inverted terminal repeats, thereby delivering the nucleic acid to the cell. Administration to the cell can be accomplished by any means, including simply contacting the particle, optionally contained in a desired liquid such as tissue culture medium, or a buffered saline solution, with the cells. The particle can be allowed to remain in contact with the cells for any desired length of time, and typically the particle is administered and allowed to remain indefinitely. For such in vitro methods, the virus can be administered to the cell by standard viral transduction methods, as known in the art and as exemplified herein. Titers of virus to administer can vary, particularly depending upon the cell type, but will be typical of that used for AAV transduction in general. Additionally the titers used to transduce the particular cells in the present examples can be utilized. The cells can include any desired cell, such as the following cells and cells derived from the following tissues, in humans as well as other mammals, such as primates, horse, sheep, goat, pig, dog, rat, and mouse: Adipocytes, Adenocyte, Adrenal cortex, Amnion, Aorta, Ascites, Astrocyte, Bladder, Bone, Bone marrow, Brain, Breast, Bronchus, Cardiac muscle, Cecum, Cervix, Chorion, Colon, Conjunctiva, Connective tissue, Cornea, Dermis, Duodenum, Endometrium, Endothelium, Epithelial tissue, Epidermis, Esophagus, Eye, Fascia, Fibroblasts, Foreskin, Gastric, Glial cells, Glioblast, Gonad, Hepatic cells, Histocyte, Ileum, Intestine, small Intestine, Jejunum, Keratinocytes, Kidney, Larynx, Leukocytes, Lipocyte, Liver, Lung, Lymph node, Lymphoblast, Lymphocytes, Macrophages, Mammary alveolar nodule, Mammary gland, Mastocyte, Maxilla, Melanocytes, Monocytes, Mouth, Myelin, Nervous tissue, Neuroblast, Neurons, Neuroglia, Osteoblasts, Osteogenic cells, Ovary, Palate, Pancreas, Papilloma, Peritoneum, Pituicytes, Pharynx, Placenta, Plasma cells, Pleura, Prostate, Rectum, Salivary gland, Skeletal muscle, Skin, Smooth muscle, Somatic, Spleen, Squamous, Stomach, Submandibular gland, Submaxillary gland, Synoviocytes, Testis, Thymus, Thyroid, Trabeculae, Trachea, Turbinate, Umbilical cord, Ureter, and Uterus.

The AAV inverted terminal repeats in the vector for the herein described delivery methods can be AAV4 inverted terminal repeats. Specifically, they can comprise the nucleic acid whose nucleotide sequence is set forth in SEQ ID NO:6 or the nucleic acid whose nucleotide sequence is set forth in SEQ ID NO:20, or any fragment thereof demonstrated to have ITR functioning. The ITRs can also consist essentially of the nucleic acid whose nucleotide sequence is set forth in SEQ ID NO:6 or the nucleic acid whose nucleotide sequence is set forth in SEQ ID NO:20. Furthermore, the AAV inverted terminal repeats in the vector for the herein described nucleic acid delivery methods can also comprise AAV2 inverted terminal repeats. Additionally, the AAV inverted terminal repeats in the vector for this delivery method can also consist essentially of AAV2 inverted terminal repeats.

The present invention also includes a method of delivering a nucleic acid to a subject comprising administering to a cell from the subject an AAV4 particle comprising the nucleic acid inserted between a pair of AAV inverted terminal repeats, and returning the cell to the subject, thereby delivering the nucleic acid to the subject. The AAV ITRs can be any AAV ITRs, including AAV4 ITRs and AAV2 ITRs. For such an ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transfect the cells. Cells can then be transplanted back into the subject's body, again by means standard for the cell type and tissue (e. g., in general, U.S. Pat. No. 5,399,346; for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transfection by the virus, by known detection means and as described herein. Cells for ex vivo transfection followed by transplantation into a subject can be selected from those listed above, or can be any other selected cell. Preferably, a selected cell type is examined for its capability to be transfected by AAV4. Preferably, the selected cell will be a cell readily transduced with AAV4 particles; however, depending upon the application, even cells with relatively low transduction efficiencies can be useful, particularly if the cell is from a tissue or organ in which even production of a small amount of the protein or antisense RNA encoded by the vector will be beneficial to the subject.

The present invention further provides a method of delivering a nucleic acid to a cell in a subject comprising administering to the subject an AAV4 particle comprising the nucleic acid inserted between a pair of AAV inverted terminal repeats, thereby delivering the nucleic acid to a cell in the subject. Administration can be an ex vivo administration directly to a cell removed from a subject, such as any of the cells listed above, followed by replacement of the cell back into the subject, or administration can be in vivo administration to a cell in the subject. For ex vivo administration, cells are isolated from a subject by standard means according to the cell type and placed in appropriate culture medium, again according to cell type (see, e.g., ATCC catalog). Viral particles are then contacted with the cells as described above, and the virus is allowed to transfect the cells. Cells can then be transplanted back into the subject's body, again by means standard for the cell type and tissue (e.g., for neural cells, Dunnett, S. B. and Björklund, A., eds., *Transplantation: Neural Transplantation—A Practical Approach*, Oxford University Press, Oxford (1992)). If desired, prior to transplantation, the cells can be studied for degree of transfection by the virus, by known detection means and as described herein.

In vivo administration to a human subject or an animal model can be by any of many standard means for administering viruses, depending upon the target organ, tissue or cell. Virus particles can be administered orally, parenterally (e.g., intravenously), by intramuscular injection, by direct tissue or organ injection, by intraperitoneal injection, topically, transdermally, or the like. Viral nucleic acids (non-encapsidated) can be administered, e.g., as a complex with cationic liposomes, or encapsulated in anionic liposomes. Compositions can include various amounts of the selected viral particle or non-encapsidated viral nucleic acid in combination with a pharmaceutically acceptable carrier and, in addition, if desired, may include other medicinal agents, pharmaceutical agents, carriers, adjuvants, diluents, etc. Parental administration, if used, is generally characterized by injection. Injectables can be prepared in conventional forms, either as liquid solutions or suspensions, solid forms suitable for solution or suspension in liquid prior to injection, or as emulsions. Dosages will depend upon the mode of administration, the disease or condition to be treated, and the individual subject's condition, but will be that dosage typical for and used in administration of other AAV vectors, such as AAV2 vectors. Often a single dose can be sufficient; however, the dose can be repeated if desirable.

The present invention further provides a method of delivering a nucleic acid to a cell in a subject having antibodies to AAV2 comprising administering to the subject an AAV4 particle comprising the nucleic acid, thereby delivering the nucleic acid to a cell in the subject. A subject that has antibodies to AAV2 can readily be determined by any of several known means, such as contacting AAV2 protein(s) with an antibody-containing sample, such as blood, from a subject and detecting an antigen-antibody reaction in the sample. Delivery of the AAV4 particle can be by either ex vivo or in vivo administration as herein described. Thus, a subject who might have an adverse immunogenic reaction to a vector administered in an AAV2 viral particle can have a desired nucleic acid delivered using an AAV4 particle. This delivery system can be particularly useful for subjects who have received therapy utilizing AAV2 particles in the past and have developed antibodies to AAV2. An AAV4 regimen can now be substituted to deliver the desired nucleic acid.

Statement of Utility

The present invention provides recombinant vectors based on AAV4. Such vectors may be useful for transducing erythroid progenitor cells which is very inefficient with AAV2 based vectors. In addition to transduction of other cell types, transduction of erythroid cells would be useful for the treatment of cancer and genetic diseases which can be corrected by bone marrow transplants using matched donors. Some examples of this type of treatment include, but are not limited to, the introduction of a therapeutic gene such as genes encoding interferons, interleukins, tumor necrosis factors, adenosine deaminase, cellular growth factors such as lymphokines, blood coagulation factors such as factor VIII and IX, cholesterol metabolism uptake and transport protein such as EpoE and LDL receptor, and antisense sequences to inhibit viral replication of, for example, hepatitis or HIV.

The present invention provides a vector comprising the AAV4 virus as well as AAV4 viral particles. While AAV4 is similar to AAV2, the two viruses are found herein to be physically and genetically distinct. These differences endow AAV4 with some unique advantages which better suit it as a vector for gene therapy. For example, the wt AAV4 genome is larger than AAV2, allowing for efficient encapsidation of a larger recombinant genome. Furthermore, wt AAV4 particles have a greater buoyant density than AAV2 particles and therefore are more easily separated from contaminating helper virus and empty AAV particles than AAV2-based particles.

Furthermore, as shown herein, AAV4 capsid protein is distinct from AAV2 capsid protein and exhibits different tissue tropism. AAV2 and AAV4 are shown herein to utilize distinct cellular receptors. AAV2 and AAV4 have been shown to be serologically distinct and thus, in a gene therapy application, AAV4 would allow for transduction of a patient who already possesses neutralizing antibodies to AAV2 either as a result of natural immunological defense or from prior exposure to AAV2 vectors.

The present invention is more particularly described in the following examples which are intended as illustrative only since numerous modifications and variations therein will be apparent to those skilled in the art.

EXAMPLES

To understand the nature of AAV4 virus and to determine its usefulness as a vector for gene transfer, it was cloned and sequenced.

Cell Culture and Virus Propagation

Cos and HeLa cells were maintained as monolayer cultures in D10 medium (Dulbecco's modified Eagle's medium containing 10% fetal calf serum, 100 µg/ml penicillin, 100 units/ml streptomycin and IX Fungizone as recommended by the manufacturer; (GIBCO, Gaithersburg, Md., USA). All other cell types were grown under standard conditions which have been previously reported. AAV4 stocks were obtained from American Type Culture Collection #VR-64 6.

Virus was produced as previously described for AAV2, using the Beta galactosidase vector plasmid and a helper plasmid containing the AAV4 Rep and Cap genes (9). The helper plasmid was constructed in such a way as not to allow any homologous sequence between the helper and vector plasmids. This step was taken to minimize the potential for wild-type (wt) particle formation by homologous recombination.

Virus was isolated from $5 \times 10^7$ cos cells by CsCl banding (9), and the distribution of Beta galactosidase genomes across the genome was determined by DNA dot blots of aliquots of gradient fractions. The majority of packaged genomes were found in fractions with a density of 1.43 which is similar to that reported for wt AAV4. This preparation of virus yielded $2.5 \times 10^{11}$ particles or 5000 particles/producer cell. In comparison AAV2 isolated and CsCl banded from $8 \times 10^7$ cells yielded $1.2 \times 10^{11}$ particles or 1500 particles/producer cell. Thus, typical yields of rAAV4 particles/producer cell were 3-5 fold greater than that of rAAV2 particles.

DNA Cloning and Sequencing and Analysis

In order to clone the genome of AAV4, viral lysate was amplified in cos cells and then HeLa cells with the resulting viral particles isolated by CsCl banding. DNA dot blots of aliquots of the gradient fractions indicated that peak genomes were contained in fractions with a density of 1.41-1.45. This is very similar to the buoyant density previously reported for AAV4 (29). Analysis of annealed DNA obtained from these fractions indicated a major species of 4.8 kb in length which upon restriction analysis gave bands similar in size to those previously reported. Additional restriction analysis indicated the presence of BssHII restriction sites near the ends of the DNA. Digestion with BssHII yielded a 4.5 kb fragment which was then cloned into Bluescript SKII+ and two independent clones were sequenced.

The viral sequence is now available through Genebank, accession number U89790. DNA sequence was determined using an ABI 373A automated sequencer and the FS dye terminator chemistry. Both strands of the plasmids were sequenced and confirmed by sequencing of a second clone.

As further confirmation of the authenticity of the sequence, bases 91-600 were PCR amplified from the original seed material and directly sequenced. The sequence of this region, which contains a 56 base insertion compared to AAV2 and 3, was found to be identical to that derived from the cloned material. The ITR was cloned using Deep Vent Polymerase (New England Biolabs) according to the manufactures instructions using the following primers, primer 1: 5'CTAGTCTAGACTTGGCCACTCCCTCTCTGCGCG (SEQ ID NO:21); primer 2: 5'AGGCCTTAAGAG-CAGTCGTCCACCACCTTGTTCC (SEQ ID NO:22). Cycling conditions were 97° C. 20 sec, 65° C. 30 sec, 75° C. 1 min for 35 rounds. Following the PCR reaction, the mixture was treated with XbaI and EcoRI endonucleases and the amplified band purified by agarose gel electrophoresis. The recovered DNA fragment was ligated into Bluescript SKII+ (Stratagene) and transformed into competent Sure strain bacteria (Stratagene). The helper plasmid (pSV40oriAAV$_{4-2}$) used for the production of recombinant virus, which contains the rep and cap genes of AAV4, was produced by PCR with Pfu polymerase (Stratagene) according to the manufactures instructions. The amplified sequence, nt 216-4440, was ligated into a plasmid that contains the SV40 origin of replication previously described (9, 10). Cycling conditions were 95° C. 30 sec, 55° C. 30 sec, 72° C. 3 min for 20 rounds. The final clone was confirmed by sequencing. The βgal reporter vector has been described previously (9, 10).

Sequencing of this fragment revealed two open reading frames (ORF) instead of only one as previously suggested. In addition to the previously identified Capsid ORF in the right-hand side of the genome, an additional ORF is present on the left-hand side. Computer analysis indicated that the left-hand ORF has a high degree of homology to the Rep gene of AAV2. At the amino acid level the ORF is 90% identical to that of AAV2 with only 5% of the changes being non-conserved (SEQ ID NO:2). In contrast, the right ORF is only 62% identical at the amino acid level when compared to the corrected AAV2 sequence. While the internal start site of VP2 appears to be conserved, the start site for VP3 is in the middle of one of the two blocks of divergent sequence. The second divergent block is in the middle of VP3. By using three dimensional structure analysis of the canine parvovirus and computer aided sequence comparisons, regions of AAV2 which might be exposed on the surface of the virus have been identified. Comparison of the AAV2 and AAV4 sequences indicates that these regions are not well conserved between the two viruses and suggests altered tissue tropism for the two viruses.

Comparison of the p5 promoter region of the two viruses shows a high degree of conservation of known functional elements (SEQ ID NO:7). Initial work by Chang et al. identified two YY1 binding sites at −60 and +1 and a TATA Box at −30 which are all conserved between AAV2 and AAV4 (4). A binding site for the Rep has been identified in the p5 promoter at −17 and is also conserved (24). The only divergence between the two viruses in this region appears to be in the sequence surrounding these elements. AAV4 also contains an additional 56 bases in this region between the p5 promoter and the TRS (nt 209-269). Based on its positioning in the viral genome and efficient use of the limited genome space, this sequence may possess some promoter activity or be involved in rescue, replication or packaging of the virus.

The inverted terminal repeats were cloned by PCR using a probe derived from the terminal resolution site (TRS) of the BssHII fragment and a primer in the Rep ORF. The TRS is a sequence at the end of the stem of the ITR and the reverse compliment of TRS sequence was contained within the BssHII fragment. The resulting fragments were cloned and found to contain a number of sequence changes compared to AAV2. However, these changes were found to be complementary and did not affect the ability of this region to fold into a hairpin structure (FIG. 2). While the TRS site was conserved between AAV2 and AAV4 the Rep binding site contained two alterations which expand the binding site from 3 GAGC repeats to 4. The first two repeats in AAV4 both contain a T in the fourth position instead of a C. This type of repeat is present in the p5 promoter and is present in the consensus sequence that has been proposed for Rep binding (10) and its expansion may affect its affinity for Rep. Methylation interference data has suggested the importance of the CTTTG motif found at the tip of one palindrome in Rep binding with the underlined T residues clearly affecting Rep binding to both the flip and flop forms. While most of this motif is conserved in AAV4 the middle T residue is changed to a C (33).

Hemagglutination Assays

Hemagglutination was measured essentially as described previously (18). Serial two fold dilutions of virus in Veronal-buffered saline were mixed with an equal volume of 0.4% human erythrocytes (type 0) in plastic U bottom 96 well plates. The reaction was complete after a 2 hr incubation at 8° C. HA units (HAU) are defined as the reciprocal of the dilution causing 50% hemagglutination.

The results show that both the wild type and recombinant AAV4 viruses can hemagglutinate human red blood cells (RBCS) with HA titers of approximately 1024 HAU/μl and 512 HAU/μl respectively. No HA activity was detected with AAV type 3 or recombinant AAV type 2 as well as the helper adenovirus. If the temperature was raised to 22° C., HA activity decreased 32-fold. Comparison of the viral particle number per RBC at the end point dilution indicated that approximately 1-10 particles per RBC were required for hemagglutination. This value is similar to that previously reported (18).

Tissue Tropism Analysis

The sequence divergence in the capsid proteins ORF which are predicted to be exposed on the surface of the virus may result in an altered binding specificity for AAV4 compared to AAV2. Very little is known about the tissue tropism of any dependovirus. While it had been shown to hemagglutinate human, guinea pig, and sheep erythrocytes, it is thought to be exclusively a simian virus (18). Therefore, to examine AAV4 tissue tropism and its species specificity, recombinant AAV4 particles which contained the gene for nuclear localized Beta galactosidase were constructed. Because of the similarity in genetic organization of AAV4 and AAV2, it was determined whether AAV4 particles could be constructed containing a recombinant genome. Furthermore, because of the structural similarities of the AAV type 2 and type 4 ITRs, a genome containing AAV2 ITRs which had been previously described was used.

Tissue tropism analysis 1. To study AAV transduction, a variety of cell lines were transduced with 5 fold serial dilutions of either recombinant AAV2 or AAV4 particles expressing the gene for nuclear localized Beta galactosidase activity (Table 1). Approximately $4 \times 10^4$ cells were exposed to virus in 0.5 ml serum free media for 1 hour and then 1 ml of the appropriate complete media was added and the cells were incubated for 48-60 hours. The cells were then fixed and stained for β-galactosidase activity with 5-Bromo-4-Chloro-3-Indolyl-β-D-galactopyranoside (Xgal) (ICN Biomedicals) (36). Biological titers were determined by counting the number of positive cells in the different dilutions using a calibrated microscope ocular (3.1 mm$^2$) then multiplying by the area of the well and the dilution of the virus. Typically dilutions which gave 1-10 positive cells per field (100-1000 positive cells per 2 cm well) were used for titer determination. Titers were determined by the average number of cells in a minimum of 10 fields/well.

To examine difference in tissue tropism, a number of cell lines were transduced with serial dilutions of either AAV4 or AAV2 and the biological titers determined. As shown in Table 1, when Cos cells were transduced with a similar number of viral particles, a similar level of transduction was observed with AAV2 and AAV4. However, other cell lines exhibited differential transducibility by AAV2 or AAV4. Transduction of the human colon adenocarcinoma cell line SW480 with AAV2 was over 100 times higher than that obtained with AAV4. Furthermore, both vectors transduced SW1116, SW1463 and NIH3T3 cells relatively poorly.

TABLE 1

| Cell type | AAV2 | AAV4 |
|---|---|---|
| Cos | $4.5 \times 10^7$ | $1.9 \times 10^7$ |
| SW 480 | $3.8 \times 10^6$ | $2.8 \times 10^4$ |
| SW 1116 | $5.2 \times 10^4$ | $8 \times 10^3$ |
| SW1463 | $8.8 \times 10^4$ | $8 \times 10^3$ |
| SW620 | $8.8 \times 10^4$ | ND |
| NIH 3T3 | $2 \times 10^4$ | $8 \times 10^3$ |

Tissue Tropism Analysis 2.
A. Transduction of cells. Exponentially growing cells ($2 \times 10^4$) were plated in each well of a 12 well plate and transduced with serial dilutions of virus in 200 µl of medium for 1 hr. After this period, 800 µl of additional medium was added and incubated for 48 hrs. The cells were then fixed and stained for β-galactosidase activity overnight with 5-bromo-4-chloro-3-indolyl-β-D-galactopyranoside (Xgal) (ICN Biomedicals) (36). No endogenous β-galactosidase activity was visible after 24 hr incubation in Xgal solution. Infectious titers were determined by counting the number of positive cells in the different dilutions using a calibrated microscope ocular (diameter 3.1 mm²) then multiplying by the area of the well and the dilution of the virus. Titers were determined by the average number of cells in a minimum of 10 fields/well.

As shown in Table 2, cos cells transduced with equivalent amounts of rAAV2 and rAAV4 particles resulted in similar transduction levels. However, other cell lines exhibited differential transducibility. Transduction of the human colon adenocarcinoma cell line, SW480, with rAAV2 was 60 times higher than that obtained with rAAV4. HeLa and SW620 cells were also transduced more efficiently with rAAV2 than rAAV4. In contrast, transduction of primary rat brain cultures exhibited a greater transduction of glial and neuronal cells with rAAV4 compared to rAAV2. Because of the heterogeneous nature of the cell population in the rat brain cultures, only relative transduction efficiencies are reported (Table 2).

As a control for adenovirus contamination of the viral preparations cos and HeLa cells were coinfected with RAAV and adenovirus then stained after 24 hr. While the titer of rAAV2 increased in the presence of Ad in both cos and HeLa, adenovirus only increased the titer in the cos cells transduced with rAAV4 and not the HeLa cells, suggesting the difference in transduction efficiencies is not the result of adenovirus contamination. Furthermore, both vectors transduced SW1116, SW1463, NIH3T3 and monkey fibroblasts FL2 cells very poorly. Thus AAV4 may utilize a cellular receptor distinct from that of AAV2.

TABLE 2

| CELL TYPE | AAV2 | AAV4 |
|---|---|---|
| Primary Rat Brain | 1 | $4.3 \cdot 0.7$ |
| cos | $4.2 \times 10^7 \cdot 4.6 \times 10^6$ | $2.2 \times 10^7 \cdot 2.5 \times 10^6$ |
| SW 480 | $7.75 \times 10^6 \cdot 1.7 \times 10^6$ | $1.3 \times 10^5 \cdot 6.8 \times 10^4$ |
| HeLa | $2.1 \times 10^7 \cdot 1 \times 10^6$ | $1.3 \times 10^6 \cdot 1 \times 10^5$ |
| SW620 | $1.2 \times 10^5 \cdot 3.9 \times 10^4$ | $4 \times 10^4$ |
| KLEB | $1.2 \times 10^5 \cdot 3.5 \times 10^4$ | $9 \times 10^4 \cdot 1.4 \times 10^4$ |
| HB | $5.6 \times 10^5 \cdot 2 \times 10^5$ | $3.8 \times 10^4 \cdot 1.8 \times 10^4$ |
| SW1116 | $5.2 \times 10^4$ | $8 \times 10^3$ |
| SW1463 | $8.8 \times 10^4$ | $8 \times 10^3$ |
| NIH 3T3 | $3 \times 10^3$ | $2 \times 10^3$ |

B. Competition assay. Cos cells were plated at $2 \times 10^4$/well in 12 well plates 12-24 hrs prior to transduction. Cells were transduced with $0.5 \times 10^7$ particles of rAAV2 or rAAV4 (containing the LacZ gene) in 200 µl of DMEM and increasing amounts of rAAV2 containing the gene for the human coagulation factor IX. Prior to transduction the CsCl was removed from the virus by dialysis against isotonic saline. After 1 hr incubation with the recombinant virus the culture medium was supplemented with complete medium and allowed to incubate for 48-60 hrs. The cells were then stained and counted as described above.

Figure 3:
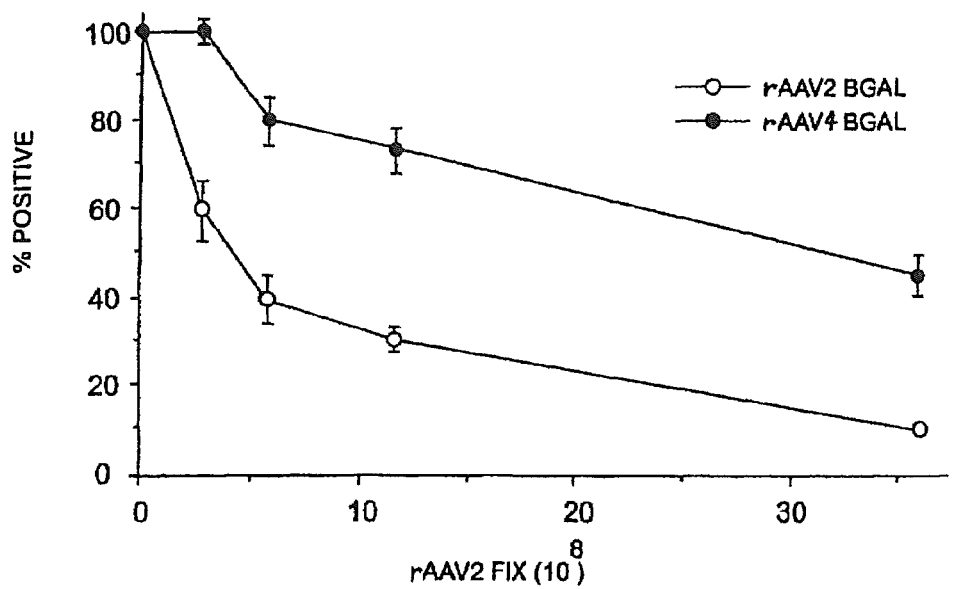
FIG. 3 shows cotransduction of rAAV2 and rAAV4. Cos cells were transduced with a constant amount of rAAV2 or rAAV4 expressing beta galactosidase and increasing amounts of rAAV2 expressing human factor IX (rAAV2FIX). For the competition the number of positive cells detected in the cotransduced wells was divided by the number of positive cells in the control wells (cells transduced with only rAAV2LacZ or rAAV4LacZ) and expressed as a percent of the control. This value was plotted against the number of particles of rAAV2FIX.

AAV4 utilization of a cellular receptor distinct from that of AAV2 was further examined by cotransduction experiments with rAAV2 and rAAV4. Cos cells were transduced with an equal number of rAAV2 or rAAV4 particles containing the LacZ gene and increasing amounts of rAAV2 particles containing the human coagulation factor IX gene (rAAV2FIX). At a 72:1 ratio of rAAV2FIX:rAAV4LacZ only a two-fold effect on the level of rAAV4LacZ transduction was obtained (FIG. 3). However this same ratio of rAAV2FIX:rAAV2LacZ reduced the transduction efficiency of rAAV2LacZ approximately 10 fold. Comparison of the 50% inhibition points for the two viruses indicated a 7 fold difference in sensitivity.

C. Trypsinization of cells. An 80% confluent monolayer of cos cells ($1 \times 10^7$) was treated with 0.05% trypsin/0.02% versene solution (Biofluids) for 3-5 min at 37° C. Following detachment the trypsin was inactivated by the addition of an equal volume of media containing 10% fetal calf serum. The cells were then further diluted to a final concentration of $1 \times 10^4$/ml. One ml of cells was plated in a 12 well dish and incubated with virus at a multiplicity of infection (MOI) of 260 for 1-2 hrs. Following attachment of the cells the media containing the virus was removed, the cells washed and fresh media was added. Control cells were plated at the same time but were not transduced until the next day. Transduction conditions were done as described above for the trypsinized cell group. The number of transduced cells was determined by staining 48-60 hrs post transduction and counted as described above.

Figure 4:
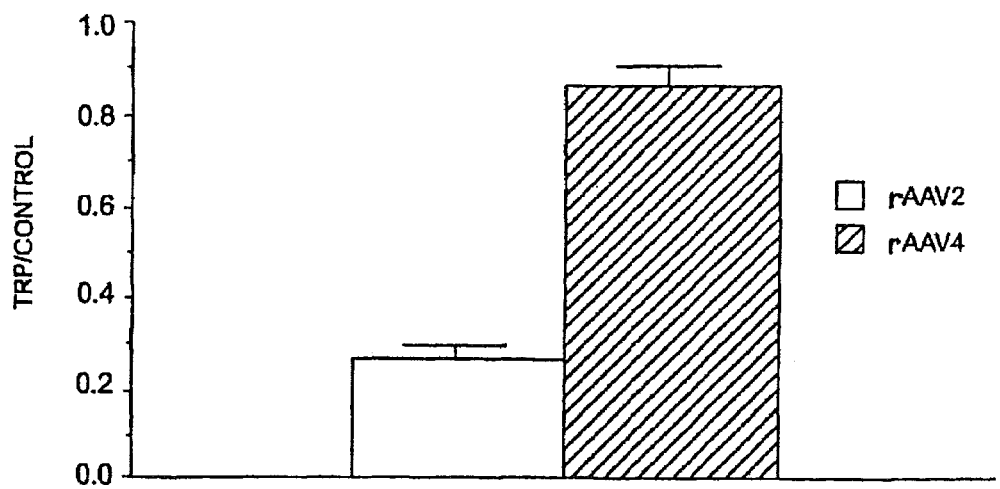
FIG. 4 shows effect of trypsin treatment on cos cell transduction. Cos cell monolayers were trypsinized and diluted in complete media. Cells were incubated with virus at an MOI of 260 and following cell attachment the virus was removed. As a control an equal number of cos cells were plated and allowed to attach overnight before transduction with virus for the same amount of time. The number of positive cells was determined by staining 50 hrs post transduction. The data is presented as a ratio of the number of positive cells seen with the trypsinized group and the control group.

Previous research had shown that binding and infection of AAV2 is inhibited by trypsin treatment of cells (26). Transduction of cos cells with rAAV21acZ gene was also inhibited by trypsin treatment prior to transduction (FIG. 4). In contrast trypsin treatment had a minimal effect on rAAV41acZ transduction. This result and the previous competition experiment are both consistent with the utilization of distinct cellular receptors for AAV2 and AAV4.

AAV4 is a distinct virus based on sequence analysis, physical properties of the virion, hemagglutination activity, and tissue tropism. The sequence data indicates that AAV4 is a distinct virus from that of AAV2. In contrast to original reports, AAV4 contains two open reading frames which code for either Rep proteins or Capsid proteins. AAV4 contains additional sequence upstream of the p5 promoter which may affect promoter activity, packaging or particle stability. Furthermore, AAV4 contains an expanded Rep binding site in its ITR which could alter its activity as an origin of replication or promoter. The majority of the differences in the Capsid proteins lies in regions which have been proposed to be on the exterior surface of the parvovirus. These changes are most likely responsible for the lack of cross reacting antibodies, hemagglutinate activity, and the altered tissue tropism compared to AAV2. Furthermore, in contrast to previous reports AAV4 is able to transduce human as well as monkey cells.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

References:
1. Arella, M., S. Garzon, J. Bergeron, and P. Tijssen. *Handbook of Parvoviruses*. Vol. 1. ed. P. Tijssen. Boca Raton, Fla., CRC Press, 1990.
2. Bachmann, P. A., M. D. Hoggan, E. Kurstak, J. L. Melnick, H. G. Pereira, P. Tattersall, and C. Vago. 1979. Interverology 11: 248-254.
3. Bantel-Schaal, U. and M. Stohr. 1992. J. Virol. 66: 773-779.
4. Chang, L. S., Y. Shi, and T. Shenk. 1989. J. Virol. 63: 3479-88.
5. Chejanovsky, N. and B. J. Carter. 1989. Virology 173: 120-128.
6. Chejanovsky, N. and B. J. Carter. 1989. Virology 171: 239-247.
7. Chiorini, J. A., S. M. Wiener, R. M. Kotin, R. A. Owens, SRM Kyöstiö, and B. Safer. 1994. J. Virol. 68: 7448-7457.
8. Chiorini, J. A., M. D. Weitzman, R. A. Owens, E. Urcelay, B. Safer, and R. M. Kotin. 1994. J. Virol. 68: 797-804.
9. Chiorini, J. A., C. M. Wendtner, E. Urcelay, B. Safer, M. Hallek, and R. M. Kotin. 1995. Human Gene Therapy 6: 1531-1541.
10. Chiorini, J. A., L. Yang, B. Safer, and R. M. Kotin. 1995. J. Virol. 69: 7334-7338.
11. Dixit, M., M. S. Webb, W. C. Smart, and S. Ohi. 1991. Gene 104: 253-7.
12. Fisher, R. E. and H. D. Mayor. 1991. J Theor Biol 149: 429-39.
13. Flotte, T. R., S. A. Afione, C. Conrad, S. A. McGrath, R. Solow, H. Oka, P. L. Zeitlin, W. B. Guggino, and B. J. Carter. 1993. Proc. Natl. Acad. Sci. 90: 10613-10617.
14. Flotte, T. R., S. A. Afione, R. Solow, M. L. Drumm, D. Markakis, W. B. Guggino, P. L. Zeitlin, and B. J. Carter. 1993. J Biol Chem 268: 3781-90.
15. Hermonat, P. L., M. A. Labow, R. Wright, K. I. Berns, and N. Muzyczka. 1984. J. Virol. 51: 329-339.
16. Hermonat, P. L. and N. Muzyczka. 1984. Proc Natl Acad Sci USA 81: 6466-70.
17. Hunter, L. A. and R. J. Samulski. 1992. J. Virol. 66: 317-24.
18. Ito, M. and H. D. Mayor. 1968. J. Immuno. 100: 61-68.
19. Janik, J. E., M. M. Huston, K. Cho, and J. A. Rose. 1989. Virology 168: 320-9.
20. Kaplitt, M. G., P. Leone, R. J. Samulski, X. Xiao, D. W. Pfaff, K. L. O'Malley, and J. M. During. 1994. Nature Genetics 8: 148-154.
21. Kotin, R. M., M. Siniscalco, R. J. Samulski, X. Zhu, L. Hunter, C. A. Laughlin, S. McLaughlin, N. Muzyczka, M. Rocchi, and K. I. Berns. 1990. Proc. Natl. Acad. Sci. (USA) 87: 2211-2215.
22. Laughlin, C. A., N. Jones, and B. J. Carter. 1982. J. Virol. 41: 868-76.
23. Laughlin, C. A., M. W. Myers, D. L. Risin, B. J. Carter. 1979. Virology 94: 162-74.
24. McCarty, D. M., J. Pereira, I. Zolotukhin, X. Zhou, J. H. Ryan, and N. Muzyczka. 1994. J. Virol. 68: 4988-4997.
25. Mendelson, E., J. P. Trempe, and B. J. Carter. 1986. J. Virol. 60: 823-832.
26. Mizukami, H., N. S. Young, and K. E. Brown. 1996. Virology 217: 124-130.
27. Muster, C. J., Y. S. Lee, J. E. Newbold, and J. Leis. 1980. J. Virol. 35: 653-61.
28. Muzyczka, N. 1992. Curr Top Microbiol Immunol 158: 97-129.
29. Parks, W. P., J. L. Melnick, R. Rongey, and H. D. Mayor. 1967. J. Virol. 1: 171-180.
30. Podsakoff, G., K. K. Jr Wong, and S. Chatterjee. 1994. J. Virol. 68: 5656-5666.
31. Rose, J. A., M. D. Hoggan, F. Koczot, and A. J. Shatkin. 1968. J. Virol. 2: 999-1005.
32. Russell, D. W., A. D. Miller, and I. E. Alexander. 1994. Proc. Natl. Acad. Sci. USA 91: 8915-8919.
33. Ryan, J. H., S. Zolotukhin, and N. Muzyczka. 1996. J. Virol. 70: 1542-1553.
34. Samulski, R. J., K. I. Berns, M. Tan, and N. Muzyczka. 1982. Proc Natl Acad Sci USA 79: 2077-81.
35. Samulski, R. J., L. S. Chang, and T. Shenk. 1989. J. Virol. 63: 3822-8.
36. Sanes, J. R., J. L. R. Rubenstein, and J. F. Nicocas. 1986. EMBO 5: 3133-3142.
37. Senaphthy, P., J. D. Tratschin, and B. J. Carter. 1984. J Mol Biol 179: 1-20.
38. Tratschin, J. D., I. L. Miller, and B. J. Carter. 1984. J. Virol. 51: 611-619.
39. Trempe, J. P. and B. J. Carter. 1988. J. Virol. 62: 68-74.
40. Trempe, J. P., E. Mendelson, and B. J. Carter. 1987. Virology 161: 18-28.
41. Walsh, C. E., J. M. Liu, X. Xiao, N. S. Young, A. W. Nienhuis, and R. J. Samulski. 1992. Proc Natl Acad Sci USA 89: 7257-61.
42. Winocour, E., M. F. Callaham, and E. Huberman. 1988. Virology 167: 393-9.

What is claimed is:

1. A vector system for producing infectious virus particles having a characteristic of AAV4 comprising: at least one vector comprising an isolated nucleic acid sequence encoding an AAV4 capsid protein comprising an amino acid sequence at least 80% identical to SEQ ID NO:4, SEQ ID NO:16 or SEQ ID NO:18, wherein the AAV4 capsid protein is capable of forming a virus particle.

2. The vector system of claim 1 comprising a second vectors.

3. The vector system of claim 2, wherein the first vector comprises a nucleic acid sequence encoding an AAV4 Rep protein comprising an amino acid sequence at least 80% identical to SEQ ID NO:2, SEQ ID NO:8, SEQ ID NO:9, SEQ ID NO:10 or SEQ ID NO:11, wherein the AAV4 Rep protein has Rep protein activity, and the second vector comprises a pair of AAV inverted terminal repeats.

4. The vector system of claim 2, wherein the first vector comprises a nucleic acid sequence encoding a second protein comprising an amino acid sequence at least 80% identical to SEQ ID NO:8, SEQ ID NO:9, SEQ ID NO:10 or SEQ ID NO:11, wherein the second protein has Rep protein activity, and the second vector comprises a pair of AAV inverted terminal repeats.

5. The vector system according to claim 3, wherein the second vector comprises a pair of AAV2 inverted terminal repeats.

6. The vector system according to claim 3, wherein the second vector comprises a pair of AAV3 inverted terminal repeats.

7. The vector system according to claim 3, wherein the second vector comprises a pair of AAV4 inverted terminal repeats.

8. The vector system according to claim 7, wherein the AAV4 inverted terminal repeats comprise a Rep protein binding site having four "GAGC" repeats, wherein in the fourth nucleotide in the first two "GAGC" repeats is a T rather than a C.

9. The vector system according to claim 8, wherein the AAV4 inverted terminal repeats comprise the nucleotide sequence set forth in SEQ ID NO:6.

10. The vector system according to claim 8, wherein the AAV4 inverted terminal repeats comprise the nucleotide sequence set forth in SEQ ID NO:20.

11. The vector system according to claim 3, wherein the second vector comprises a pair of AAV5 inverted terminal repeats.

12. The vector system of claim 4, wherein the adeno-associated virus 4 Rep protein has about 95% homology with the amino acid sequence set forth in SEQ ID NO:2.

13. The vector system of claim 4, wherein the adeno-associated virus 4 Rep protein has the amino acid sequence set forth in SEQ ID NO:8.

14. The vector system of claim 4, wherein the adeno-associated virus 4 Rep protein has about 95% homology with the amino acid sequence set forth in SEQ ID NO:8.

15. The vector system of claim 4, wherein the adeno-associated virus 4 Rep protein has the amino acid sequence set forth in SEQ ID NO:9.

16. The vector system of claim 4, wherein the adeno-associated virus 4 Rep protein has about 95% homology with the amino acid sequence set forth in SEQ ID NO:9

17. The vector system of claim 4, wherein the adeno-associated virus 4 Rep protein has the amino acid sequence set forth in SEQ ID NO:10.

18. The vector system of claim 4, wherein the adeno-associated virus 4 Rep protein has about 95% homology with the amino acid sequence set forth in SEQ ID NO:10.

19. The vector system of claim 4, wherein the adeno-associated virus 4 Rep protein has the amino acid sequence set forth in SEQ ID NO:11.

20. The vector system of claim 4, wherein the adeno-associated virus 4 Rep protein has about 95% homology with the amino acid sequence set forth in SEQ ID NO:11.

21. The vector system of claim 3, wherein the first vector further comprises a nucleic acid encoding an AAV5 Rep protein.

22. The vector system according to claim 4, wherein the first vector further comprises a nucleic acid encoding an AAV2 capsid protein.

23. The vector system according to claim 4, wherein the first vector further comprises a nucleic acid encoding an AAV3 capsid protein.

24. The vector system of claim 4, wherein the adeno-associated virus 4 capsid protein has the amino acid sequence set forth in SEQ ID NO:4.

25. The vector system of claim 4, wherein the adeno-associated virus 4 capsid protein has the amino acid sequence defined by amino acids 438-601 set forth in SEQ ID NO:4.

26. The vector system of claim 4, wherein the adeno-associated virus 4 capsid protein has about 98% homology to the amino acid sequence set forth in SEQ ID NO:4.

27. The vector system of claim 4, wherein the adeno-associated virus 4 capsid protein has the amino acid sequence set forth in SEQ ID NO:16.

28. The vector system of claim 4, wherein the adeno-associated virus 4 capsid protein has about 98% homology to the amino acid sequence set forth in SEQ ID NO:16.

29. The vector system of claim 4, wherein the adeno-associated virus 4 capsid protein has the amino acid sequence set forth in SEQ ID NO:18.

30. The vector system of claim 4, wherein the adeno-associated virus 4 capsid protein has about 98% homology to the amino acid sequence set forth in SEQ ID NO:18.

31. The vector system according to claim 4, wherein the first vector further comprises a nucleic acid encoding an AAV5 capsid protein.

32. A vector system according to claim 3, wherein the second vector further comprises a promoter between the inverted terminal repeats.

33. A vector system according to claim 32, wherein the promoter is functionally linked to an exogenous nucleic acid.

34. A method of making a recombinant particle for delivering an exogenous nucleic acid to a cell, comprising delivering to a cell having helper function the vectors of the vector system of claim 33.

35. The method of claim 34, wherein the helper function is provided by a helper virus.

* * * * *